(12) United States Patent
De Haan et al.

(10) Patent No.: US 9,125,353 B2
(45) Date of Patent: Sep. 8, 2015

(54) PARTHENOCARPIC GENETIC ELEMENTS DERIVED FROM S. HABROCHAITES

(75) Inventors: Anita Afke De Haan, Bleiswijk (NL); Paulus Cornelis Maris, Benthuizen (NL)

(73) Assignee: Monsanto Invest B.V., Bergschenhoek (NL)

( * ) Notice: Subject to any disclaimer, the term of this patent is extended or adjusted under 35 U.S.C. 154(b) by 853 days.

(21) Appl. No.: 12/619,051

(22) Filed: Nov. 16, 2009

(65) Prior Publication Data

US 2010/0146656 A1 Jun. 10, 2010

Related U.S. Application Data

(63) Continuation of application No. PCT/NL2008/050296, filed on May 18, 2008.

(60) Provisional application No. 60/938,904, filed on May 18, 2007.

(30) Foreign Application Priority Data

May 18, 2007 (EP) .................................... 07108504

(51) Int. Cl.
*A01H 1/02* (2006.01)
*A01H 1/04* (2006.01)
*A01H 5/08* (2006.01)
*C12Q 1/68* (2006.01)
*A01H 1/00* (2006.01)
*A01H 5/00* (2006.01)

(52) U.S. Cl.
CPC .. *A01H 1/04* (2013.01); *A01H 1/00* (2013.01); *A01H 1/02* (2013.01); *A01H 5/00* (2013.01); *A01H 5/08* (2013.01); *C12Q 1/6895* (2013.01)

(58) Field of Classification Search
None
See application file for complete search history.

(56) References Cited

FOREIGN PATENT DOCUMENTS

| EP | 1428425 A1 | 6/2004 |
|---|---|---|
| WO | 98/24301 A1 | 6/1998 |
| WO | 99/21411 A1 | 5/1999 |
| WO | 00/74468 A1 | 12/2000 |
| WO | 2006/046861 A2 | 5/2006 |

OTHER PUBLICATIONS

Mazzucato et al (Development 125: 107-114, 1998).*
Baggett et al (HortScience 32(7): 1299-1300, 1997).*
International Search Report Relating to correspondlng PCT/NL2008/050296.
Finkers, Richard, "The Genetics of Botrytis Cinerea Resistance in Tomato," (2007), Thesis Wageningen University, The Netherlands.
Coaker, G.L., et al., "Mapping, Genetic Effects, and Epistatic Interaction of Two Bacterial Canker Resistance QTLs from Lycopersicon Hirsutum," Theor Appl. Genet (2004) 108: 1047-1055.
Bai, Yulling, et al., "QTLs for Tomato Powdery Mildew Resistance (Oidium Lycopersici) in Lycopersicon Parviflorum G1.1601 Co-Localize with Two Qualitative Powdery Mildew Resistance Genes," MPMI vol. 16, No. 2, 2003, pp. 169-176.
Bernacchi, D., et al., "Advanced Backcross TL Analysis in Tomato," Theor Appl Genet (1998) 97: 381-397.
Haanstra, J.P.W., et al., "An Integrated High-Density RFLP-AFLP Map of Tomato Based on Two Lycopersicon Esculentum X L. Pennellii F2 Populations," Theor Appl Genet (1999) 99: 254-271.
Department of Horticulture, Purdue University, Tomato Genetics Cooperative Report 36:1 and 68, 1986.
Finkers, Richard, et al., "The construction of a *Solanum habrochaites*, LYC4 introgression line population and the identification of QTLs for resistance to *Botrytis cinerea*," *Theor. Appl. Genet.* 114:1071-1080, 2007.
Gorguet, Benoit, et al., "Mapping and characterization of novel parthenocarpy QTLs in tomato," *Theor. Appl. Genet.* 116:755-767, 2008.

* cited by examiner

*Primary Examiner* — David T Fox
(74) *Attorney, Agent, or Firm* — Dentons US LLP

(57) ABSTRACT

The present invention relates to a method of producing a parthenocarpic, and optionally male sterile, tomato plant comprising introgressing into said plant a genetic region from Chromosome 4, 5 and/or 12 of *S. habrochaites* LYC4/78, a representative sample of seed of which was deposited on 13 Nov. 2007 with the NCIMB under Accession number 41517, wherein the genetic region from Chromosome 4 of *S. habrochaites* LYC4/78 includes at least one marker selected from Marker CD59, RFLP Marker CT229, and COS Marker T1068, and wherein the genetic region from Chromosome 5 of *S. habrochaites* LYC4/78 includes at least one marker selected from COS Marker T1181, RFLP Marker TG441 and/or RFLP Marker CD31(A).

9 Claims, 4 Drawing Sheets

SEQUENCE LISTING

<160> NUMBER OF SEQ ID NOS: 86

<210> SEQ ID NO 1
<211> LENGTH: 528
<212> TYPE: DNA
<213> ORGANISM: Artificial Sequence
<220> FEATURE:
<223> OTHER INFORMATION: TG609Fd

<400> SEQUENCE: 1

| | | | | | |
|---|---|---|---|---|---|
| gagacagctt | gcatgcctgc | agaggtgata | aattcaccaa | ggtttcatat | ttaggaaaca | 60 |
| agaaaattaa | aagatcatta | acacagatga | aaggatatga | ctaggaggca | atgactgatc | 120 |
| tttgactatc | aaatacttct | cagggaaaca | atgtgaatgg | gcttttacat | gcagagatat | 180 |
| tgattgtgat | catgttgaag | aacttaggaa | acatgaaatt | aaatgatcat | taacactgat | 240 |
| gcaaggatat | gccaagtagg | caagcaaatt | aaggttgaac | ataaatgtct | gtgatctttg | 300 |
| actatcaaat | atcttctcag | aaaaaaaat | gtgaatgctc | atttacatgc | agagatggct | 360 |
| attgtgatca | tgtggctcag | ccttgagtct | atattgaggt | gcagacaaca | tagtccctaa | 420 |
| ccacatgtgt | gatcaagcaa | cttttttgat | gtccacaggg | ttataagtag | caacattta | 480 |
| agcaagaaaa | aacacaggat | cactattgag | tcagctgctg | ttgcctgt | | 528 |

<210> SEQ ID NO 2
<211> LENGTH: 537
<212> TYPE: DNA
<213> ORGANISM: Artificial Sequence
<220> FEATURE:
<223> OTHER INFORMATION: TG609Rv

<400> SEQUENCE: 2

| | | | | | |
|---|---|---|---|---|---|
| ggagacaagc | ttgcatgcct | gcagaggtga | taaattcacc | aaggtttcat | atttaggaaa | 60 |
| caagaaaatt | aaaagatcat | taacacagat | gaaaggatat | gactagtagg | caatgactga | 120 |
| tctttgacta | tcaaatactt | ctcagggaaa | caatgtgaat | gggcttttac | atgcagagat | 180 |
| attgattgtg | atcatgttga | agaacttagg | aaacatgaaa | ttaaatgatc | attaacactg | 240 |
| atgcaaggat | atgccaagta | ggcaagcaaa | ttaaggttga | acataaatgt | ctgtgatctt | 300 |
| tgactatcaa | atatcttctc | agaaaaaaaa | atgtgaatgc | tcatttacat | gcagagatgg | 360 |
| ctattgtgat | catgtggctc | agccttgagt | ctatattgag | gtgcagacaa | catagtccct | 420 |
| aaccacatgt | gtgatcaagc | aactttttg | atgtccacag | gtttataagt | aggcaacatt | 480 |
| taagcaagaa | aaaacacagg | atcactattg | agtcagctgc | tgttgcctgt | tactgag | 537 |

<210> SEQ ID NO 3
<211> LENGTH: 517
<212> TYPE: DNA
<213> ORGANISM: Artificial Sequence
<220> FEATURE:
<223> OTHER INFORMATION: TG62Fd

<400> SEQUENCE: 3

| | | | | | |
|---|---|---|---|---|---|
| caaaatgctt | cagctactgg | ctaaatgaag | tatgttctca | acatattcac | aagcttctgt | 60 |
| cttcgaagct | caagaagtgt | cggtattatc | tgaattaaat | agtaaagcaa | agagatggtt | 120 |
| ttatgtttct | taagcagcat | ttcttagctt | aacggccctc | cagatatatg | gtggacaaaa | 180 |
| tagaatccat | tagatataac | aaatgggatt | agtataatga | tcttttactt | tgttagatga | 240 |
| tcatactaac | agattgcaag | ttaatcatat | ccaacatatt | ctgtagatat | ttcacattgg | 300 |
| ctagcatgag | gaaaggtcat | gtaggaaatt | gaatagagtt | caattttggg | aaaagttgca | 360 |

```
ttgaagaagg taacttcaac aaacgtgtga aaaaatcaca tttgagttgc ccgctcacca    420
tcgtgattcc agtacgaact actcaaaaat ttacttttga gccttaaaca tcattttaag    480
ccttgaaaag ctgcttttga aaagatctaa gcaagat                             517
```

<210> SEQ ID NO 4
<211> LENGTH: 537
<212> TYPE: DNA
<213> ORGANISM: Artificial Sequence
<220> FEATURE:
<223> OTHER INFORMATION: TG62Rv

<400> SEQUENCE: 4

```
ggagaatatt gtcactctat cagatagttc aaaactatcg agaatgaaa tggtcaattc      60 ttctcacaag atattcatgc ctagttgcag tgtccgaatt aacataacat gctcaatttt    120
catatcttgc agcaaaattt atcattgaaa ctctctgaga tggaaacaga gaacaaagac    180
catattggaa agcttcaatc agacatgcag aaaaaggaag atgagattca tgttttacgc    240
aaggaaattg acaattacac ggaaacagtg gattcactgg agaagcatgt tacagagatt    300
aacaataaat tggaggagaa agatcagctt gttcaggaac ttcaggacaa ggagaagcag    360
ttggaagctg acagagaaaa ggttttttact acggatactt ttagttctac aaattctatt    420
ataaccaata caatgtgttc aagtgactag tgttttgcac cttgttgcag attcaggcat    480
ctttgcttgc tgctgaaagc aagctcacag aatccaaaaa gcagtatgat cagatgt       537
```

<210> SEQ ID NO 5
<211> LENGTH: 478
<212> TYPE: DNA
<213> ORGANISM: Artificial Sequence
<220> FEATURE:
<223> OTHER INFORMATION: TG555Fd

<400> SEQUENCE: 5

```
aattcggagc tcactgcttc taatcctcag tgagacttat tttctacata ttaaacaata     60
agaaatttac gaaggaatat tatagactga attccttggt gacaagtatc aagcatcttt    120
gaccaagttt aaagttttgt agtggcagtt ctttttaagct ttacttgtgt gaggtagaca   180
tcaaggaaga taagtagcag ctactcttca cggagcagcc cataggacac tcaaattcac    240
tattgcgagg gtcaatctac caattatgg aacgatacca gtaaagtcat ttttatgtaa     300
acatcagaca gcttttgact aagcagagac atgaataagt tctatttgtt agaagtcgaa    360
gagacaaata agttaatttc acctatgcta taaaagagga ctcttatagt tataaataca    420
gtacatttta ttaagggttc taattgttga ctatgatagc aagcatgccg tactaatt      478
```

<210> SEQ ID NO 6
<211> LENGTH: 503
<212> TYPE: DNA
<213> ORGANISM: Artificial Sequence
<220> FEATURE:
<223> OTHER INFORMATION: TG555Rv

<400> SEQUENCE: 6

```
acattttgag gaagacagga gttatgtatc gccatctggt gtgctccaag aacatgacag     60
atataaaaga ccgcggggtg caccagagaa atgttgcatt ggagcatatt gaacatcata    120
ggctcaatgg aattgtttac tttgcagatg atgataatat ctactcactt gagttgtttg    180
agagcattag atcgatcaag taagttgaga ttcatcagtc ttgtttacat gacttgtctt    240
```

| | |
|---|---|
| tgttttgtcc tgctgtgagc atgttcagga tgatgttatg tgctttatgt agatgttcaa | 300 |
| gtcgataata gtgaatagtc tagagctatt tcacatatat tacaacttca ctaacaaatt | 360 |
| cttttcctgg tgtcctcggt tcatcactct tcatagttat aagaataaca gttgtagatt | 420 |
| agaccactgg tcgtgtgatt tttggactta attattatct caattcttcc tcaaaatagc | 480 |
| agtccttaga ttagaagctg agg | 503 |

<210> SEQ ID NO 7
<211> LENGTH: 454
<212> TYPE: DNA
<213> ORGANISM: Artificial Sequence
<220> FEATURE:
<223> OTHER INFORMATION: CT50Fd

<400> SEQUENCE: 7

| | |
|---|---|
| cttttttttt tttttatat attgtggtat agattattat ataataacaa ggtgaattaa | 60 |
| catgagaaat gaataattgt cacattcttg ttctgtccat tttccagtag cggctagttg | 120 |
| gaaaatttgt tgtaacatgt aacacaggct gtccacattc tactccagag agaaagttgg | 180 |
| taagtagtgg gggcaaaaga tagagacccc aatagctatc aattcacttt gttgacaatc | 240 |
| aagatttgag aaaaaagatc aaaactttac caacttagat agctccataa tcaactgtag | 300 |
| gtacaattct ttagtgaaat tgcggcgttc atcttctggg gacgaagagt aagtagacaa | 360 |
| tcaattgtct tgtagaactt gggctttacc attttcccta ggacataagc tcttgatcga | 420 |
| agcttgaagt ttaattttag tggcactggt aatg | 454 |

<210> SEQ ID NO 8
<211> LENGTH: 496
<212> TYPE: DNA
<213> ORGANISM: Artificial Sequence
<220> FEATURE:
<223> OTHER INFORMATION: CT50Rv

<400> SEQUENCE: 8

| | |
|---|---|
| tttttttttt ttttttagcca aaatgcatac aaaaactgat tcagaagata cgagcttggc | 60 |
| tccttcgtcg ccggacaata gagggccgac ggcgtattac gttcagagtc cgtcacgtga | 120 |
| ttctcacgat ggcgagaaga caacgacgtc gtttcactct actcctgtta tcagtcccat | 180 |
| gggttctcct cctcactctc actcatccgt cggccgtcac tcccgtgatt cctcttcctc | 240 |
| cagattctcc ggctccctca gcctggatc tcagaagatt ttacccgacg ccgccggagg | 300 |
| cgtcggcggc cgtcaccacc gcaaagggca gaagccctgg aaggaatgtg atgttatttg | 360 |
| aggaagaagg actacttgaa gatgatagat ccagtaaatc tcttccacgt cgttgctatg | 420 |
| tccttgcttt ttgttgttgg tttcttcgtc cttttctcct tctttgctct catcctttgg | 480 |
| ggtgctagtc gacctc | 496 |

<210> SEQ ID NO 9
<211> LENGTH: 26
<212> TYPE: DNA
<213> ORGANISM: Artificial Sequence
<220> FEATURE:
<223> OTHER INFORMATION: C2Fd (primer)

<400> SEQUENCE: 9

| | |
|---|---|
| tcatcatcaa ctatcgtgat gctaag | 26 |

<210> SEQ ID NO 10
<211> LENGTH: 23

```
<212> TYPE: DNA
<213> ORGANISM: Artificial Sequence
<220> FEATURE:
<223> OTHER INFORMATION: C2Rv (primer)

<400> SEQUENCE: 10
acgcttgcga gccttcttga gac                                              23

<210> SEQ ID NO 11
<211> LENGTH: 479
<212> TYPE: DNA
<213> ORGANISM: Artificial Sequence
<220> FEATURE:
<223> OTHER INFORMATION: CT128Fd

<400> SEQUENCE: 11
cttttttttt ttttcaacac aaacaaaatt tcattatatt gtcaggtagc acactacatc       60
tttacactgt catcaaacga ccagagactt gagaacgttt taagagattc attttccggg      120
gacaaagttt gtggcgaaag cccaggcatt gttgtttacg gggtctgcaa ggtggtcagc      180
aaggttctcc aatggaccct tccggtgaca atagcttga acaaagaatc caaacataga       240
gaacatagca agtctaccgt tcttgatctc ctttaccttg agctcagcaa atgcctctgg      300
gtcttcagca aggcctaatg ggtcgaagct gccaccaggg tagagtgggt cgacaacctc      360
accaagaggt ccaccagcaa tacggtatcc ctcaacagct cccatcaaca caacttggca      420
agcccagatg gccaagatgc tttgtgcatg gaccaagctt gggttgccca gtagtcaa       479

<210> SEQ ID NO 12
<211> LENGTH: 495
<212> TYPE: DNA
<213> ORGANISM: Artificial Sequence
<220> FEATURE:
<223> OTHER INFORMATION: CT128Rv

<400> SEQUENCE: 12
ctggtgatta cgggtgggat accgctggac tttcagcaga ccctgaaact tttgccaaga       60
accgtgaact tgaggtgatc cactgcagat gggctatgct tggtgctctt ggatgtgtct      120
tccctgagct cttggcccgt aatggtgtca agttcggtga ggctgtgtgg ttcaaggccg      180
gatcccagat cttcagtgaa ggtggacttg actacttggg caacccaagc ttggtccatg      240
cacaaagcat cttggccatc tgggcttgcc aagttgtgtt gatgggagct gttgagggat      300
accgtattgc tggtgggacc tcttggtgag gttgtcgacc cactctaccc tggtggcagc      360
ttcgacccat taggccttgc tgaagaccca gaggcatttg ctgagctcaa ggtaaaggag      420
atcaagaacg gtagacttgc tatgttctct atgtttggat tctttgttca agctattgtc      480
accggaaagg gtcca                                                       495

<210> SEQ ID NO 13
<211> LENGTH: 500
<212> TYPE: DNA
<213> ORGANISM: Artificial Sequence
<220> FEATURE:
<223> OTHER INFORMATION: TG599Fd

<400> SEQUENCE: 13
tgctttgaga cagatgtctc tcattaagtg actgaagctt tcttctagtt ggctagcata       60
ttcattttca gcatataatc tgtatcatga acaaaattgc gacagtattg aattttttatt     120 gttgaatagt cttttatta tccccgaagt tgagggtgga acttacattt tctgttgatc       180
```

```
cttgcttgct gttttttgtaa acaaaaaagc gtcacccatt attttctttt tattcttcct    240
aggttgggac taagattttt tgaaatgaga aggtattcg ctaccttgag ggctgtggtt      300
gaagtgatgg agtatctgag caaagatgca gctcctgatg gtgtgggaag cttataaag     360 gaggagggag tatttccttt catttctttg tatttccgtg tgtgtatagt ccggaactgg    420
ttccctactt atgaattctt tcatggtttg gtcaattgag aaggatcaag aaatctgatg    480
ctactttatc atgggaactt                                                500
```

<210> SEQ ID NO 14
<211> LENGTH: 525
<212> TYPE: DNA
<213> ORGANISM: Artificial Sequence
<220> FEATURE:
<223> OTHER INFORMATION: TG599Rv

<400> SEQUENCE: 14

```
gcttgcatgc ctgcagagtg gtcatacaat aaaaggtaaa aatcaacatt cttacctctg     60
gaaagaaacc aatagcattg gtcaatgatg ctgcctctag aggaacaata ttgtatggtg   120
caagttcccc tgataaagta gcatcagatt tcttgatcct tctcaactga ccaaaccatg   180
aaagaattca taagtaggga accagttccg gactatacac acggaaat acaagaaat     240 gaaaggaaat actacctcct cctttataag ccttcccaca ccatcaggag ctgcatcttt    300
gctcagatac tccatcactt caaccacagc cctcaaggta gcgaataccct ttctcatttc   360 aaaaaatctt agtcccaacc tagaaagaat aaaagaaaaa taatgggtga cgcttttttg   420
tttacaaaaa cagcaagcaa ggatcaacag aaaatctaag ttccaccctc aacttcgggg   480
ataataaaaa gactattcaa caataaaaat tcaatactgt cgcaa                    525
```

<210> SEQ ID NO 15
<211> LENGTH: 456
<212> TYPE: DNA
<213> ORGANISM: Artificial Sequence
<220> FEATURE:
<223> OTHER INFORMATION: TG10Fd

<400> SEQUENCE: 15

```
aactctgctc tgccaatagt agtcaggcag atcaagatgc tcaaaatttt ctatttgaat     60
tggaagcatc aagatggttc ttagcattta ttttagaaag actaaccata ttatcaaata   120
accagactga gacgcacaca aaagtttccc tctattattt ttataatgat gtgaagatgc    180
tacataatga gtcacttttg ccttacttta ctgcagatgg acctaccagg cccaaacgga    240
catgtagcta tgacagaaga gcaaccgcta tgaatgtctc aaactgttgg cctaggcgat    300
cagcacagat gatgaatctg gaagtacatt ccaagaagga agctggagc gtgggaacta     360 accagatgca ggggatgaat ccacaccttt cagttgatca tctgaaggga aaactaagaa    420
ttttcatgag aaaatgactg gctatttca actttg                               456
```

<210> SEQ ID NO 16
<211> LENGTH: 562
<212> TYPE: DNA
<213> ORGANISM: Artificial Sequence
<220> FEATURE:
<223> OTHER INFORMATION: TG10Rv

<400> SEQUENCE: 16

```
ttcaatgcat ttaagctcaa aaaacaaag ctgtaggaag gagcatatta gtagcctaac      60
tctgctctgc caataatagt taagcagatc aagatgctca aaattttcta attgaattgt   120
```

```
tagcatcaag atgcttctta gcatttattt tagaaagatt aaccatatta tcaaataacc    180
agacagagac gcacacaaaa gtttcaatct attattttta taatgatgtg aaaatgctac    240
ataatgagta cactttccct tactttactg cagatggacc taccaggccc aaacggtcat    300
gtagttatga cagaagaaca acagtatgaa tttctcaaac tgttggccaa ggtgatcagc    360
aaagattatg aatttggaag tacattccaa gaggaaagct ggagcatcgt aactaaccag    420
atgcagggga tgaatccaca cctttcagtt gatcatctga aggcaaaact aagaattttc    480
atgagaaaat actggttatt ttcaactttg ttggccagac gaggagtcca atgggataga    540
aggactaact caatgacgta tg                                              562
```

```
<210> SEQ ID NO 17
<211> LENGTH: 422
<212> TYPE: DNA
<213> ORGANISM: Artificial Sequence
<220> FEATURE:
<223> OTHER INFORMATION: TM2A
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 17
```

```
cnagctcgan nnaccctcac taaagggaac aaaagctgga gctccaccgc ggtggcggcc     60
gctctagaac tagtggatcc cccgggctgc aggctcctcc attgaaaagg gaatcaagtt    120
tgccaaagaa aactaaaaaa acaaaattat ggtctagttt tctatagtga cagttttgga    180
tcttttgggg tcaattgttt ttgtatcctt tgcaagtttc ttgcagccgg aggcttagat    240
ttagctcttt tgatattata cccaacattt ctacaaaata atgtatgcaa aactgggggc    300
ctatcccatt tgccttagtg tggaggtgtt attctcacat gaatcgtttt ccaattatgg    360
ttagtagcag acaattgatg caaaatgaag aaatgttcat gaccaaaaaa aaaaaaaaaa    420
aa                                                                    422
```

```
<210> SEQ ID NO 18
<211> LENGTH: 458
<212> TYPE: DNA
<213> ORGANISM: Artificial Sequence
<220> FEATURE:
<223> OTHER INFORMATION: TG551Fd

<400> SEQUENCE: 18
```

```
aatgaagttc agttgataag ctaaatggtg gaaatactaa ttttaattga cagtaacttt     60
gcatttcaag gtccatacca aaacatttgc taacaccagt tgctttgtca acgaaaacct    120
tggcactcaa aaccctacca aaaggctgaa atgcatttgc aagctcttga tcaccaaatt    180
cttgaggaat atggtaaata aatagattag caccaggtgg acctgtaaac agcaaaatcg    240
tttttgataa gtacaggttt atttctacat gttcaactac cactgccaag tacactagtt    300
caagtgacat ctccaccact taattgcata agctttacc aacgacaaat ataacaaact    360
tgtgcaagta atttgagttc ctgtctatac agtccagaat ctccatatgc tgctcatctc    420
acaatgttgg ttaaggaaat ttgtcaagta aagttcaa                             458
```

```
<210> SEQ ID NO 19
```

<211> LENGTH: 382
<212> TYPE: DNA
<213> ORGANISM: Artificial Sequence
<220> FEATURE:
<223> OTHER INFORMATION: TG551Rv

<400> SEQUENCE: 19

| | |
|---|---|
| catcttcaag tgtcagctca agtacagggg gtcaggttga aggttgttga acatttattt | 60 |
| tgtgaccttt ttagctctag aatttctgta gctaatcaag tacagtccca taacctaggg | 120 |
| gctgttaggg ttttctgctg aatgaggctg cttgtcttta ttttggttaa ttattttctg | 180 |
| gaaattgttc ctcgtcatag agaatagaag tagaagaaga agaagatagt ataatctatt | 240 |
| atatttgttt tttacttaat ttataaagat tccataaatg catgtgatct ttgatcaatg | 300 |
| atatcttata caagtgtatc actagaatct attatatttg gatttactta ttttatatag | 360 |
| gatttcataa acgcatgtga tc | 382 |

<210> SEQ ID NO 20
<211> LENGTH: 331
<212> TYPE: DNA
<213> ORGANISM: Artificial Sequence
<220> FEATURE:
<223> OTHER INFORMATION: CT173Fd

<400> SEQUENCE: 20

| | |
|---|---|
| ttttttttt taaaaattca aactccaatt atttgcagta taaaactaca gatacaaatc | 60 |
| ccagtacatg gtttgaggca cgataataag gtgctgatga aatccaagac atgagttcac | 120 |
| aatacattac tgaccaatat atttacaaag attaggtaa tggcagtaaa atcgctgatt | 180 |
| acagacaaca ttcttgggat atatttcatc ttaaagatta ggattagtag tatgtgtggc | 240 |
| agtcacagta gagaccatgg catcaactcc gcagatattg tgaccctgc agatcttgta | 300 |
| atatccgtgt tctccccaag tctttcccca a | 331 |

<210> SEQ ID NO 21
<211> LENGTH: 331
<212> TYPE: DNA
<213> ORGANISM: Artificial Sequence
<220> FEATURE:
<223> OTHER INFORMATION: CT173Rv

<400> SEQUENCE: 21

| | |
|---|---|
| ttggggaaag acttggggag aacacggata ttacaagatc tgcagggtc acaatatctg | 60 |
| cggagttgat gccatggtct ctactgtgac tgccacacat actactaatc ctaatctta | 120 |
| agatgaaata tatcccaaga atgttgtctg taatcagcga ttttactgcc attaccctaa | 180 |
| tctttgtaaa tatattggtc agtaatgtat tgtgaactca tgtcttggat ttcatcagca | 240 |
| ccttattatc gtgcctcaaa ccatgtactg ggatttgtat ctgtagtttt atactgcaaa | 300 |
| taattggagt ttgaattttt aaaaaaaaaa a | 331 |

<210> SEQ ID NO 22
<211> LENGTH: 478
<212> TYPE: DNA
<213> ORGANISM: Artificial Sequence
<220> FEATURE:
<223> OTHER INFORMATION: TG254Fd

<400> SEQUENCE: 22

| | |
|---|---|
| ctagttggat tgaaacaatt gggaatatag tgtaggaaga cttcggggca attatctgct | 60 |
| ttcttctata tcaaactggg tctattgaag aattacaaac tggaccttaa atcttttgcc | 120 |

```
agtttttgta aaattgataa acttttgata ttttattatg gaaattcaaa atatatctta    180
atagtagctt gttaatttat ttcaagagac cctttcatt gttcatagtt cattatcatc     240
```

```
agtttttgta aaattgataa acttttgata ttttattatg gaaattcaaa atatatctta    180
atagtagctt gttaatttat ttcaagagac ccttttcatt gttcatagtt cattatcatc    240
cccttatcag tagtgcacca agggtgtgac ctagtggtca attaagtatg aatcatgagt    300
cttagacaga aacactaggt gattttcttc catgtgtcct agcctcttag cttggtgga     360 tagaggaggt atcctgtctt tcccctttcc agaaattcat agcattattt tctgttcttt    420
attgataaat tattcattag aacagttatt agaaatgtgg aactggttga ggtaggcg     478
```

<210> SEQ ID NO 23
<211> LENGTH: 493
<212> TYPE: DNA
<213> ORGANISM: Artificial Sequence
<220> FEATURE:
<223> OTHER INFORMATION: TG254Rv

<400> SEQUENCE: 23

```
cagaacagag aacatgtaaa gttgttcaac taatgagcat atttagaaaa acttagtggc     60
tatcaatagt tggcaatatg aaaactaaga tagtgtggtc acctgttgat caatttcttc    120
ttcaataggc atcttgtcag cttcctcttg taacaaggct ttcatttgtg acttgagaat    180
atatccagga ggaagtgcat gcctgtaatg gcattcttta ccatttggac aggcccagaa    240
ccaaccgtac tgctttttct ccacagcatc aaaaagaat ttacatacct gcatataaac     300
caaatcataa gcttgattta tgaaacgagc actgcattca tgtttggcaa tatttgactg    360
gaggaggagt tttaaagggg gaaattaaga ctatagacac atacactaaa tatgcataaa    420
acgccaaaag taccctggtt tcctatccag ttaaggcaac agtagcagaa aatgagtgtt    480
gtaatgagtc aat                                                       493
```

<210> SEQ ID NO 24
<211> LENGTH: 465
<212> TYPE: DNA
<213> ORGANISM: Artificial Sequence
<220> FEATURE:
<223> OTHER INFORMATION: TG223Fd

<400> SEQUENCE: 24

```
tattcaagaa aatattgtgt agtgttctcc aatattcaac tatttaagtt caatggatct     60
agacacacaa tattattaat tctcgtcgcc gatgggatgg ttgagtgatt gaagcatagg    120
aataacatcc tggagattct aggtttggac tccagtttga acataagtgt gagcccatct    180
gctttatctt acaagttcaa ttcaaacttg tgtgagtggg ccatagtaga tccatgcaaa    240
atagtggtta tgacgctatg gtgagttcat gagaagaatt attgttcctt aggaacagtg    300
acaggaaatt caatggtcaa ataacatcaa gaagactttt tggattagtt actgagtgat    360
gttcagaaga gggactaaat atctaacatg cccccctcaag ctccagatgg taaagcaact   420
tgagtttgag ttactagaat ttagtaacat aaaaaggttt tccat                    465
```

<210> SEQ ID NO 25
<211> LENGTH: 393
<212> TYPE: DNA
<213> ORGANISM: Artificial Sequence
<220> FEATURE:
<223> OTHER INFORMATION: TG223Rv

<400> SEQUENCE: 25

```
tttccacaca cacaaaaaaa acatcttgaa cacactgtaa tcccctctt catcaaattc      60
```

| tcctgtgtca acacaacttc cttagccagt aaccacacaa cttccctctt ctgaacatta | 120 |
| caaagtcgct gatccagaaa gtcttgttct tgatgctatt tgaccattga atttcctgtc | 180 |
| actatccaac atgaatagtg tttgtaggga ataaattgaa atcagattac aaggatccaa | 240 |
| atatccatcc ccaacaatgt actgtttatg cccgaaggtg aggataaaaa gatggaaaac | 300 |
| cttttatgt tactaaattc tagtaactca aactcaagtt gctttaccat ctggagcttg | 360 |
| agggggcatg ttagatattt agtccctctt ctg | 393 |

<210> SEQ ID NO 26
<211> LENGTH: 544
<212> TYPE: DNA
<213> ORGANISM: Artificial Sequence
<220> FEATURE:
<223> OTHER INFORMATION: TG47Fd

<400> SEQUENCE: 26

| tgcagttgaa ttcgtcttct taacactatt ctcttatgct gtgcatcaag acaaccaccc | 60 |
| tcatgggcg gtcattgctt cttcaggcat gaccctacag ttagtacatt tggttttacc | 120 |
| aaatcttctt ctaaggataa atctatttga ctatggttca ctctctaaat cataagctga | 180 |
| aacaacatca acataccccg tgtaaatcat aagctaaaac aaactctaga atagccttac | 240 |
| ctcatcattc ctaggaccat aattatatct atacttagtc aaaatcatca taaaatttac | 300 |
| ctacaagacc atttagatct cacctgatta agatttgttg ttactcgta atcccttgaa | 360 |
| ctaaggtgta acatcttaac ccctccttt gagtatttat accatcatat tttgaaactt | 420 |
| ctcgtaggtt catatgtttc ttttggtact tgttagtata gcttggagtg ggacccaagg | 480 |
| ggctccagtg agttctagac aagaaaaacg agatttgaac attgcagatt ttatgttttc | 540 |
| tggt | 544 |

<210> SEQ ID NO 27
<211> LENGTH: 484
<212> TYPE: DNA
<213> ORGANISM: Artificial Sequence
<220> FEATURE:
<223> OTHER INFORMATION: TG47Rv

<400> SEQUENCE: 27

| ctttgtttgc ttgcaagaca gagatttata cacgctaatg ctatctttt gtgtcattaa | 60 |
| cagctagttt gatttgcttg gttaatacag ttatggtaga tagagaagat agtttcaaaa | 120 |
| tagaaagaat gatgtagaca gcattaatga atctttctcc ttacaattgt acctttgaca | 180 |
| aggaatccac cttttatagg tagtttggtg agtttgatgg aagattgtgg ttgaatctgg | 240 |
| ttgagtcata gacactactt gtacattctt ttatgacact gacttgatgt tgtaagagtg | 300 |
| aaatgtatag acttatcaac aaataacaga gtagaaataa aagtaggttg aagatagctt | 360 |
| cttgtttggt tctaacttgc tcctttgttg actgatatga taacattgtg tcaatataag | 420 |
| atgattcaaa atgttgcctg aatttttatg aaattgatat tcatcgtcca gtttagagag | 480 |
| ttct | 484 |

<210> SEQ ID NO 28
<211> LENGTH: 440
<212> TYPE: DNA
<213> ORGANISM: Artificial Sequence
<220> FEATURE:
<223> OTHER INFORMATION: TG393Fd

<400> SEQUENCE: 28

```
actgactaag ctgctggatt tgattagccg aaggaattta cttttggtta catcttgctc    60
catcacctTT gtctttatct aggtcaatct tgtaccatag atgcaaataa cactatgaac   120
agattaacaa tgtcttgagg aggattaggc tgtcaacagc ctgcataata acaggaacaa   180
cattggcgtt tgtttgcatc agttactgtg actctgatta aggagaaaaa tgtggcatcc   240
tctgcttata ctgtcagtgt gtatacttgt caggttaagt tggttgctat aatctttaat   300
aattcttgat tttgtggttg tttctgaagt aaattgatat gtgggccttt gagctggagg   360
agatggtact ttagctattc actaacaatc gtttaccttA aaaatgttat tctgtaagta   420
tctaaccaaa ttctgatcac                                               440

<210> SEQ ID NO 29
<211> LENGTH: 474
<212> TYPE: DNA
<213> ORGANISM: Artificial Sequence
<220> FEATURE:
<223> OTHER INFORMATION: TG393Rv

<400> SEQUENCE: 29
tgcagacacc aagaaacaa ttggttatat aaaaaacaat ccacaatcat tctctataga    60
agtcacgcaa agacactaca taacctccaa gtgcaatgaa gaggatgcag aataagaagc   120
tcagaacttc caaagaaaaa ggtgactgaa ataagtttg ctgaaaaggt acaaggcaag   180
ttctaattct caactagctt taggtataca ctaagaaaaa ggaaaataaa ttccaaacag   240
aagtttccat cctacctagt acataaaaga aaaggtaaa aaggaacata tggaagtgtt   300
cccctgttac ctaaacttTT ggtgataaac agtaatcatg attaccccca cctcacacac   360
caccactaca gcacaaaaat tagaaatgtt gtatggacca tgatcaacca gccaagaatc   420
ccagaaggag aataaaggag ttctcttaat cacaagagga gaatatcatc tact         474

<210> SEQ ID NO 30
<211> LENGTH: 182
<212> TYPE: DNA
<213> ORGANISM: Artificial Sequence
<220> FEATURE:
<223> OTHER INFORMATION: CT19Rv

<400> SEQUENCE: 30
gccccaaaac tcctgctgga ttttactgga tctccacttg ctgcggacat tgcttgcctc    60
cgacaatcat cttcccaact tcttcctttt tgtcttgaaa ttaatccctt gtacccattg   120
ctgcttctaa atgacctcct gcatcccggc ggatccacta ggtctaaagc tgccgccccc   180
gc                                                                  182

<210> SEQ ID NO 31
<211> LENGTH: 521
<212> TYPE: DNA
<213> ORGANISM: Artificial Sequence
<220> FEATURE:
<223> OTHER INFORMATION: TG68Fd

<400> SEQUENCE: 31
ggattttgat gaacttgtat ctgtgcttct agctccacct aggatgagtt tggatttgta    60
cgattaacaa atgtttgagc tgaaagaatt aaatttgatt acacctgcct ttacatattt   120
ttgttgcgta aggattttct atgaagaata tatatgtatg tatgtgtaaa ggatgcacta   180
agcatctcgc attttgataa agaaatgaac tttgggctta actcaactcc aaaagttagc   240
```

```
tcatgaagtg aggatatcgc gtaagaccgt ataaggagac ctagaaccca tcccacaaca      300
atgtgtgact ccaacacatt cacgcaagtt ctggggaagg gttgcactcg taagggttgt      360
gatgtaggca gccataattg tgtgtaccca ttcgttagaa aactacactg tgcaagtgga      420
gttaaattgt atcttttttg gttttgtgtg agttgttcaa tccccttgac atgaaaaaaa      480
gaagcaaaat tcaagtataa tggtaaaagg ggattcaaaa t                         521
```

```
<210> SEQ ID NO 32
<211> LENGTH: 485
<212> TYPE: DNA
<213> ORGANISM: Artificial Sequence
<220> FEATURE:
<223> OTHER INFORMATION: TG68Rv

<400> SEQUENCE: 32
ttgggtcagc catagtactt cgtgatatat ctctgacaga agatatctgc tcaagaccat       60
gaacaatacg gagacataag aaggaaagaa gttcagtgca gcacaaaatt ttaataagtt      120
aacttaaagg gggataagag gcaaaaccaa tataaaagtt tggacagaca aattttaatt      180
agtatcaaag agtgaatgat gctaaaagaa gagatgctta aatatctgat actataaagt      240
aagccatgac taattggtaa ttatgaatgg catatgatac gactatcagt tttgactgtt      300
gtctacaata atgatttcag aaacatatga tatatttcaa atagaattga ataacaacac      360
ttgttcaaat acctagctct cggaggcaga tccagaattt tagaaagtgg gtgcagtaaa      420
tcacaagagt acacctctgc tagaatgggt gtgtactgta acaaaacctg ttttgatatg      480
catat                                                                 485
```

```
<210> SEQ ID NO 33
<211> LENGTH: 475
<212> TYPE: DNA
<213> ORGANISM: Artificial Sequence
<220> FEATURE:
<223> OTHER INFORMATION: TG565Fd

<400> SEQUENCE: 33
actagcatct cttggaggat gctgaggtgt caagtggtgt tgaccactcg ttaccactga       60
ttcacagctg gtgtctttcg aagcaagctt cgtctgcaaa acaagaatca cactttaatc      120
ctctgttacc taaaacaat agttgtttga tgtaatgaaa aagaattttt cacttcaatg       180
atggaaagaa aatcttacag tttgagtttg cttgcgaaag tagccatttt catacaccag      240
ttgagaaact tgcttctgca atctatcatt ctcttccatt aatagcttgt tcattgctga      300
cagcttccta ttcacaccct gaagccttga tgactctttc ctctgttttt ccctacatct      360
atacaactca agaaacaat caattatact tcaaattaat tggggtcgct aaaaatgaat       420
cctttagact aacaacatcc cacaagtcct taccccctacc tcgcagaggt agaga          475
```

```
<210> SEQ ID NO 34
<211> LENGTH: 490
<212> TYPE: DNA
<213> ORGANISM: Artificial Sequence
<220> FEATURE:
<223> OTHER INFORMATION: TG565Rv

<400> SEQUENCE: 34
tcagcaaaat gtcacacaga gagtacagta gtagagcaca gtagagtagg gagaagttgc       60
ctcaaaagag gaaaagaaaa ggtaacgaac cacacatttg acagctcaaa accactttac      120
caatccaaac aaaaaatcat cacattatcc ctcccttctc tcctttctct attactctca      180
```

```
tttccccaa gtttcaggta ccttttcct aacataatcc gcccatagtg ttcatcattc        240
aagatctgtc cttttgagga gacttcattc cttactatgg tcttcttttt ttgatgattt        300
cttatgtgag atgttgaaaa ctggaaagaa gtgataaaga taggaggttt ggtttctggg        360
gtttgtttat tttgctttac aagggttaaa gattggatct tttttagttt tggtagatac        420
ccatgtctaa tcttgtttca gaattcaaaa ggttggtact ttactgtttt gcaagtggat        480
gacagaggag                                                              490

<210> SEQ ID NO 35
<211> LENGTH: 469
<212> TYPE: DNA
<213> ORGANISM: Artificial Sequence
<220> FEATURE:
<223> OTHER INFORMATION: TG296Fd

<400> SEQUENCE: 35
ttaggttttt gtgtggttca acgttttgg ttttgatttt tatgtgtttt cttagttcct         60
tgcttcacca ttttgatggt attttgagtt tttgatgttc tgtcggcata aagtagtgat        120
ttttcagaca gtttggtatt atggagtatg tttctttgct cttctctaat ttggattggt        180
tctgatttgt atatgcttgt tttagtttcg atggttttg agttttgat gattcattgg         240 cacaaagtag tgattttca gactgttggg ttttgtgggg ttcccgtgct tgctcttcac        300
taatttggat tggttctgat tgtatatgt tttagttttg atggttttg agttttgat         360 gattcatcgg cacaaagtag tgatctttca gacagttggg ttttgtgggg ttcacgtgct       420
tattcttcac tattctcggt tggtttgatt tgtaggtccg ttttagcat                   469

<210> SEQ ID NO 36
<211> LENGTH: 502
<212> TYPE: DNA
<213> ORGANISM: Artificial Sequence
<220> FEATURE:
<223> OTHER INFORMATION: TG296Rv

<400> SEQUENCE: 36
agaatataac aaaaaagcag ataaatcagt taattatgcc tcaatctcaa caagtgaata        60
acaaatccta tcagaagata tagtagacga taaacagtga aggtagaagc ctaactctat       120
gacattatct tgagacccaa aacacttcat caaagactca aaagaaataa tttgttcacc       180
aagtactatt aactaattat caaaactaga attctcaaaa taaaaaataa caaatcttat       240
cagtcacatg gacattcatt aaacatcatg aagaagacaa caagggaagg tcaaaactgg       300
actccatggc acataagata ataacaaaag gtagtttaag gcctaaaaca cttcaaaaat       360
aaaatttatt caccagatat caataatatt atctgttctt ccttcattca tgaggggcat       420
gcacaagaga caatatacat catttctcct tttacttttt ctttcctgag gaagtaaaag       480
gagcagaaag cagatagaaa ga                                                502

<210> SEQ ID NO 37
<211> LENGTH: 21
<212> TYPE: DNA
<213> ORGANISM: Artificial Sequence
<220> FEATURE:
<223> OTHER INFORMATION: CT229Fd (primer)

<400> SEQUENCE: 37
atgggctggg atcgtagtaa a                                                  21
```

<210> SEQ ID NO 38
<211> LENGTH: 21
<212> TYPE: DNA
<213> ORGANISM: Artificial Sequence
<220> FEATURE:
<223> OTHER INFORMATION: CT229Rv (primer)

<400> SEQUENCE: 38
aagcttgcga ttcccataac a                                              21

<210> SEQ ID NO 39
<211> LENGTH: 19
<212> TYPE: DNA
<213> ORGANISM: Artificial Sequence
<220> FEATURE:
<223> OTHER INFORMATION: T1068Fd (primer)

<400> SEQUENCE: 39
caaagcaatg ggcaatggt                                                 19

<210> SEQ ID NO 40
<211> LENGTH: 21
<212> TYPE: DNA
<213> ORGANISM: Artificial Sequence
<220> FEATURE:
<223> OTHER INFORMATION: T1068Rv (primer)

<400> SEQUENCE: 40
acacagcagt ttcagtagga c                                              21

<210> SEQ ID NO 41
<211> LENGTH: 19
<212> TYPE: DNA
<213> ORGANISM: Artificial Sequence
<220> FEATURE:
<223> OTHER INFORMATION: TG272Fd (primer)

<400> SEQUENCE: 41
gattttgccc cctctacca                                                 19

<210> SEQ ID NO 42
<211> LENGTH: 21
<212> TYPE: DNA
<213> ORGANISM: Artificial Sequence
<220> FEATURE:
<223> OTHER INFORMATION: TG272Rv (primer)

<400> SEQUENCE: 42
acatcttttc cttccctctg c                                              21

<210> SEQ ID NO 43
<211> LENGTH: 20
<212> TYPE: DNA
<213> ORGANISM: Artificial Sequence
<220> FEATURE:
<223> OTHER INFORMATION: TG264Fd (primer)

<400> SEQUENCE: 43
ggaacaggtc aggacagcat                                                20

<210> SEQ ID NO 44
<211> LENGTH: 20
<212> TYPE: DNA
<213> ORGANISM: Artificial Sequence
<220> FEATURE:
<223> OTHER INFORMATION: TG264Rv (primer)

```
<400> SEQUENCE: 44
tggctaactg acgaagacga                                          20

<210> SEQ ID NO 45
<211> LENGTH: 20
<212> TYPE: DNA
<213> ORGANISM: Artificial Sequence
<220> FEATURE:
<223> OTHER INFORMATION: TG62Fd (primer)

<400> SEQUENCE: 45
catgcctagt tgcagtgtcc                                          20

<210> SEQ ID NO 46
<211> LENGTH: 20
<212> TYPE: DNA
<213> ORGANISM: Artificial Sequence
<220> FEATURE:
<223> OTHER INFORMATION: TG62Rv (primer)

<400> SEQUENCE: 46
ttcagcagca agcaaagatg                                          20

<210> SEQ ID NO 47
<211> LENGTH: 20
<212> TYPE: DNA
<213> ORGANISM: Artificial Sequence
<220> FEATURE:
<223> OTHER INFORMATION: T1405Fd (primer)

<400> SEQUENCE: 47
caccaacaac tagcccttga                                          20

<210> SEQ ID NO 48
<211> LENGTH: 20
<212> TYPE: DNA
<213> ORGANISM: Artificial Sequence
<220> FEATURE:
<223> OTHER INFORMATION: T1405Rv (primer)

<400> SEQUENCE: 48
aagcaattcc tccagcttca                                          20

<210> SEQ ID NO 49
<211> LENGTH: 20
<212> TYPE: DNA
<213> ORGANISM: Artificial Sequence
<220> FEATURE:
<223> OTHER INFORMATION: CT50Fd (primer)

<400> SEQUENCE: 49
gacggcgtat tacgttcaga                                          20

<210> SEQ ID NO 50
<211> LENGTH: 20
<212> TYPE: DNA
<213> ORGANISM: Artificial Sequence
<220> FEATURE:
<223> OTHER INFORMATION: CT50Rv (primer)

<400> SEQUENCE: 50
ctagcacccc aaaggatgag                                          20

<210> SEQ ID NO 51
```

```
<211> LENGTH: 20
<212> TYPE: DNA
<213> ORGANISM: Artificial Sequence
<220> FEATURE:
<223> OTHER INFORMATION: TG441Fd (primer)

<400> SEQUENCE: 51
tgtcagcata ggcttttcca                                            20

<210> SEQ ID NO 52
<211> LENGTH: 18
<212> TYPE: DNA
<213> ORGANISM: Artificial Sequence
<220> FEATURE:
<223> OTHER INFORMATION: TG441Rv (primer)

<400> SEQUENCE: 52
cggtcgggaa aaatgaca                                              18

<210> SEQ ID NO 53
<211> LENGTH: 20
<212> TYPE: DNA
<213> ORGANISM: Artificial Sequence
<220> FEATURE:
<223> OTHER INFORMATION: CD31Fd (primer)

<400> SEQUENCE: 53
atctcgggat catggttgac                                            20

<210> SEQ ID NO 54
<211> LENGTH: 21
<212> TYPE: DNA
<213> ORGANISM: Artificial Sequence
<220> FEATURE:
<223> OTHER INFORMATION: TG318Fd (primer)

<400> SEQUENCE: 54
caagccatag aaattgccgt a                                          21

<210> SEQ ID NO 55
<211> LENGTH: 21
<212> TYPE: DNA
<213> ORGANISM: Artificial Sequence
<220> FEATURE:
<223> OTHER INFORMATION: TG318Rv (primer)

<400> SEQUENCE: 55
tgctctctct gtgatggaag c                                          21

<210> SEQ ID NO 56
<211> LENGTH: 24
<212> TYPE: DNA
<213> ORGANISM: Artificial Sequence
<220> FEATURE:
<223> OTHER INFORMATION: TG358Fd (primer)

<400> SEQUENCE: 56
caacttttcc aggttcattt tctc                                       24

<210> SEQ ID NO 57
<211> LENGTH: 24
<212> TYPE: DNA
<213> ORGANISM: Artificial Sequence
<220> FEATURE:
<223> OTHER INFORMATION: TG358Rv (primer)

<400> SEQUENCE: 57
```
acacctacat gctactaagg ggtc                                          24

<210> SEQ ID NO 58
<211> LENGTH: 22
<212> TYPE: DNA
<213> ORGANISM: Artificial Sequence
<220> FEATURE:
<223> OTHER INFORMATION: TG60Fd (primer)

<400> SEQUENCE: 58
ttggctgaag tgaagaaaag ta                                            22

<210> SEQ ID NO 59
<211> LENGTH: 22
<212> TYPE: DNA
<213> ORGANISM: Artificial Sequence
<220> FEATURE:
<223> OTHER INFORMATION: TG60Rv (primer)

<400> SEQUENCE: 59
aagggcattg taatatctgt cc                                            22

<210> SEQ ID NO 60
<211> LENGTH: 20
<212> TYPE: DNA
<213> ORGANISM: Artificial Sequence
<220> FEATURE:
<223> OTHER INFORMATION: CT138Fd (primer)

<400> SEQUENCE: 60
accagccccg gaagatttta                                               20

<210> SEQ ID NO 61
<211> LENGTH: 21
<212> TYPE: DNA
<213> ORGANISM: Artificial Sequence
<220> FEATURE:
<223> OTHER INFORMATION: CT138Rv (primer)

<400> SEQUENCE: 61
gcggtcaact tcagcaacta t                                             21

<210> SEQ ID NO 62
<211> LENGTH: 19
<212> TYPE: DNA
<213> ORGANISM: Artificial Sequence
<220> FEATURE:
<223> OTHER INFORMATION: TG296Fd (primer)

<400> SEQUENCE: 62
tgttctgtcg gcataaagt                                                19

<210> SEQ ID NO 63
<211> LENGTH: 19
<212> TYPE: DNA
<213> ORGANISM: Artificial Sequence
<220> FEATURE:
<223> OTHER INFORMATION: TG296Rv (primer)

<400> SEQUENCE: 63
tgctaaaacg gacctacaa                                                19

<210> SEQ ID NO 64
<211> LENGTH: 155
<212> TYPE: DNA

<213> ORGANISM: S. habrochaites LYC4/78
<220> FEATURE:
<221> NAME/KEY: misc_feature
<222> LOCATION: (21)..(21)
<223> OTHER INFORMATION: n is a, c, g, or t

<400> SEQUENCE: 64

```
ttcattttgt tatttccttt ngccttcctc cactcagact ggagttcttc gttatcagca    60
aactgttcga cagttaaatg catgtatgtt cagtataagt aaaagggcaa cccaagcttc   120
cgctatgcac ggggtctgga gtagggccgg actat                              155
```

<210> SEQ ID NO 65
<211> LENGTH: 191
<212> TYPE: DNA
<213> ORGANISM: S. habrochaites LYC4/78

<400> SEQUENCE: 65

```
tggaagagat ttactggatc tatcatcttc aagtagtcct tcttcctcaa taacatcaca    60
ttccttccag ggcttctgcc ctttgcggtg gtgacggccg cctgcggcgt cgggtaaaat   120
cttccgagat ccaggcttga gggagccgga gaatctggag gaagaggaat cacgcgagtg   180
acggccgacc g                                                        191
```

<210> SEQ ID NO 66
<211> LENGTH: 250
<212> TYPE: DNA
<213> ORGANISM: S. habrochaites LYC4/78

<400> SEQUENCE: 66

```
cagaagttta acatcacaag ccactgaaga cgatgaaaga tgctatagaa atagtcacaa    60
ctgatgaaat cattactgag atagcaccaa ccaggtagaa tattttaacc aatgtgcaga   120
gcgttccaac taatacagca ttaaagatga taatatctca tgactattgc tgcttttgca   180
atgaaaacgg ggtttgtttc aaaaaatatg gtgtttgatt ttttttttaaa aaaagttcaa   240
cacttgatga                                                          250
```

<210> SEQ ID NO 67
<211> LENGTH: 175
<212> TYPE: DNA
<213> ORGANISM: S. habrochaites LYC4/78

<400> SEQUENCE: 67

```
ggctgtgata tcggagtcag agctctggct tcacatccaa tgaaagcaaa taagaaaggt    60
attggggaga agcacgttcc cataaccatt gccgggacta gaatctgcga tggtgagtgg   120
ctttatgcag atactgatgg cattctgatt tctaaaatgg agctatgtgt ttgag        175
```

<210> SEQ ID NO 68
<211> LENGTH: 338
<212> TYPE: DNA
<213> ORGANISM: S. habrochaites LYC4/78

<400> SEQUENCE: 68

```
tttccaaggc gaaaccaac tcccttgctg tcattggtca taatgccaac aatgcttata    60
ttcttcgtgg gaactatgac ggtcctcctt gcaaatacat cgaaatactc aaggcgttgg   120
ttggttatgc aaagtcagtt cagtaccaac agggttgcaa tgcggctaac tgcacgtctg   180
ctaacattga tcaagctgtc aacattgcaa gaaatgcaga ttatgttgtt ttagtcatgg   240
ggttggatca aactcaagag agggaacaat ttgatcgcga tgacttagtg ctcccggggc   300
```

```
agcaagaaaa tcttatcaat agtgttgcta aagctgca                              338
```

<210> SEQ ID NO 69
<211> LENGTH: 219
<212> TYPE: DNA
<213> ORGANISM: S. habrochaites LYC4/78

<400> SEQUENCE: 69

```
tataatggaa cagtatcaag gtaaaatatt gtataacaac tacaagactc actaggaatg      60
gtatacaagt gaaacgtaaa ttaacaacta caagactcac tacatagctg atgcgataat     120
tggtaattat gaagggcgaa atagtaaaat ttctttccaa gaaatcatgt cttttgtcct     180
catggctgaa gctcaattgt gtacaagaaa caaatgtac                            219
```

<210> SEQ ID NO 70
<211> LENGTH: 289
<212> TYPE: DNA
<213> ORGANISM: S. habrochaites LYC4/78

<400> SEQUENCE: 70

```
ttggttataa tagaatttgt agaactaaaa gtatccgtag taaaaacctt ttctctctca      60
gcttccaact gtttctcctt gtcctgaagt tcctgaacaa gctgatcttt ctcctccaat     120
ttattgttta tctctgtaac atgcttctcc agtgaatcca ctgttccgt gtaattgtca     180 atttccttgc gtaaaacatg aatctcatct cctttttct gcatgtctga ttgaagcttt    240
ccaatatggt ctttgttctc tatttccatc tcagagagtt tcaatgata                289
```

<210> SEQ ID NO 71
<211> LENGTH: 157
<212> TYPE: DNA
<213> ORGANISM: S. habrochaites LYC4/78

<400> SEQUENCE: 71

```
ggctattctt ggatggcttc tcaaggaaaa agaatgtctt tgtcaatgtt gcaattctcg      60
tattctttat aaatcaaagt ttcaagtcgg tggctgggtc acgaataaat agagtagaag    120
tatgctcaac atccctgtgt tacagtagtc ccactct                              157
```

<210> SEQ ID NO 72
<211> LENGTH: 194
<212> TYPE: DNA
<213> ORGANISM: S. habrochaites LYC4/78

<400> SEQUENCE: 72

```
taatttggat tggttctgat ttgtatatgc ttgttttagt ttcgatggtt tttgagtttt      60
tgatgattca ttggcacaaa gtagtgattt ttcagacagt tgggttttat ggggttcccg    120
tgcttgctct tcactaattt ggattggttc tgatttgtat atgtttgttt tagttttgat    180 ggttttgag tttt                                                        194
```

<210> SEQ ID NO 73
<211> LENGTH: 122
<212> TYPE: DNA
<213> ORGANISM: S. habrochaites LYC4/78

<400> SEQUENCE: 73

```
gatactcaaa aggaagcttg gtccagatga ccttcgcaca caggtacctt ctgtctcatg      60
cacatgtata cagcacgaac aaatgcgctc tcttcccaga ctggtgctgc ataaaaaatt    120
``` ac                                                               122

<210> SEQ ID NO 74
<211> LENGTH: 229
<212> TYPE: DNA
<213> ORGANISM: S. habrochaites LYC4/78

<400> SEQUENCE: 74
agctgaggtt tggattactg ggctgaaagc aataattacg aggggacgct ctcgcagagg    60
aaaatatgat gcaagaagtg aaactatgtt ttcggatagt ccacttggtc tacgagtcac   120
cacatcaact tctactattg tatgttggca ttttgttgta ccttcagttg tgtgtgttca   180
ttcttcctct cctatgacct cttcccctc caactgatcc aaaatgttg              229

<210> SEQ ID NO 75
<211> LENGTH: 155
<212> TYPE: DNA
<213> ORGANISM: S. lycopersicum cv. Moneymaker

<400> SEQUENCE: 75
ttcattttgt tatttccttt tgccttcctc cactcagact ggagttcttc gttatcagca    60
aactgttcga cagttaaatg catgtatgtt cagtataagt aaaagggcaa cccaagcttc   120
cactatgcac ggagtccgga gtagggccgg actat                            155

<210> SEQ ID NO 76
<211> LENGTH: 200
<212> TYPE: DNA
<213> ORGANISM: S. lycopersicum cv. Moneymaker

<400> SEQUENCE: 76
tggaagagat ttactggatc tatcatcttc aagtagtcct tcttcctcaa taacatcaca    60
ttccttccag ggcttctgcc ctttgcggtg gtgacggccg ccgacgcctc cggcggcgtc   120
gggtaaaatc ttctgagatc caggcttgag ggagccggag aatctggagg aagaggaatc   180
acgggagtga cggccgacgg                                             200

<210> SEQ ID NO 77
<211> LENGTH: 250
<212> TYPE: DNA
<213> ORGANISM: S. lycopersicum cv. Moneymaker

<400> SEQUENCE: 77
cagaagttta acttcacaag ccactgaaca cggtgaaaga tgctatagaa atagtcacaa    60
ctgatgaaat cattactgag atagcaccaa ccaggtagaa tatttaacc aatgtgcaga   120 gcgttccaac taacacagca ttaaagatga taatatctca tgactattgc tgcttttgca   180
atgaaaacgg ggtttgtttc aaaaaatatg gtgtttgatt tttttcaaa aaagttcaa    240 cacttgatga                                                       250

<210> SEQ ID NO 78
<211> LENGTH: 175
<212> TYPE: DNA
<213> ORGANISM: S. lycopersicum cv. Moneymaker

<400> SEQUENCE: 78
ggctgtgata tcggagtcag agctctggct tcacatccaa tgaaagcaaa taagaaaggt    60
attggggaga agcacgttcc cataaccatt gccgggacta gaatctgcga tggtgagtgg   120 cttatgcag ataccgatgg cattctgatt tctaaaatgg agctatgtgt ttgag        175

<210> SEQ ID NO 79
<211> LENGTH: 338
<212> TYPE: DNA
<213> ORGANISM: S. lycopersicum cv. Moneymaker

<400> SEQUENCE: 79

```
tttccaaagc gaaaaccaac tcccttgctg tcatcggtca taatgccaac aatgcttata      60
ttcttcgtgg gaactatgac ggtcctccct gcaaatacat cgaaattctc aaggcattgg     120
ttggttatgc aaagtcagtt cagtaccaac agggttgcaa tgcggctaac tgcacgtctg     180
ctaacattga tcaagctgtc aacattgcaa gaaatgcaga ttatgttgtt ttaatcatgg     240
ggttggatca aactcaagag agggaacaat tgatcgcga tgacttagtg ctcccggggc     300
agcaagaaaa tcttatcaat agtgttgcta aagctgca                             338
```

<210> SEQ ID NO 80
<211> LENGTH: 219
<212> TYPE: DNA
<213> ORGANISM: S. lycopersicum cv. Moneymaker

<400> SEQUENCE: 80

```
tataatggaa cagtatcaag gtaaaatatt gtataacaac tacaagattc actaggaatg      60
gtatacaagt gaaacgtaaa ataacaacta caagactcgc tacacagctg atgcgataat     120
tggtaattat gaagggcgaa atactcaaat ttctttccaa gaaatcatgt cttttgtcct     180
catggctgaa gctcaattgt gtccaagaaa caaatgtac                            219
```

<210> SEQ ID NO 81
<211> LENGTH: 289
<212> TYPE: DNA
<213> ORGANISM: S. lycopersicum cv. Moneymaker

<400> SEQUENCE: 81

```
ttggttataa tagaatttgt agaactaaaa gtatccgtag taaaaacctt ttctctgtca      60
gcttccaact gcttctcctt gtcctgaagt tcctgaacaa gctgatcttt ctcctccaat     120
ttattgttaa tctctgtaac atgcttctcc agtgaatcca ctgtttccgt gtaattgtca     180
atttccttgc gtaaaacatg aatctcatct tcctttttct gcatgtctga ttgaagcttt     240
ccaatatggt ctttgttctc tgtttccatc tcagagagtt tcaatgata                 289
```

<210> SEQ ID NO 82
<211> LENGTH: 157
<212> TYPE: DNA
<213> ORGANISM: S. lycopersicum cv. Moneymaker

<400> SEQUENCE: 82

```
ggctattctt ggatggcttc tcaaggaaaa agaatgtcta tgtcaatgtc tcaattctcg      60
tattctttat aaatcaaagt gtcaattcgg tggctgggtc acgaataaat agagtagaag     120
tatgctaaac atccctgtgt tacagtagtc ccactct                              157
```

<210> SEQ ID NO 83
<211> LENGTH: 190
<212> TYPE: DNA
<213> ORGANISM: S. lycopersicum cv. Moneymaker

<400> SEQUENCE: 83

```
taatttggat tggttctgat tgtatatgc ttgttttagt ttcgatggtt tttgagtttt      60
```

-continued

```
tgatgattca ttggcacaaa gtagtgattt ttcagactgt tgggttttgt ggggttcccg      120
tgcttgctct tcactaattt ggattggttc tgatttgtat atgttttagt tttgatggtt      180
tttgagtttt                                                             190

<210> SEQ ID NO 84
<211> LENGTH: 123
<212> TYPE: DNA
<213> ORGANISM: S. lycopersicum cv. Moneymaker

<400> SEQUENCE: 84
gatactcaaa aagaagcttg gtccagatga ccttcgcaca caggtacctt ctgtctcatg       60
cacatgtata caggcacgaa caaatgcact ctcttcccag agtggtgctg tataaagaat      120
tac                                                                    123

<210> SEQ ID NO 85
<211> LENGTH: 229
<212> TYPE: DNA
<213> ORGANISM: S. lycopersicum cv. Moneymaker

<400> SEQUENCE: 85
agctgaggtt tggattactg ggctgaaagc aataattacg aggggacgct ctcgcagagg       60
aaaatatgat gcaagaagtg aaaccatgtt ttcggatagt ccacttggtc aacgagtcac      120
cacatcaact tcatctattg tatgttggca ttttgttgtg ccttcagttg tgtgtgttca      180
ttcttcctct cctctgacct cttccccctc caactgatac aaaatgttg                  229

<210> SEQ ID NO 86
<211> LENGTH: 20
<212> TYPE: DNA
<213> ORGANISM: Artificial Sequence
<220> FEATURE:
<223> OTHER INFORMATION: CD31Rv (primer)

<400> SEQUENCE: 86
atggccagag aaattccaaa                                                   20
```

PARTHENOCARPIC GENETIC ELEMENTS DERIVED FROM *S. HABROCHAITES*

RELATED APPLICATIONS

This application is a continuation of PCT application number PCT/NL2008/050296 designating the United States and filed May 19, 2008; which claims the benefit of U.S. provisional application No. 60/938,904 filed May 18, 2007 and European patent application EP 07108504.7 filed May 18, 2007; all of which are hereby incorporated herein by reference in their entireties.

FIELD OF THE INVENTION

The present application relates to a seedless tomato, methods for obtaining the seedless tomato, as well as to methods for processing the seedless tomato into products, in particular food products.

SUMMARY

Several fruits and vegetables that are currently on the market have the disadvantage that they contain seeds. The presence of these seeds may make the fruit less attractive for many consumers. Also, in the preparation of a variety of products on the basis of these fruits, such as and in particular food products based on tomatoes, the seeds must be removed, for instance by sieving, optionally after prior pureeing, boiling or mashing, which involves further processing steps. This is true for both the preparation of products on industrial scale, such as puree, soups, juices or sauces on the basis of those fruits, as for the household preparation of dishes or food products.

Seedlessness is therefore a very desirable trait in edible fruit with hard seeds such as pineapple, banana, orange, grapefruit, summer squash and melon as well as in fruits that are generally considered vegetables such as tomato, pepper, cucumber and eggplant. Some plants, such as pineapple, produce seedless fruits when a single cultivar is grown because they are self-infertile. Some cucumbers produce seedless fruit if pollinators are excluded. The fact that such plants produce fruits is a result of a trait that is called parthenocarpy. Parthenocarpy (literally meaning virgin fruit) is the natural or artificially induced production of fruit without fertilization of ovules. The fruit is therefore seedless. Parthenocarpy occasionally occurs as a mutation in nature, but it is usually considered a defect, as the plant can no longer sexually reproduce, but may propagate by asexual means. Horticulturists have selected and propagated parthenocarpic cultivars of many plants, including fig, cactus pear (*Opuntia*), breadfruit and eggplant.

However, parthenocarpy of some fruits on a plant may be of value. In some plants, such as seedless watermelon, pollination or other stimulation is required for parthenocarpy. This is termed stimulative parthenocarpy. Banana exhibits stimulative parthenocarpy because it is a triploid-meaning it is the result of a diploid and a tetraploid parent and therefore cannot produce seeds. Plants that do not require pollination or other stimulation to produce parthenocarpic fruit have vegetative parthenocarpy. Cucumber is an example of vegetative parthenocarpy.

When sprayed on flowers, any of the plant hormones, gibberellin, auxin and cytokinin, can often stimulate the development of parthenocarpic fruit. This is termed artificial parthenocarpy. Plant hormones are seldom used commercially to produce parthenocarpic fruit as it may lead to deformed fruits.

In nature, the genotype combination of double recessive parthenocarpy and double recessive functional sterility has no chance of survival (as no seed is formed), so that the genes are not passed on to the next generation.

Some parthenocarpic cultivars have been developed as genetically modified organisms. However, the methods may also involve selective breeding as described later.

The tomato flower consists of an ovary, above which there is a pistil (style plus stigma). Around the pistil there are several stamen (filament plus anther), that produce pollen. In the ovary, there are several pre-embryo's/embryo's which develop (after pollination with the pollen) into seeds.

The tomato plant can be considered as an "obligatory self-pollinator", which means that almost exclusively only its own pollen ends up on the stamen of the flowers of the same plant and thereby pollinates the pre-embryo's. As soon as pollinated pre-embryo's are formed in the ovary, the ovary starts to grow into a tomato (fruit) containing within it, at the same time, the developing seed. In principle no fruit will be formed when no seeds are developing in the ovary (for instance as a result of not-pollinated pre-embryo's).

Literature on seedless tomato (e.g. WO98/24301) mentions the presence in tomato of a gene, called the PK gene, which codes for the property of parthenocarpy. This gene, when present as a double recessive (pk, pk; i.e. the homozygote recessive genotype) supposedly leads to development of fruit (fruit flesh) without concomitant development of seed.

In nature, or in the greenhouse, (the phenotype of) parthenocarpy will only be partial; the factors which are responsible for the absence or partial presence of seeds are present on alleles. In partial parthenocarpy, seeds are formed in (another) part of the fruit, as the result of which the fruit will grow irregularly, which is undesirable. Partial parthenocarpy therefore leads to irregular forms of the fruit, the fruits are deformed.

When a fruit is formed on the basis of total parthenocarpy, no seed is developed within the fruit, with the result that the genes coding for parthenocarpy are not passed over to the next generation, so that the generational line is ended.

Because of this, the gene is extremely rare in nature. Also, (the phenotype of) total parthenocarpy leads to fruits without seed, which makes the production of seed impossible.

The property of parthenocarpy resides in several alleles. The phenotype of total parthenocarpy can only occur when the "mother" (i.e. the tomato plant, the flower of which is pollinated with pollen) as well as the "father" (i.e. the tomato plant that provides the pollen) are both double recessive with regard to the PK gene. This is because, in the fruit "in statu nascendi", there are several developing seeds, at least one of which may not become homozygote recessive if one of the parents is a heterozygote.

Partial parthenocarpy (in the developing tomato, as the result of at least one seed which is not double recessive with regard to the PK gene) makes the fruit develop in a deformed manner.

Besides the PK gene in tomato, a gene is known which codes for the property of functional sterility (FS). A double recessive plant with regard to FS (fs, fs) leads to a tomato plant with a pollen tube that is totally closed, so that the complete and fertile pollen cannot leave the pollen tube, not even by vibrating or other mechanical influences (bumble bees, insects or a vibrator).

The pollen of a tomato plant which has the double recessive (fs, fs) phenotype can only be released by physically opening the pollen tube by hand (by cutting or scissoring), after which—in practice—the pollen has to be removed by hand from the opened pollen tube, i.e. by scraping.

For fertilization of the same or another tomato plant, the pollen then has to be applied to the pistil of the flower, which in practice also must be carried out manually.

In any other "natural" way (i.e. without the above mentioned human intervention) the pollen of a functional sterile flower is not released and therefore not available for fertilization of a pre-embryo. A double recessive, functionally sterile plant (fs, fs) therefore does not fertilize pre-embryo's, which ends the generational line so that the recessive genes for functional sterility are not passed on to the next generation. In nature, with a double recessive phenotype for functional sterility (fs, fs), no fertilization of the pre-embryo's will take place so that no fruit (tomato) will be formed.

WO98/24301 describes that tomatoes without seeds/pips can be produced with advantage using tomato plants which combine the recessive phenotype of parthenocarpy (on the basis of the double recessive gene pk; i.e. pk, pk) with the recessive phenotype of functional sterility (on the basis of the double recessive gene fs; i.e. fs, fs). The absolute seedless fruit can only be produced by physical, human intervention, other than normal selection. The pollen tubes (of the parent) must be opened by hand, after which the pollen must be removed from the open pollen tubes through scraping, and then, also by hand, applied on the pistil of the tomato plant to be fertilized. In particular, the first two of the above mentioned three steps are tedious to perform. The genetic basis or botanical source of the fs and pk genes are not disclosed in WO98/24301.

H. Georgiev et al. (in: Eucarpia Tomato-90, Proceedings of the XI Eucarpia Meeting on Tomato Genetics and Breeding, Malaga, Spain, March 1990: "Breeding of Seedless Tomatoes") describe a method for obtaining tomato plants that carry completely seedless tomato fruits, by combining in one cultivar the homozygous genes for parthenocarpy pat-2 and the homozygous gene for autosterility of flowers ps-2. The pat-2, ps-2 cultivar thus obtained carries completely seedless tomato fruits (as shown in Tables 1 and 2 of the Georgiev reference). Georgiev et al. further describe that by crossing two such cultivars, F1 hybrids can be created that carry completely seedless and standard fruits.

However, extensive research by the applicant of WO98/24301 into the line(s) described by Georgiev has shown that when the property of parthenocarpy and the property of autosterility are combined to provide parent lines, and hybrid seed is obtained from two of these parent lines—i.e. by means of human intervention as described below—that the presence of only the double recessive pat-2 gene and only the double recessive ps-2 gene is in practice not sufficient to provide hybrids that will stably and reliably form seedless tomatoes under all growing conditions. Therefore, crossing two parent lines that both contain only the double recessive genes (pat-2, pat-2) and (ps-2, ps-2) will not lead to commercially acceptable seedless hybrids, as the plants will not always, and not under all circumstances, provide well-formed tomatoes.

There is thus a need for improvements over the teaching of WO 98/24301, in particular there is a need for hybrids (and seed therefor) that allow for reliable production of seedless tomatoes under all environmental conditions, including different light and temperature conditions as may be prevalent in both the tropics as well as moderate climates. This is necessary in order to provide hybrids and seed therefor that can be succesfully commercialized and grown in all countries of the world.

WO00/74468 describes such improvements over WO 98/24301 but also does not disclose a botanical source such as a deposit under the Budapest Treaty of seed of a tomato line comprising a "pk-complex" and an "fs-complex". EP 1428425 discloses such a deposit as a tomato line of which seed was deposited on 5 Dec. 2001 at the American Type Culture Collection (ATCC, Manassas, VA 20110-2209, USA). The deposited seed has been assigned ATCC accession number PTA-3907. ATCC No. PTA-3907 is a plant from a "first F3 generation" that show good expression of the parthenocarpy (based on the pat-2 gene) and functional sterility phenotypes (based on the ps-2 gene), as obtained in the method described in EP1428425. This tomato line is homozygous for a pk/fs complex that contains all the genetic information for strong expression of parthenocarpy by pat-2 and positional sterility by ps-2. Thus, supposedly, starting from ATCC PTA-3907, it is possible to introduce strong expression of parthenocarpy and positional sterility into any desired tomato variety by crossing ATCC PTA-3907 with a desired non-seedless parent and subsequent repeated selfing by manual self-pollination.

However, despite the availability of the ATCC PTA-3907 deposit providing the genetic source, the genetics of parthenocarpy is unknown at present. Yet, knowledge of the chromosomal location of the trait and methods for tracking the presence of the trait in plants and crosses between plants would be very valuable in increasing the production of parthenocarpic plants. In fact, EP1428425 mentioned that extensive research over a period of more than 10 years could not provide a satisfactory model that might clarify the number and/or the character of the genes, alleles or other genetic factors that are necessary to make up a pk, fs complex contained in the ATCC No. PTA-3907 deposit, or that might even explain the very low occurrence or sometimes even the complete absence of seedless (or even functionally sterile) phenotypes in the F1, F2, F3 and even F4 obtained from the original seedless and non seedless parents. EP 1428425 mentions that this shows that the factors determining the true seedless phenotype of the invention are much more intricate than suggested in the above prior art (i.e. not determined by a combination of (1 +1), (2 +1) or even (3 +1) separate genes), and also explains why the prior art was not able to provide tomato plants or lines that can be used to produce seedless hybrids in a stable and reliable manner and under all environmental conditions.

The object of the present invention is to solve the above mentioned problems. It is an aim of the present invention to provide for a method of producing parthenocarpic plants. It is another aim of the present invention to provide more insight into the genetic basis of parthenocapry. In particular, it is an aim of the present invention to provide for genomic markers with which the presence of a parthenocarpy-conferring genetic elements in plants can be succesfully monitored during breeding and selection processes, in particular in production of commercial varieties of vegetable and fruit plants.

SUMMARY OF THE INVENTION

The present inventors have discovered that certain introgression lines produced by an interspecific cross between *Solanum habrochaites* LYC4/78 as the donor, and *Solanum lycopersicum* cv. Moneymaker as the recurrent parent plants, failed to set seed while at the same time these plants exhibited increased fruit weight and it was discovered that these plants exhibited a total parthenocarpic phenotype. The interspecific cross was described previously in WO2006/046861 of applicant. The total parthenocarpic phenotype was exhibited by a plant selected to be homozygous donor parent (*Solanum habrochaites* LYC4/78) for an introgression on chromosome 5 and this line was denoted IL5-1. This line is also referred to herein as DRS5.1. A representative sample of seed of

*Solanum habrochaites* LYC4/78 was deposited with the NCIMB on 13 Nov. 2007 under accession number NCIMB 41517 within the meaning of Rule 6.1(iv) of the Budapest Treaty.

In order to maintain IL line DRS5.1 as well as another IL line containing an introgression on chromosome 5 (line IL5-2 as described herein that also failed to set seed, but did not exhibit increased fruit weight, yet produced acceptable sized-fruits) it had to be kept in its heterozygous state. It was found upon morphological examination that these plants were functional sterile (long styles, short filaments).

Also, one line having an introgression on chromosome 12 exhibited seedless fruits of acceptable size and could be regarded as parthenocarpic. Also this line contained a heterozygous introgression on chromosome 4. By careful analysis, the present inventors discovered that introgressions from *S. habrochaites* could give rise to a parthenocarpic phenotype in commercial tomato varieties of *S. lycopersicum*.

In a first aspect, the present invention provides a method of producing a parthenocarpic, and optionally male sterile, tomato plant comprising introgressing into said plant a genetic region from Chromosome 4, 5 and/or 12 of *S. habrochaites* LYC4/78, a representative sample of seed of which was deposited on 13 Nov. 2007 with the NCIMB under Accession number 41517,
  wherein the genetic region from Chromosome 4 of *S. habrochaites* LYC4/78 is a region between Marker CD59 and TG272, and
  wherein the genetic region from Chromosome 5 of *S. habrochaites* LYC4/78 is a region between COS Marker T1181 and RFLP Marker CD31(A).

In a preferred embodiment of a method of the invention, the genetic region from Chromosome 4 of *S. habrochaites* LYC4/78 includes at least one marker selected from Marker CD59, RFLP Marker CT229, and COS Marker T1068.

In another preferred embodiment of a method of the invention, the genetic region from Chromosome 5 of *S. habrochaites* LYC4/78 includes at least one marker selected from COS Marker T1181, RFLP Marker TG441 and/or RFLP Marker CD31(A).

Parthenocarpic tomato plants as described herein are optionally (and preferably) male sterile.

In a preferred embodiment the genetic region from Chromosome 4 of *S. habrochaites* LYC4/78 does not include markers TG272, TG264, TG62, T1405, and/or CT50.

In another preferred embodiment the genetic region from Chromosome 5 of *S. habrochaites* LYC4/78 does not include RFLP Marker TG318 or more downstream markers such as TG538, TG60, and/or CT138.

The skilled person will understand that any combination of genetic regions defined herein may be introgressed in a tomato plant in order to render that plant parthenocarpic, such as regions defined herein from chromosomes 4, 5 and 12 of *S. habrochaites* LYC4/78, regions defined herein from chromosomes 4 and 5, or 5 and 12, or 4 and 12.

The genetic region from Chromosome 12 of *S. habrochaites* LYC4/78 in one preferred embodiment is essentially as displayed in FIG. 3. Preferably this regions does not include RFLP Marker TG296 (96.00 cM) as located on the Tomato-EXPEN 2000 Map of *S. lycopersicum* LA925 x *S. pennellii* LA716 type F2. In particular, the genetic region of preference is as shown by the dark region in FIG. 1.

In another aspect, the present invention relates to a method of selecting a parthenocarpic (and optionally male sterile) tomato plant comprising crossing a seed-bearing tomato plant with a plant of *S. habrochaites* LYC4/78 and selecting a seed or a plant grown from said seed for the presence of an introgression of a genetic region of Chromosome 4, 5 and/or 12 of *S. habrochaites* LYC4/78,
  wherein the genetic region from Chromosome 4 of *S. habrochaites* LYC4/78 includes at least one marker selected from Marker CD59, RFLP Marker CT229, and COS Marker T1068, and
  wherein the genetic region from Chromosome 5 of *S. habrochaites* LYC4/78 includes at least one marker selected from COS Marker T1181, RFLP Marker TG441 and/or RFLP Marker CD31(A).

The preferred embodiments described above for the aspect of producing the partenocarpic plant are also applicable to the present method of selecting a plant.

In a preferred embodiment of a method of producing or selecting a parthenocarpic plant, said parthenocarpic plant is a *Solanum lycopersicum* plant, more preferably a cultivated plant of *Solanum lycopersicum*. Said plant is preferably not *Solanum lycopersicum* cv. Moneymaker.

In another aspect, the present invention relates to a tomato plant, or part thereof, obtainable by a method as described above for producing a plant or selected by a method as described above.

In another aspect, the present invention relates to a method of producing a parthenocarpic inbred tomato plant, comprising
a) producing a parthenocarpic tomato plant by a method of producing a parthenocarpic plant by introgressing genetic regions from *S. habrochaites* LYC 4/78 as described above;
b) crossing said parthenocarpic tomato plant with itself or another tomato plant to yield progeny tomato seed;
c) growing said progeny tomato seed of step to yield additional parthenocarpic tomato plants;
d) repeating the crossing and growing steps from 0 to 7 times to generate a parthenocarpic resistant inbred tomato plant.

In a preferred embodiment of said method, said step c) further comprises the step of identifying plants that exhibit a parthenocarpic phenotype and possess commercially desirable characteristics.

In another preferred embodiment of said method, said method further comprises the step of selecting homozygote inbred tomato plants.

In another aspect, the present invention relates to a parthenocarpic inbred tomato plant, or parts thereof, obtainable by a method of the present invention.

In another aspect, the present invention relates to a hybrid tomato plant, or parts thereof, that exhibits a parthenocarpic phenotype, wherein said hybrid tomato plant is obtainable by crossing a parthenocarpic inbred tomato plant obtainable by a method of the present invention with an inbred tomato plant that exhibits commercially desirable characteristics.

In another aspect, the present invention relates to a tissue culture of regenerable cells of the tomato plants as defined herein above, preferably said regenerable cells comprise cells or protoplasts isolated from a tissue selected from the group consisting of leaves, pollen, embryos, roots, root tips, anthers, flowers, fruits, and stems and seeds.

In another aspect, the present invention relates to the use of a genetic marker selected from the group consisting of the genetic markers of Tables 30, 31 or 32 for the detection of parthenocarpic genetic elements derived from *S. habrochaites* LYC4/78, and/or for the detection of parthenocarpic tomato plants.

Suitable markers include fragments of the markers as described herein, for instance fragments harboring characterizing nucleotide polymorphisms between *S. habrochaites*

Lyc4/78 and *S. lycopersicum* cv. Moneymaker as indicated in Table 32. The skilled person is well aware how such polymorphisms can be detected.

In another aspect, the present invention relates to a parthenocarpic plant comprising an introgression from *S. habrochaites* LYC4/78 defined as parthenocarpic genetic elements derived as described above. In a preferred embodiment of said aspect said plant is a plant of the species *S. lycopersicum*, more preferably said plant is not a plant of the cultivar *S. lycopersicum* cv. Moneymaker.

The selection by markers can suitably be adapted to the selection of donor (*S. habrochaites* LYC4/78) or recipient—specific (e.g. *S. lycopersicon* cv. Moneymaker) nucleotide polymorphisms as indicated in Table 32, wherein polymorphisms are indicated by the base variation given as the [*S. habrochaites* LYC4/78 position/*S. lycopersicon* cv. Moneymaker].

DETAILED DESCRIPTION OF THE INVENTION

Definitions

Figure 1:
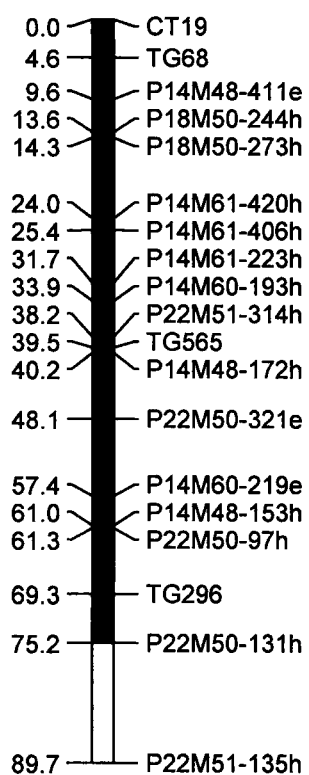
FIG. 1 shows the genetic map of Chromosome 12 of tomato indicating the marker positions as referred to herein.

As used herein, the term "parthenocarpy" refers to the production of seedless fruit which develop in absence of pollination and/or fertilization. Unless otherwise indicated, the term refers to genetic parthenocarpy. Unless otherwise indicated, the term refers to total parthenocarpy, meaning that the fruits are entirely seedless and non-deformed but having a normal regular shape. Parthenocarpic plants can no longer sexually reproduce, but may propagate by asexual means. In particular, the term "parthenocarpic", or the related term "parthenocarpy", is used herein to define a phenotype of a plant wherein the plant produces seedless fruits that are otherwise of normal size. A seedless plant that produces considerably smaller fruits is not considered parthenocarpic as the term is used herein. A plant having poor seed set is not necessarily parthenocarpic. In fact, the term refers to plants being entirely seedless. In the present description the term "parthenocarpic plant" refers to a plant comprising the genetic element from *S. habrochaites* LYC4/78, as defined herein, and which produces seedless fruits which are essentially equal in size to the original recipient parent and non-deformed.

As used herein, the term "allele(s)" means any of one or more alternative forms of a gene, all of which alleles relate to at least one trait or characteristic. In a diploid cell or organism, the two alleles of a given gene occupy corresponding loci on a pair of homologous chromosomes. Since the present invention relates to QTLs, i.e. genomic regions that may comprise one or more genes, but also regulatory sequences, it is in some instances more accurate to refer to "haplotype" (i.e. an allele of a chromosomal segment) in stead of "allele", however, in those instances, the term "allele" should be understood to comprise the term "haplotype".

A "gene" is defined herein as a hereditary unit consisting of a sequence of DNA that occupies a specific location on a chromosome and that contains the genetic instruction for a particular characteristics or trait in an organism.

A "locus" is defined herein as the position that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hybrid" means any offspring of a cross between two genetically unlike individuals, including but not limited to the cross between two inbred lines.

As used herein, the term "inbred" means a substantially homozygous individual or line In this application a "recombination event" is understood to mean a meiotic crossing-over.

As used herein, the terms "introgression", "introgressed" and "introgressing" refer to both a natural and artificial process whereby genes of one species, variety or cultivar are moved into the genome of another species, variety or cultivar, by crossing those species. The process may optionally be completed by backcrossing to the recurrent parent.

"Genetic engineering", "transformation" and "genetic modification" are all used herein as synonyms for the transfer of isolated and cloned genes into the DNA, usually the chromosomal DNA or genome, of another organism.

As used herein, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

As used herein, the term "plant part" indicates a part of the tomato plant, including single cells and cell tissues such as plant cells that are intact in plants, cell clumps and tissue cultures from which tomato plants can be regenerated. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "tomato" means any plant, line or population formerly known under the genus name of *Lycopersicon* including but not limited to *Lycopersicon cerasi-*

*forme, Lycopersicon cheesmanii, Lycopersicon chilense, Lycopersicon chmielewskii, Lycopersicon esculentum* (now *Solanum lycopersicum*), *Lycopersicon hirsutum, Lycopersicon parviflorum, Lycopersicon pennellii, Lycopersicon peruvianum, Lycopersicon pimpinellifolium,* or *Solanum lycopersicoides*. The newly proposed scientific name for *Lycopersicon esculentum* is *Solanum lycopersicum*. Similarly, the names of the wild species may be altered. *L. pennellii* has become *Solanum pennellii*, *L. hirsutum* may become *S. habrochaites, L. peruvianum* may be split into *S. 'N. peruvianum'* and *S. 'Callejon de Huayles', S. peruvianum,* and *S. corneliomuelleri, L. parviflorum* may become *S. neorickii, L. chmielewskii* may become *S. chmielewskii, L. chilense* may become *S. chilense, L. cheesmaniae* may become *S. cheesmaniae* or *S. galapagense,* and *L. pimpinellifolium* may become *S. pimpinellifolium* (Solanacea Genome Network (2005) Spooner and Knapp).

It is especially noted that *S. habrochaites* can be defined as a tomato species that carries hairy fruits, while *S. lycopersicum* is a tomato species carrying hairless fruits.

As used herein, the term "variety" or "cultivar" means a group of similar plants that by structural or genetic features and/or performance can be distinguished from other varieties within the same species.

A "cultivated plant" is defined herein as a plant exhibiting agronomically desirable characteristics. The term is used in contrast to the term "wild", which indicates a variety that is of no immediate commercial interest due to undesirable traits. *S. habrochaites* can be defined as a tomato species that is of no immediate commercial interest due to undesirable traits (hairy fruits).

A genetic region conferring parthenocarpy derived from *S. habrochaites* as defined herein is claimed in plants wherein the region is not in its genetic background. The term "natural genetic background" is used herein to indicate the original genetic background of the genetic element. Such a background may for instance be the genome of a seed-bearing wild accession of tomato. For instance, the parthenocarpy-conferring genetic elements of the present invention were found at specific locations on chromosomes 4, 5 and/or 12 of *Solanum habrochaites* LYC 4/78. As an example, the *Solanum habrochaites* LYC 4/78 represents the natural genetic background of the QTLs on chromosomes 4, 5 and/or 12 of *Solanum habrochaites* LYC 4/78. A a method that involves the transfer of DNA comprising the parthenocarpy-conferring genetic element, or a parthenocarpy-conferring part thereof, from chromosomes 4 of *Solanum habrochaites* LYC 4/78 to the same position on chromosome 4 of another tomato species, most notably *S. lycopersicum*, will result in that parthenocarpy-conferring genetic elements, or said parthenocarpy-conferring genetic part thereof, not being in its natural genetic background.

The term "functional sterile" is used herein in its art-recognized meaning. Functional sterility is considered a form of a more general property of that occurs in tomato called autosterility, which can occur in two types, i.e:

male sterile: self pollination is not possible because of the absence of viable pollen (ms) or degenerated stamens (s1, stamenless). When male sterility were to be introduced in a commercial seed hybrid tomato (seed), the grower has to sow double the amount of seed and to remove before planting the 50% of heterozygous ms pk plants, recognizable by a marker gene for ms. This is not fully possible by overcrossing problems.

functional sterile; viable pollen is present but cannot reach the pistil due to some morphological deviation of the flowers. Functional sterility (fs) itself can also be distinguished in four different types, i.e.:

ps-type: an exerted style phenomenon as a result of strong twisting and shorting of the stamens; this property generally provides for easy self pollination and lower receptivity of the style, which makes it not very suitable for hybrid seed production;

ps-2-type: a non opening anther bags type successfully used in hybrid seed production;

ex-type: exerted style over the stamens easy self pollination and low receptivity of the sigma make it less suitable for hybrid seed production; and short style-type: the stigma is located below the anthers, the main disadvantage is its high level of self pollination.

Hybrids are the product of a cross between genetically unlike parents. The development of hybrids in a plant breeding program requires, in general, the development of homozygous inbred lines, the crossing of these lines, and the evaluation of the crosses. Most plant breeding programs combine the genetic backgrounds from two or more inbred lines or various other broad-based sources into breeding pools from which new inbred lines are developed by selfing and selection of desired phenotypes. Hybrids can also be used as a source of plant breeding material or as source populations from which to develop or derive new plant lines. The expression of a trait in a hybrid may exceed the midpoint of the amount expressed by the two parents, which is known as hybrid vigor.

Plant breeding techniques known in the art include, but are not limited to, recurrent selection, pedigree breeding, restriction length polymorphism enhanced selection, genetic marker enhanced selection and transformation. Inbred lines may for instance be derived from hybrids by using said methods as pedigree breeding and recurrent selection breeding. Newly developed inbreds are crossed with other inbred lines and the hybrids from these crosses are evaluated to determine which of those have commercial potential.

Pedigree breeding is a system of breeding in which individual plants are selected in the segregating generations from a cross on the basis of their desirability judged individually and on the basis of a pedigree record.

Recurrent selection is a breeding method based upon intercrossing selected individuals followed by continuing cycles of selection and intercrossing to increase the frequency of desired alleles in the population.

Recurrent selection may for instance be performed by backcross breeding, which involves system of breeding whereby recurrent backcrosses are made to one of the parents of a hybrid, accompanied by selection for a specific character or characters. The backcross being the cross of a hybrid to either of its parents. Backcrossing can for instance be used to transfer a specific desirable trait that is present in a donor plant line to another, superior plant line (e.g. an inbred line) that lacks that trait. The first step of this process involves crossing the superior plant line (recurrent parent) to a donor plant line (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait and for the germplasm inherited from the recurrent parent, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

A general description of breeding methods commonly used for acquiring different traits in various crops, including tomato, can be found in reference books such as e.g., Allard, R. W. (1960) *Principles of Plant Breeding*; Simmonds, N. W. (1979) *Principles of Crop Improvement*; Sneep, J. et al., (1979) *Tomato Breeding* (p. 135-171) in: *Breeding of Vegetable Crops*, Mark J. Basset, (1986, editor), *The Tomato crop: a scientific basis for improvement*, by Atherton, J. G. & J. Rudich, (1986, editors); *Plant Breeding Perspectives*; Fehr, (1987) *Principles of Cultivar Development Theory and Technique*).

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant. Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Tomato (*Lycopersicon esculentum* L. or garden tomato) belongs to the Solanaceae (nightshade) family, genus *Solanum*, subgenus *Lycopersicon*. Other important solanaceae include potato (*Solanum tuberosum*) and aubergine or eggplant (*Solanum melongena*). All varieties in the species *L. esculentum* are self-pollinating. Most other species in the subgenus *Lycopersicon*, such as *L. pimpinellifolium* (currant tomato), *L. hirsutum* (hairy tomato) and *L. peruvianum* (Peruvian tomato), are cross-pollinating. Preferably, inbred breeder lines of *L. esculentum* are therefore male sterile in order to prevent genetic changes due to undesired self pollination. Advantageously costs of seed production are reduced in such male sterile plants.

The development of a hybrid tomato variety in a tomato plant breeding program generally involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with unrelated inbred lines or wild species of tomato to produce the hybrid progeny (F1). During the inbreeding process in tomato, the vigor of the lines generally decreases. Vigor is restored when an inbred line is crossed with another tomato plant (e.g. another inbred or wild variety) to produce the hybrid progeny (F1). An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid tomato plants can then be generated from this hybrid seed supply.

There are many important factors to be considered in the art of plant breeding, such as the ability to recognize important morphological and physiological characteristics, the ability to design evaluation techniques for genotypic and phenotypic traits of interest, and the ability to search out and exploit the genes for the desired traits in new or improved combinations.

The objective of commercial tomato hybrid line development resulting from a tomato plant breeding program is to develop new inbred lines to produce hybrids that combine to produce high yields and superior agronomic performance. Even though the primary trait breeders seek is yield, many other major agronomic traits are of importance in hybrid combination and have an impact on yield or otherwise provide superior performance in hybrid combinations. Such traits include high crop potential, resistance to diseases including insect pests, resistance to stress such as drought and heat stress, and flavor, color shape and shelf life of the tomato fruits. In addition, the lines per se must have acceptable performance for parental traits such as seed yields and pollen production, which affect ability to provide parental lines in sufficient quantity and quality for hybridization. These traits have been shown to be under genetic control and many if not all of the traits are affected by multiple genes.

For the production of the hybrid tomato plant, any inbred *Lycopersicon esculentum* line may be developed by conventional breeding methods, comprising continuous selfing and selection of various breeding lines to combine the genes of these lines in a homozygous line. Pedigree selection based on resistance against soil-borne pathogens and root and stem diseases, large size, firmness and color of the fruit as well as favourable root and stem development may then be applied for a number of subsequent generations to yield the mentioned inbred parent line. The inbred line is then preferably self-pollinated and planted for a sufficient number of generations to ensure the uniformity and phenotypic stability of its traits characteristic of its homozygous genotype. When no variant traits are observed, the features are stable.

Within *Solanum*, ILs have been developed for *Solanum pennellii* LA716 (Eshed et al. 1994), *S. habrochaites* LA1777 (Monforte et al. 2000a) and *Solanum lycopersicoides* LA2951 (Canady et al. 2005). Such populations have shown to be extremely helpful in the identification of quantitative traits (Eshed et al. 1995; Rousseaux et al. 2005), fine mapping of QTLs (Fridman et al. 2004; Monforte et al. 2001; Monforte et al. 2000b) and QTL cloning (Frary et al. 2000; Fridman et al. 2000; Ku et al. 2001).

Currently, one *S. habrochaites* LA1777 IL population exists in a determinate growing *S. lycopersicum* E6203 (Monforte et al. 2000a).

Herein we describe the development of a second IL population of *S. habrochaites*, now based on introgressions from *S. habrochaites* LYC 4/78 in the background of the indeterminate growing cultivated tomato *S. lycopersicum* cv. Moneymaker, and the use of the lines in the production of seedless, parthenocarpic tomato plants.

The plants of the present invention are preferably male sterile. Male sterility may be present in a certain cross, such as the functional male sterlity found in line DRS 5.1. Alternatively, male sterility may be introduced by using lines that contain the ps-2 gene that confers functional male sterility as donor plants, and introgressing the gene into the desired plant line.

Functional male sterility is an important trait for the production of hybrid seeds. Among the genes coding for functional male sterility in tomato is the positional sterility gene ps-2. ps-2 is monogenic recessive, confers non-dehiscent anthers and is the most suitable for practical uses. Markers for molecular-assisted selection (MAS) have been developed (Gorguet et al., 2006. Theor. Appl. Genet, 113(8):1437-1448. This was done in an F2 segregating population derived from the interspecific cross between a functionally male sterile line (ps-2/ps-2; *Solanum lycopersicum*) and a functionally male fertile line (*S. pimpinellifolium*). The ps-2 locus was found to reside in a 1.65 cM interval delimited by markers T0958 and T0635 on the short arm of Chromosome 4. This region also contains many COS markers, which may be useful in MAS.

A method of the present invention may make use of a method for producing a seedless plant, for instance as described in detail in EP1428425, wherein an fs/pk-complex plant may be produced by a method comprises the following steps, further discussed therebelow:
a. Crossing an "original seedless parent" as defined herein with a "original non seedless parent" as defined herein to provide a non-seedless F1 generation;
b. Self-pollinating the F1 generation thus obtained to provide a further generation, herein referred to as the F2 generation.
c1. Selecting any plant(s) of the F2 thus obtained with a seedless phenotype and causing these seedless plants to self-pollinate, to provide a first F3 generation; as well as
c2. Selecting any plants of the F2 thus obtained with a functionally sterile phenotype, and causing these plants to self-pollinate in order to provide a second F3 generation;
d. Selecting any plants of the first or second F3 generation with a seedless phenotype;
e. Causing the plants of the first or second F3 generation with a seedless phenotype to self-pollinate in order to provide an F4 generation
f. Causing the plants of the F4 generation thus obtained which have a seedless phenotype to self-pollinate in order to provide an F5 generation; and optionally causing the plants of the F5 generation thus obtained which have a seedless phenotype to self-pollinate in order to provide an F6 generation.

It was reported in EP1428425 that usually, by the F5 generation, and in particular by the F6 generation obtained in step e), the pk,fs complex in the plants thus obtained will have sufficiently stabilized, i.e. become "fixated", for the tomato plant to be used as a pk,fs parent in the invention, or to be used as a starting plant or line for obtaining other (lines of) pk,fs parents, i.e. by crossing in further properties or by means of backcrosses. As the F3, F4, F5, F6 and further generations have a seedless phenotype- or in the case of the "second F3 generation" at least a functionally sterile phenotype—obtaining the F4, F5, F6 and further generations, as well as maintaining the pk,fs parent lines for production of the seedless hybrids, will require human intervention as defined hereinbelow. This requirement for human intervention to provide a further generation is also generally referred to herein as "causing self-pollination". It was reported in EP1428425 that the F2 will usually only contain at most about 1 or 2 seedless plants in 100 F2 plants, but may also provide no seedless plants, depending upon the original seedless parent and in particular the original non-seedless parent used. Even when seedless F2 plants are obtained, it was found that the amount thereof (i.e. 1-5%) is significantly less than the 8.25% (i.e. 1 plant out of 16) that was to be expected according to Mendelian principles if the presence of double recessive pat-2 and ps-2 genes by itself were sufficient to provide a seedless phenotype. This shows that the cross with the original non-seedless parent apparently introduces some—probably dominant—genes, alleles or other genetic factors that negatively influence the occurrence of the seedless phenotype in the F2. The F2 was found to usually contain some functionally sterile plants, i.e. usually about 10-15 plants out of 100, again depending upon the original seedless parent and in particular the original non-seedless parent. This again is less than the 25% that was to be expected according to Mendelian principles if the presence of double recessive ps-2 by itself were sufficient to provide a functionally sterile phenotype. This shows that also the presence of the desired functionally sterile phenotype is determined by a complex of genetic factors.

The method described in EP1428425 further involves that the seedless plants from the F2 are selected and caused to self-pollinate, so as to provide an F3, herein referred to as the "first F3 generation". It was reported that, despite the seedless phenotype of the F2 plant, sometimes not all F3 plants thus obtained will show the seedless phenotype of the F2 plant, but can form 0-100%, and more often form only about 10-20% of the F3 plants. This supposedly confirmed that the seedless phenotype in this F2 plants is caused by a complex of genes (i.e. the pk,fs complex of the invention), and not by homozygote recessive pat-2 and ps-2 genes alone, as in the original seedless parent. It supposedly also showed that in the F2, the pk,fs complex is not fixated enough—i.e. genetically not homogenous enough—to provide completely seedless offspring.

Because of this, the seedless F2 plants obtained as above were also not suited for use as a pk, fs parent in the invention described in EP1428425. The plants of the first F3 generation that show the seedless phenotype were selected, and caused to self-pollinate so as to provide an F4. Again, it was usually found that not all F4 plants obtained from the seedless F3 plants will show the seedless phenotype: the amount of seedless F4 plants may vary from 0-100%, and is usually about 10-20% of all F4 plants. Also, not all F4 plants were found to be seedless under all environmental conditions. This again supposedly showed that the pk,fs complex has not yet become sufficiently fixated in these F3 of F4 plants for them to be used as pk,fs parents in the invention described in EP1428425. The seedless plants from the F4 were then again caused to self-pollinate to provide an F5, and said the seedless plants from the F5 were caused to self-pollinate to produce an F6. Again, in the F5 and sometimes also in the F6, some non-seedless plants were obtained because supposedly the pk,fs complex was not yet sufficiently fixated in the seedless F4 or F5, respectively. Usually, by the F6 generation, the pk,fs complex in the seedless F6 plants was considered to be sufficiently stable, so that all seedless F6 plants exclusively provide seedless F7 plants when caused to self-pollinate. This also supposedly indicated that the F6 inbreds thus obtained could be used as pk, fs parents in the invention described in EP1428425. If the F7 still provided some non-seedless plants, the F7 may again be caused to self-pollinate to provide an F8, etc., until a generation is obtained in which the pk, fs complex is sufficiently fixated. However, this is usually not required and also not preferred. Also, if by the F9 and in particular by the F10 generation, the pk, fs complex has still not become sufficiently fixated, it will usually be assumed that this inbred line cannot be used as an pk, fs parent line in the invention described in EP 1428425.

Generally, only a small amount of the seedless F2 plants will "make it" to the F6, depending upon the original seedless parent but in particular the original non-seedless parent used. Also, in generating the F6, some selection pressure may be applied in order to test the stability and reliability of the seedless phenotype under all environmental conditions. For instance, factors such as light, temperature can be used to "test" and/or fixate the stability of the seedless phenotype of the F3, F4, F5 or F6. Besides the seedless F2 plants, also the F2 plants that only show a phenotype of functional sterility are caused to self-pollinate, so as to provide an F3 generation, herein referred to as the "second F3 generation". This second F3 generation will usually comprise essentially all functionally sterile plants, and may comprise some seedless plants, i.e. about 1-3 out of 40 F3 plants (which can be easily recognized and selected because they are the only ones in this second F3 that will grow fruits). If so, these seedless F3 plants are caused to self-pollinate to provide an F4, followed by an F5 and F6, and optionally an F7 and F8, etc., essentially as described for the first F3 generation. Again, not all seedless plants of the second F3 generation will make it to the F6, again depending upon the original seedless parent and in particular the original non-seedless parent used.

In the above methodology, for a given combination of original seedless parent and original non-seedless parent, it is possible that no seedless plants are obtained in the F2, and only few functionally sterile plants. These functionally sterile F2 plants are then caused to self-pollinate. However, if in the F3 thus obtained, again no seedless plants are found, it will usually be assumed that this particular combination of original seedless parent and original non-seedless parent cannot be used to provide a pk, fs parent according to the invention. A possible explanation for this may be that the original non-seedless parent used did not contain all genetic factors (i.e. genes, alleles or other factors) necessary to "complete" the pk, fs complex, relative to the genes already present in the original seedless parent used.

The invention therefore in further aspects relates to cultivation material for tomatoes such as seed or seedlings (optionally in a container), as well as seedless tomatoes obtained and/or obtainable as described hereinabove, and/or suited for use in the method(s) described herein.

The parthenocarpic tomatoes according to the invention can also be processed further in a manner known per se to tomato products, in particular food products, which may or may not be in a form ready or suited for final use. In this respect, the tomatoes according to the invention have the advantage that they can be processed directly, without a further step for removing the seeds/pips in the production process.

The invention in a further aspect therefore relates to products, in particular food products, obtained from the seedless tomatoes according to the invention, as well as to a method for obtaining said food products, in which the tomatoes are processed to these products without a separate step for removing the seeds. Such a method can therefore—inter alia—comprise pureeing or mashing in another way of the tomatoes, optionally followed by incorporating or adding further desired ingredients, and packaging the tomato product thus obtained, without seeds or the residues thereof, in suitable containers for storage, transport or sale, in which said method does not comprise a step for removing any pips/seeds between the mashing of the tomatoes and the packaging of the product.

The genetic elements as disclosed herein provide male sterility as a result of which fertilization of the seed set is absent.

The methods and plants of the present invention are in addition to being parthenocarpic also preferable male sterile, most preferably functionally sterile, such as positionally sterile. Moreover, the genetic elements as disclosed herein provide for parthenocarpy, the phenomenon whereby fruit set occurs without fertilization.

In addition to providing parthenocarpy and/or male sterility, the genetic alements as disclosed herein provide for an increase in fruit yield. An advantage of the parhtenocarpic plants of the invention is that they produce fruits having a higher content of fruit flesh (expressed as dry weight) compared to non-seedless tomatoes harvested at a corresponding time, i.e. 1, 2, 5, 10, 25, or 35%, or more, based on total weight of the tomato (i.e. on average about 5.5 to 6.5 gram dry matter for the seedless tomatoes compared to about 4.5 to 5.5 gram dry matter for non-seedless tomatoes, on a total weight at harvest of about 110-120 gram). In terms of dry matter yield, this means an increase of at least about 20% (in which furthermore the dry matter of the non-seedless tomatoes will still include the pips).

By using male sterility, the skilled person can now discover parthenocarpy in plants. Normally, parthenocarpy can remain undetected (is masked) when seed set does occur. This hidden parthenocarpy can be found by crossing descendants of a cross between a parthenocarpic plant and a plant having hidden parthenocarpy and testing the cross for fruit set without seed.

Preferably, the introgressions as defined herein are present in homozygous form.

The present invention now also provides for the possibility of providing a method to clone gene(s) that are responsible for the parthenocarpic phenotype derived from *S. habrochaites* LYC4/78.

EXAMPLES

Example 1

In order to make for a more effective breeding process, involving the selection of candidate parent plants having the proper genetic constitution, it is necessary to have at one's disposal one or more genetic markers that indicate the presence of that genetic constitution in at least one of the candidate parent plants. This process, which includes crossing of the selected plants and is termed marker assisted selection (MAS), efficiently transfers favourable parental alleles from a donor to a recipient population and ensures that breeding is no longer dependent on coincidence and is economically much more effective in terms of development costs.

Material & Methods

Plant Material and Development of the ILs

Seeds of *Solanum habrochaites* LYC 4/78 (hereafter referred as LYC 4/78; seed batch of 1978) were obtained from the gene bank located at the Institute for Plant Genetics and Crop Plant Research, Gatersleben, Germany.

Seeds of *Solanum lycopersicum* cv. Moneymaker (hereafter referred as Moneymaker) were obtained from the seed bank of De Ruiter Seeds R&D BV, Bergschenhoek, The Netherlands.

Figure 2:
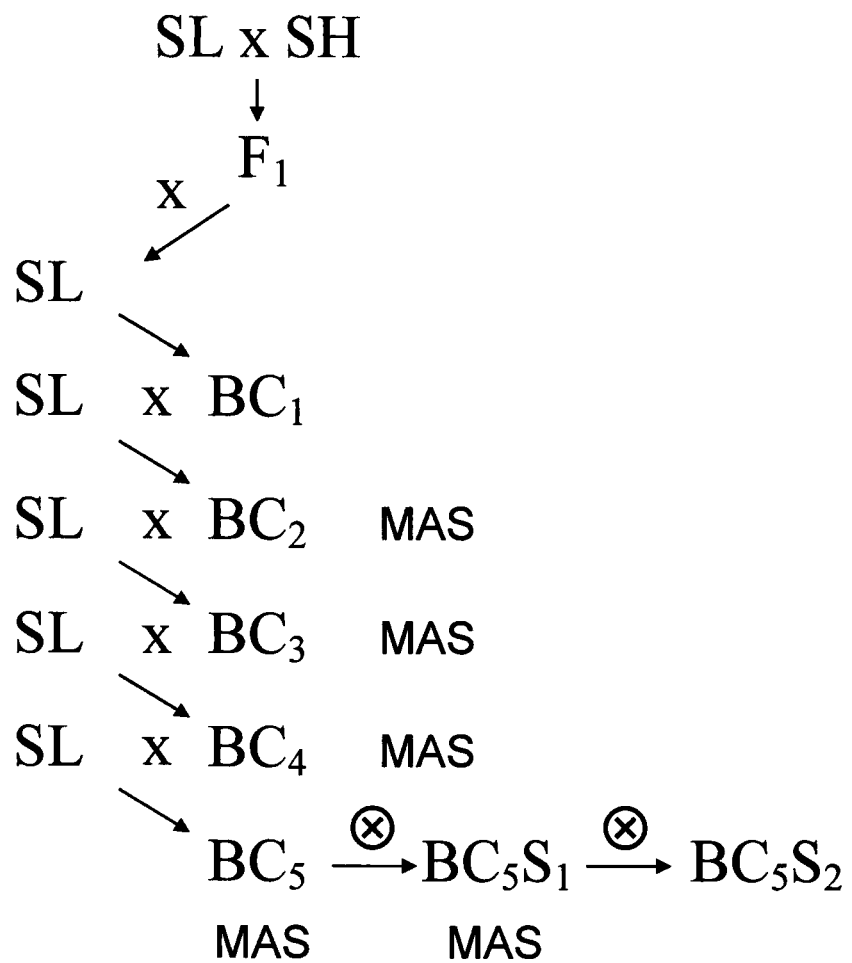
FIG. 2 shows the crossing scheme for the development of an introgression line (IL) population of *S. habrochaites* LYC 4/78 (SH) in the genetic background of *S. lycopersicum* cv. Moneymaker (SL). Using MAS, $BC_2$, $BC_3$, and $BC_4$ genotypes were selected containing one of the two identified parthenocarpy-conferring genetic elements and some $BC_2$ were self pollinated to produce $BC_2S_1$ seeds.
Figure 3:
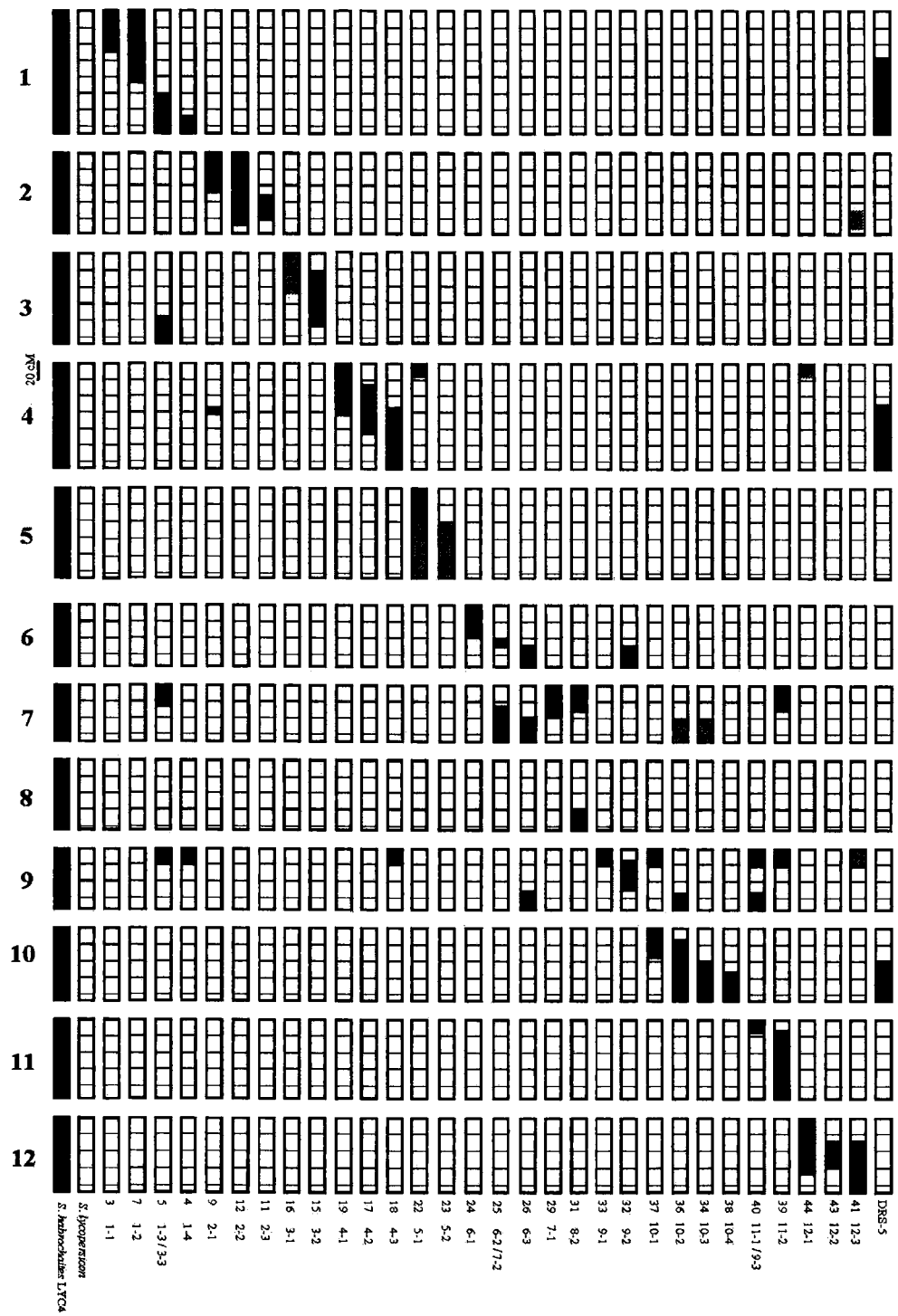
FIG. 3 shows the core set of 30 ILs as described in the Examples. This core set represents the maximum coverage of the SH genome in as few as possible ILs (line indications given at the bottom. The core set consists of 15 ILs harboring a single introgression, 10 ILs containing two introgressions, 4 ILs containing three introgressions while one IL still contained four homozygous introgressions. All 12 chromosomes are indicated with reference to the *S. habrochaites* LYC4, *S. lycopersocon* and reference DRS5.
Figure 4:
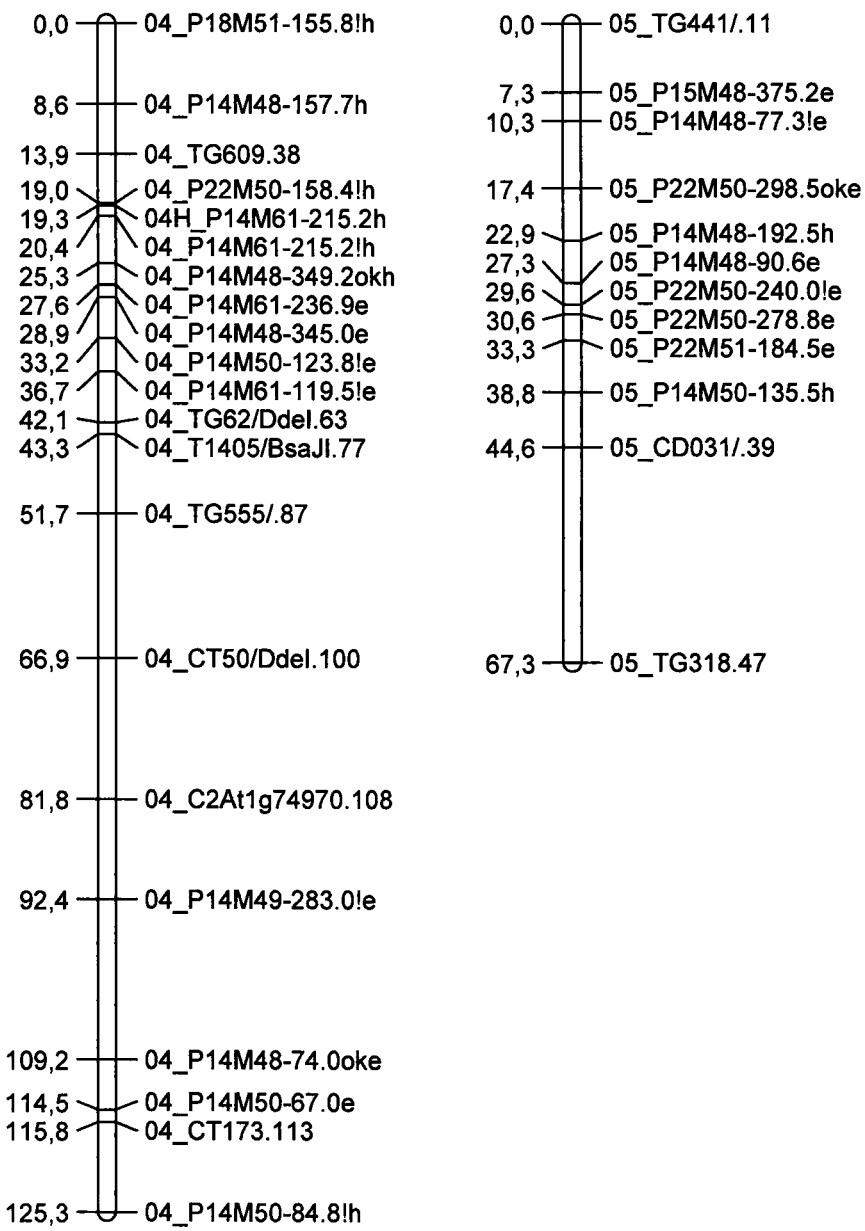
FIG. 4 shows the genetic map of Chromosomes 4 and 5 of tomato indicating the marker positions as referred to herein.

An interspecific cross between Moneymaker and LYC 4/78 was made to produce $F_1$ seeds. The $F_1$ seeds were grown into $F_1$ plants. $F_2$ seeds, derived from selfing one $F_1$ plant were sown to obtain an $F_2$ population of 174 individuals. A $BC_2$ (backcross 2) population of 59 individuals was generated by two rounds of backcrossing with Moneymaker as the recurrent and female parent. Using MAS, $BC_2$, $BC_3$, and $BC_4$ genotypes were selected containing one of the two identified parthenocarpy-conferring genetic elements and some $BC_2$ were self pollinated to produce $BC_2S_1$ seeds (see FIG. 2). As stated above, one $F_1$ plant was self pollinated to obtain $F_2$ seeds and backcrossed to SL to obtain $BC_1$ seeds. The $F_2$ seeds were initially used for the construction of the genetic linkage map. The $BC_1$ seeds were used to develop the ILs (FIG. 3).

DNA Isolation and Marker Analysis

Genomic DNA was isolated from two young (rolled up) leaves using a cetyltrimethylammonium bromide (CTAB) based protocol according to Steward and Via (1993), adjusted for high throughput DNA isolation using one ml micronic tubes (Micronic BV, Lelystad, The Netherlands) and grounded using a Retsch 300 mm shaker at maximum speed (Retsch BV, Ochten, The Netherlands). The AFLP analysis (Vos et al., 1995) of $F_2$, $BC_2$, $BC_3$, $BC_4$ and $BC_2S_1$ populations was done and the AFLP fragments were resolved on a LI-COR 4200 DNA sequencer, essentially following the method published by Myburg (Myburg et al. 2001). The selective Pst primer was labeled with an IRD 700 or IRD 800 fluorescent label. AFLP gel images were scored using the AFLP-Quantar Pro software package (Keygene BV, Wageningen, The Netherlands). The following ten primer combinations and adapter sequences were used for genotyping: P14M48, P14M49, P14M50, P14M60, P14M61, P15M48, P18M50, P18M51, P22M50 and P22M51, as described by Bai et al. (2003).

Phenotypic Analysis of the $F_2$ Population

Variation in fruit size (Yield fruit weight, fruit hight, fruit diameter) and seed set (SS), were observed in plants obtained from crosses individuals of the $F_2$ population derived from the cross between Moneymaker x LYC 4/78 (See Table 1). Plants that were seedless (SS—) and exhibited normal fruit sizes compared to control (Moneymaker [SL] bottom row) were considered parthenocarpic.

TABLE 1

Total Yield and fruit characteristics [a]

| IL | Yield | FW | FH | FD | SS |
|---|---|---|---|---|---|
| 1-1 | 9.0 | 36.8 | 42.27 | 58.60 * | + |
| 1-2 | NA | 24.3 | 35.11 | 32.03 | − |
| 1-3/3-3 | NA | 19.3 ** | 30.47 ** | 32.95 ** | − |
| 1-4 | 10.8 | 67.2 | 41.92 | 48.97 | + |
| 2-1 | 16.9 | 70.4 | 41.08 | 51.33 | + |
| 2-2 | 6.1 | 28.3 ** | 34.85 * | 36.48 ** | − |
| 2-3 | 12.0 | 41.0 ** | 38.52 | 42.05 | + |
| 3-1 | 9.0 | 76.0 | 42.41 | 53.65 | + |
| 3-2 | 8.2 | 31.8 ** | 33.30 ** | 39.47 * | − |
| 4-1 | 10.6 | 49.8 | 36.89 | 46.60 | + |
| 4-2 | NA | 62.4 | 41.92 | 49.06 | + |
| 4-3 | 2.9 | 29.2 * | 33.49 ** | 37.48 ** | − |
| 5-1 | 23.9 | 76.3 | 44.29 | 51.91 | − |
| 5-2 | 12.6 | 65.3 | 41.13 | 49.31 | − |
| 6-1 | 13.1 | 49.2 | 41.20 | 43.36 | + |
| 6-2/7-2 | 10.2 | 45.9 | 38.30 | 42.23 | + |
| 6-3 | 14.9 | 77.9 | 46.15 | 50.91 | + |
| 7-1 | 6.0 | 41.8 | 37.07 | 41.80 | + |
| 8-2 | 2.8 | 8.2 ** | 21.85 ** | 22.71 ** | + |
| 9-1 | 9.1 | 60.8 | 41.31 | 47.24 | + |
| 9-2 | 4.6 | 28.6 ** | 32.42 | 35.76 * | − |
| 10-1 | 5.0 | 29.5 * | 33.50 | 35.86 * | − |
| 10-2 | 10.9 | 63.2 | 43.29 | 48.29 | + |
| 10-3 | 11.6 | 81.1 | 49.69 | 53.26 | + |
| 10-4 | 17.4 | 83.7 | 48.34 | 54.59 | + |
| 11-1/9-3 | 6.4 | 46.0 | 41.95 | 42.44 | ± |
| 11-2 | 6.7 | 36.4 | 34.64 | 39.90 | ± |
| 12-1 | 5.6 | 47.6 | 38.11 | 44.65 | − |
| 12-2 | 9.1 | 40.3 | 37.36 | 42.52 | + |
| 12-3 | 2.7 | 10.8 ** | 21.39 ** | 26.95 ** | − |
| BRC-5 | 4.1 | 33.8 ** | 36.28 | 39.73 * | − |
| SL | 11.5 | 58.3 | 42.27 | 47.42 | + |

[a] significant deviations from SL, as determined using a Dunnett test, are presented next to each mean. Probability of P < 0.05 (*) or P < 0.01 (**) is indicated.
Yield (Kg)
FW: Fruit weight (gram)
FH: Fruit height (mm)
FD: Fruit diameter (mm)
SS: Seed set Molecular Markers & Genetic Linkage Map A genetic linkage map was calculated for an $F_2$ population (n=174) derived from the cross of Moneymaker x LYC 4/78. Ten primer combinations were used to obtain 218 amplified fragment length polymorphism (AFLP) markers in the $F_2$ population (n=174). A total of 69 markers (31.7%) could be readily scored co-dominantly, thus allowing the calculation of an integrated $F_2$ genetic linkage map. Marker analysis performed on $BC_2$, $BC_3$ and $BC_2S_1$ genotypes allowed the addition of an additional 145 AFLP markers. A total of 102 out of these 145 additional AFLP markers were previously not scored due to complexity of the $F_2$ gels. The overall genetic linkage map consisted of 315 AFLP markers of 14 linkage groups and has a total length of 958 cM. Since co-migrating AFLP markers within a species are generally allele specific, co-linearity with other AFLP linkage maps was used to assign linkage groups to chromosomes. Some Moneymaker specific AFLP markers were in common with the genetic linkage maps as published (Haanstra et al. 1999; Bai et al. 2003) and therefore some linkage groups could be assigned to chromosomes, including the linkage groups harboring the identified parthenocarpy-conferring genetic elements. To improve the linkage map in the parthenocarpy-conferring genetic elements intervals, diagnostic CAPS markers were added in these regions based on the published S. lycopersicum x L. pennellii map (Tanksley et al. 1992; Haanstra et al. 1999).

Marker Analysis

Genomic DNA was isolated from two young (rolled up) leaves using a CTAB based protocol according to Steward et al. (1993), adjusted for high throughput DNA isolation using one ml micronic tubes (Micronic BV, Lelystad, The Netherlands) and grounded using a Retsch 300 mm shaker at maximum speed (Retsch BV, Ochten, The Netherlands).

AFLP analysis (Vos et al. 1995) of each backcross and IL was done and the AFLP fragments were resolved on a LI-COR 4200 DNA sequencer, essentially following the method published by Myburg (2001). The selective Pst primer was labeled with an IRD700 or IRD 800 fluorescent label. AFLP gel images were scored using the AFLP QUANTAR PRO software package. Primer and adapter sequences are described by Bai et al (2003).

Sets of CAPS primers were obtained from the "Solanaceae Genomics Website" or designed on sequences of genomic or cDNA clones available from the same source. Polymorphisms between S. habrochaites and S. lycopersicum were determined using the CAPS digestion approach described by Brugmans et al (2003). Marker sequences, PCR conditions, and specific restriction endonucleases used to genotype are presented in table 30. PCR products were generally separated using a 2.5% agarose gel. In Table 31 the different digestion products which discriminate between S. lycopersicum and S. habrochaites are indicated for each of the markers of Table 30 found in the QTLs of interest.

Results

IL Population

An introgression line (IL) population of S. habrochaites LYC 4/78 (SH) in the genetic background of S. lycopersicum cv. Moneymaker (SL) was developed. One $F_1$ plant derived from the cross between SL and SH was backcrossed to SL (FIG. 2). Subsequently a random set of 14 $BC_1$ plants was backcrossed to SL to obtain a $BC_2$ progeny (n=59). All $BC_2$ plants were genotyped and a selected set was backcrossed to SL. This set was chosen in such a way that the combined introgressions covered as much as possible of the SH genome while selecting recombinants in such a way that each alien chromosome will be represented by three ILs. This process of selection and backcrossing was repeated until $BC_5$. 31 selected $BC_5$ plants, mainly containing one or two introgressions were self pollinated. Up to 12 plants of each of the 31 $BC_5S_1$ families were self pollinated and screened with AFLP markers to obtain a $BC_5S_2$ progeny (n=44) homozygous for the introgression. The markers of the 44 ILs were screened once more and a core set of 30 ILs was chosen. This core set represents the maximum coverage of the SH genome in as few as possible ILs (FIG. 3). The core set consists of 15 ILs harboring a single introgression, 10 ILs containing two introgressions, 4 ILs containing three introgressions while one IL still contained four homozygous introgressions. On average each IL contained 60 cM (=5.2%) of the SH genome and the length of the introgressions varied between 20 (1.7%) and 122 cM (10.6%). Our IL population covers 95% of the length of the original $F_2$ linkage map. However, we realize this $F_2$ linkage map is not completely covering the genome. This is illustrated by additional CAPS analysis on chromosomes 3 (top of the short arm), 4 (top of the short arm), 5 (long arm) and 9 (top of the short arm) where CAPS markers revealed introgressions with no markers in the AFLP based $F_2$ linkage map. The size of these introgressions was estimated based on the high density RFLP map (Tanksley et al. 1992. Since no previous screening was applied for the top of Chromosome 3 the IL for this region is heterozygous. Plants, selected to be homozygous SH for IL5-1 and 5-2 failed to set seeds therefore these lines were maintained in their heterozygous state. No ILs containing the top of the short arm of Chromosome 8 and the bottom of the long arm of Chromosome 2 were present. Introgressions, on the top of the short arm of Chromosome 7 and 9 are present in multiple ILs. Selection for the top of Chromosome 9 was only possible after development of CAPS markers specific for this region. In the present description above IL5-1 is referred to as DRS5.1.

Marker Sequences as Used Herein.

The following Tables provide detailed information on the various RFLP and COS-II markers as indicated in the various linkage maps and as indicated for association with the QTLs of the present invention. The information of Tables 10-29 was directly copied in from the SOL Genomic Network (SGN) database hosted at Cornell University, version of 7 Oct. 2005.

The sequence of several markers found to be associated with the parthenocarpic trait through IL library screening as described herein were sequenced and provide for detailed information on the sequence of S. habrochaites LYC4/78 in the region of the parthenocarpy-conferring element disclosed herein.

TABLE 10

TG609 RFLP Marker

RFLP Information
Name: TG609
Insert size: 1900
Vector: pGEM4Z
Cutting Site: PST1
Drug Resistance: AMP Forward sequence GAGACAGCTTGCATGCCTGCAGAGGTGATAAATTCACCAAGGTTTCATAT
TTAGGAAACAAGAAATTAAAAGATCATTAACACAGATGAAAGGATATGA
CTAGGAGGCAATGACTGATCTTTGACTATCAAATACTTCTCAGGGAAACA
ATGTGAATGGGCTTTTACATGCAGAGATATTGATTGTGATCATGTTGAAG
AACTTAGGAAACATGAAATTAAATGATCATTAACACTGATGCAAGGATAT
GCCAAGTAGGCAAGCAAATTAAGGTTGAACATAAATGTCTGTGATCTTTG
ACTATCAAATATCTTCTCAGAAAAAAAAATGTGAATGCTCATTTACATGC
AGAGATGGCTATTGTGATCATGTGGCTCAGCCTTGAGTCTATATTGAGGT
GCAGACAACATAGTCCCTAACCACATGTGTGATCAAGCAACTTTTTTGAT
GTCCACAGGGTTTATAAGTAGGCAACATTTAAGCAAGAAAAAACACAGGAT
CACTATTGAGTCAGCTGCTGTTGCCTGT
(SEQ ID NO: 1)

Reverse sequence

GGAGACAAGCTTGCATGCCTGCAGAGGTGATAAATTCACCAAGGTTTCAT
ATTTAGGAAACAAGAAATTAAAAGATCATTAACACAGATGAAAGGATAT
GACTAGTAGGCAATGACTGATCTTTGACTATCAAATACTTCTCAGGGAAA

TABLE 10-continued

CAATGTGAATGGGCTTTTACATGCAGAGATATTGATTGTGATCATGTTGA
AGAACTTAGGAAACATGAAATTAAATGATCATTAACACTGATGCAAGGAT
ATGCCAAGTAGGCAAGCAAATTAAGGTTGAACATAAATGTCTGTGATCTT
TGACTATCAAATATCTTCTCAGAAAAAAAAATGTGAATGCTCATTTACAT
GCAGAGATGGCTATTGTGATCATGTGGCTCAGCCTTGAGTCTATATTGAG
GTGCAGACAACATAGTCCCTAACCACATGTGTGATCAAGCAACTTTTTTG
ATGTCCACAGGTTTATAAGTAGGCAACATTTAAGCAAGAAAAAACACAGG
ATCACTATTGAGTCAGCTGCTGTTGCCTGTTACTGAG
(SEQ ID NO: 2)

TABLE 11

TG62 RFLP Marker

RFLP Information
Name: TG62
Insert size: 1800
Vector: pUC
Cutting Site: PST1
Drug Resistance: AMP Forward sequence CAAAATGCTTCAGCTACTGGCTAAATGAAGTATGTTCTCAACATATTCAC
AAGCTTCTGTCTTCGAAGCTCAAGAAGTGTCGGTATTATCTGAATTAAAT
AGTAAAGCAAAGAGATGGTTTTATGTTTCTTAAGCAGCATTTCTTAGCTT
AACGGCCCTCCAGATATATGGTGGACAAAATAGAATCCATTAGATATAAC
AAATGGGATTAGTATAATGATCTTTTACTTTGTTAGATGATCATACTAAC
AGATTGCAAGTTAATCATATCCAACATATTCTGTAGATATTTCACATTGG
CTAGCATGAGGAAAGGTCATGTAGGAAATTGAATAGAGTTCAATTTTGGG
AAAAGTTGCATTGAAGAAGGTAACTTCAACAAACGTGTGAAAAAATCACA
TTTGAGTTGCCCGCTCACCATCGTGATTCCAGTACGAACTACTCAAAAAT
TTACTTTTGAGCCTTAAACATCATTTTAAGCCTTGAAAAGCTGCTTTTGA
AAAGATCTAAGCAAGAT
(SEQ ID NO: 3)

Reverse sequence

GGAGAATATTGTCACTCTATCAGATAGTTCAAAACTATCGGAGAATGAAA
TGGTCAATTCTTCTCACAAGATATTCATGCCTAGTTGCAGTGTCCGAATT
AACATAACATGCTCAATTTTCATATCTTGCAGCAAAATTTATCATTGAAA
CTCTCTGAGATGGAAACAGAGAACAAAGACCATATTGGAAAGCTTCAATC
AGACATGCAGAAAAAGGAAGATGAGATTCATGTTTTACGCAAGGAAATTG
ACAAATTACACGGAAACAGTGGATTCACTGGAGAAGCATGTTACAGAGATT
AACAATAAATTGGAGGAGAAAGATCAGCTTGTTCAGGAACTTCAGGACAA
GGAGAAGCAGTTGGAAGCTGACAGAGAAAAGGTTTTTACTACGGATACTT
TTAGTTCTACAAATTCTATTATAACCAATACAATGTGTTCAAGTGACTAG
TGTTTTGCACCTTGTTGCAGATTCAGGCATCTTTGCTTGCTGCTGAAAGC
AAGCTCACAGAATCCAAAAAGCAGTATGATCAGATGT
(SEQ ID NO: 4)

TABLE 12

TG555 RFLP Marker

RFLP Information
Name: TG555
Insert size: 1600
Vector: pGEM4Z
Cutting Site: PST1
Drug Resistance: AMP Forward sequence AATTCGGAGCTCACTGCTTCTAATCCTCAGTGAGACTTATTTTCTACATA
TTAAACAATAAGAAATTTACGAAGGAATATTATAGACTGAATTCCTTGGT
GACAAGTATCAAGACATCTTGACCAAGTTTAAAGTTTTGTAGTGGCAGTT
CTTTTAAGCTTTACTTGTGTGAGGTAGACATCAAGGAAGATAAGTAGCAG
CTACTCTTCACGGAGCAGCCCATAGGACACTCAAATTCACTATTGCGAGG
GTCAATCTACCAATTTATGGAACGATACCAGTAAAGTCATTTTTATGTAA
ACATCAGACAGCTTTTGACTAAGCAGAGACATGAATAAGTTCTATTTGTT
AGAAGTCGAAGAGACAAATAAGTTAATTTCACCTATGCTATAAAAGAGGA
CTCTTATAGTTATAAATACAGTACATTTTATTAAGGGGTTCTAATTGTTGA
CTATGATAGCAAGCATGCCGTACTAATT
(SEQ ID NO: 5)

TABLE 12-continued

Reverse sequence

ACATTTTGAGGAAGACAGGAGTTATGTATCGCCATCTGGTGTGCTCCAAG
AACATGACAGATATAAAAGACCGCGGGGTGCACCAGAGAAATGTTGCATT
GGAGCATATTGAACATCATAGGCTCAATGGAATTGTTTACTTTGCAGATG
ATGATAATATCTACTCACTTGAGTTGTTTGAGAGCATTAGATCGATCAAG
TAAGTTGAGATTCATCGCTCTTGTTTACATGACTTGTCTTTGTTTTGTCC
TGCTGTGAGCATGTTCAGGATGATGTTATGTGCTTTATGTAGATGTTCAA
GTCGATAATAGTGAATAGTCTAGAGCTATTTCACATATATTACAACTTCA
CTAACAAATTCTTTTCCTGGTGTCCTCGGTTCATCACTCTTCATAGTTAT
AAGAATAACAGTTGTAGATTAGACCACTGGTCGTGTGATTTTTGGACTTA
ATTATTATCTCAATTCTTCCTCAAAATAGCAGTCCTTAGATTAGAAGCTG
AGG
(SEQ ID NO: 6)

TABLE 13

CT50 RFLP Marker

RFLP Information
Name: CT50
Insert size: 1600
Vector: pBLUESC
Cutting Site: EcoR1
Drug Resistance: AMP Forward sequence CTTTTTTTTTTTTTATATATTGTGGTATAGATTATTATATAATAACAA
GGTGAATTAACATGAGAAATGAATAATTGTCACATTCTTGTTCTGTCCAT
TTTCCAGTAGCGGCTAGTTGGAAAATTTGTTGTAACATGTAACACAGGCT
GTCCACATTCTACTCCAGAGAGAAAGTTGGTAAGTAGTGGGGGCAAAAGA
TAGAGACCCCAATAGCTATCAATTCACTTTGTTGACAATCAAGATTTGAG
AAAAAAGATCAAAACTTTACCAACTTAGATAGCTCCATAATCAACTGTAG
GTACAATTCTTTAGTGAAATTGCGGCGTTCATCTTCTGGGGACGAAGAGT
AAGTAGACAATCAATTGTCTTGTAGAACTTGGGCTTTACCATTTTCCCTA
GGACATAAGCTCTTGATCGAAGCTTGAAGTTTAATTTTAGTGGCACTGGT
AATG
(SEQ ID NO: 7)

Reverse sequence

TTTTTTTTTTTTTTAGCCAAAATGCATACAAAAACTGATTCAGAAGATA
CGAGCTTGGCTCCTTCGTCGCCGGACAATAGAGGGCCGACGGCGTATTAC
GTTCAGAGTCCGTCACGTGATTCTCACGATGGCGAGAAGACAACGACGTC
GTTTCACTCTACTCCTGTTATCAGTCCCATGGTTCTCCTCCTCACTCTC
ACTCATCCGTCGGCCGTCACTCCCGTGATTCCTCTTCCTCCAGATTCTCC
GGCTCCCTCAAGCCTGGATCTCAGAAGATTTTACCCGACGCCGCCGGAGG
CGTCGGCGGCCGTCACCACCGCAAAGGGCAGAAGCCCTGGAAGGAATGTG
ATGTTATTTGAGGAAGAAGGACTACTTGAAGATGATAGATCCAGTAAATC
TCTTCCACGTCGTTGCTATGTCCTTGCTTTTTGTTGTTGGTTTCTTCGTC
CTTTTCTCCTTCTTTGCTCTCATCCTTTGGGGTGCTAGTCGACCTC
(SEQ ID NO: 8)

TABLE 14

C2_At1g74970 COS-II marker

Mapping experiments

Map: Tomato-EXPEN 2000

Forward primer (5'-3'):
TCATCATCAACTATCGTGATGCTAAG
(SEQ ID NO: 9)

Reverse primer (5'-3'):
ACGCTTGCGAGCCTTCTTGAGAC
(SEQ ID NO: 10)

Temperature: 55° C.
$Mg^{+2}$ concentration: 1.5 mM

TABLE 14-continued

PCR Product Sizes
LA716: 1000
LA925: 1000

Digested hand sizes (using AluI)
LA716: 550
LA925: 850

Mapped locations
| Map | Chromosome | Offset | Confidence |
|---|---|---|---|
| Tomato-EXPEN 2000 | 4 | 109.7 | I |

TABLE 15

CT128 RFLP marker

RFLP Information
Name: CT128
Insert size: 700
Vector: pBLUESC
Cutting Site: EcoR1
Drug Resistance: AMP Forward sequence CTTTTTTTTTTTTTCAACACAAACAAAATTTCATTATATTGTCAGGTAGC
ACACTACATCTTTACACTGTCATCAAACGACCAGAGACTTGAGAACGTTT
TAAGAGATTCATTTTCCGGGGACAAAGTTTGTGGCGAAAGCCCAGGCATT
GTTGTTTACGGGGTCTGCAAGGTGGTCAGCAAGGTTCTCCAATGGACCCT
TTCCGGTGACAATAGCTTGAACAAAGAATCCAAACATAGAGAACATAGCA
AGTCTACCGTTCTTGATCTCCTTTACCTTGAGCTCAGCAAATGCCTCTGG
GTCTTCAGCAAGGCCTAATGGGTCGAAGCTGCCACCAGGGTAGAGTGGGT
CGACAACCTCACCAAGAGGTCCACCAGCAATACGGTATCCCTCAACAGCT
CCCATCAACACAACTTGGCAAGCCCAGATGGCCAAGATGCTTTGTGCATG
GACCAAGCTTGGGTTGCCCAAGTAGTCAA
(SEQ ID NO: 11)

Reverse sequence

CTGGTGATTACGGGTGGGATACCGCTGGACTTTCAGCAGACCCTGAAACT
TTTGCCAAGAACCGTGAACTTGAGGTGATCCACTGCAGATGGGCTATGCT
TGGTGCTCTTGGATGTGTCTTCCCTGAGCTCTTGGCCCGTAATGGTGTCA
AGTTCGGTGAGGCTGTGTGGTTCAAGGCCGGATCCCAGATCTTCAGTGAA
GGTGGACTTGACTACTTGGGCAACCCAAGCTTGGTCCATGCACAAAGCAT
CTTGGCCATCTGGGCTTGCCAAGTTGTGTTGATGGGAGCTGTTGAGGGAT
ACCGTATTGCTGGTGGGACCTCTTGGTGAGGTTGTCGACCCACTCTACCC
TGGTGGCAGCTTCGACCCATTAGGCCTTGCTGAAGACCCAGAGGCATTTG
CTGAGCTCAAGGTAAAGGAGATCAAGAACGGTAGACTTGCTATGTTCTCT
ATGTTTGGATTCTTTGTTCAAGCTATTGTCACCGGAAAGGGTCCA
(SEQ ID NO: 12)

TABLE 16

TG599 RFLP marker

RFLP Information
Name: TG599
Insert size: 700
Vector: pGEM4Z
Cutting Site: PST1
Drug Resistance: AMP Forward sequence TGCTTTGAGACAGATGTCTCTCATTAAGTGACTGAAGCTTTCTTCTAGTT
GGCTAGCATATTCATTTTCAGCATATAATCTGTATCATGA
ACAAAATTGCGACAGTATTGAATTTTTATTGTTGAATAGTCTTTTTATTA
TCCCCGAAGTTGAGGGTGGAACTTACATTTTCTGTTGATC
CTTGCTTGCTGTTTTTGTAAACAAAAAAGCGTCACCCATTATTTTTCTTT
TATTCTTTCTAGGTTGGGACTAAGATTTTTTGAAATGAGA
AAGGTATTCGCTACCTTGAGGGCTGTGGTTGAAGTGATGGAGTATCTGAG
CAAAGATGCAGCTCCTGATGGTGTGGGAAGGCTTATAAAG
GAGGAGGGAGTATTTCCTTTCATTTCTTTGTATTTCCGTGTGTGTATAGT
CCGGAACTGGTTCCCTACTTATGAATTCTTTCATGGTTTG
GTCAATTGAGAAGGATCAAGAAATCTGATGCTACTTTATCATGGGAACTT
(SEQ ID NO: 13)

TABLE 16-continued

Reverse sequence

GCTTGCATGCCTGCAGAGTGGTCATACAATAAAAGGTAAAAATCAACATT
CTTACCTCTGGAAAGAAACCAATAGCATTGGTCAATGATG
CTGCCTCTAGAGGAACAATATTGTATGGTGCAAGTTCCCCTGATAAAGTA
GCATCAGATTTCTTGATCCTTCTCAACTGACCAAACCATG
AAAGAATTCATAAGTAGGGAACCAGTTCCGGACTATACACACACGGAAAT
ACAAAGAAATGAAAGGAAATACTACCTCCTCCTTTATAAG
CCTTCCCACACCATCAGGAGCTGCATCTTTGCTCAGATACTCCATCACTT
CAACCACAGCCCTCAAGGTAGCGAATACCTTTCTCATTTC
AAAAAATCTTAGTCCCAACCTAGAAAGAATAAAAGAAAAATAATGGGTG
ACGCTTTTTTGTTTACAAAAACAGCAAGCAAGGATCAACAG
AAAATCTAAGTTCCACCCTCAACTTCGGGGATAATAAAAAGACTATTCAA
CAATAAAAATTCAATACTGTCGCAA
(SEQ ID NO: 14)

TABLE 17

TG10 RFLP marker

RFLP Information
Name: TG10
Insert size: 900
Vector: pUC
Cutting Site: EcoRI/HindIII
Drug Resistance: AMP Forward sequence AACTCTGCTCTGCCAATAGTAGTCAGGCAGATCAAGATGCTCAAAATTTT
CTATTTGAATTGGAAGCATCAAGATGGTTCTTAGCATTTA
TTTTAGAAAGACTAACCATATTATCAAATAACCAGACTGAGACGCACACA
AAAGTTTCCCTCTATTATTTTTATAATGATGTGAAGATGC
TACATAATGAGTACACTTTGCCTTACTTTACTGCAGATGGACCTACCAGG
CCCAAACGGACATGTAGCTATGACAGAAGAGCAACCGCTA
TGAATGTCTCAAACTGTTGGCCTAGGCGATCAGCACAGATGATGAATCTG
GAAGTACATTCCAAGAAGGAAACTGGAGCGTGGGAACTA
ACCAGATGCAGGGGATGAATCCACACCTTTCAGTTGATCATCTGAAGGGA
AAACTAAGAATTTTCATGAGAAAATGACTGGCTATTTTCA
ACTTTG
(SEQ ID NO: 15)

Reverse sequence

TTCAATGCATTTAAGCTCAAAAAAACAAAGCTGTAGGAAGGAGCATATTA
GTAGCCTAACTCTGCTCTGCCAATAATAGTTAAGCAGATC
AAGATGCTCAAAATTTTCTAATTGAATTGTTAGCATCAAGATGCTTCTTA
GCATTTATTTTAGAAAGATTAACCATATTATCAAATAACC
AGACAGAGACGCACACAAAAGTTTCAATCTATTATTTTTATAATGATGTG
AAAATGCTACATAATGAGTACACTTTCCCTTACTTTACTG
CAGATGGACCTACCAGGCCCAAACGGTCATGTAGTTATGACAGAAGAACA
ACAGTATGAATTTCTCAAACTGTTGGCCAAGGTGATCAGC
AAAGATTATGAATTTGGAAGTACATTCCAAGAGGAAAGCTGGAGCATCGT
AACTAACCAGATGCAGGGGATGAATCCACACCTTTCAGTT
GATCATCTGAAGGCAAAACTAAGAATTTTCATGAGAAAATACTGGTTATT
TTCAACTTTGTTGGCCAGACGAGGAGTCCAATGGGATAGA
AGGACTAACTCAATGACGTATG
(SEQ ID NO: 16)

TABLE 18

TM2a TM marker

TM Information
Name: TM2A
Old COS ID: T0899

Sequence

CNAGCTCGANNNACCCTCACTAAAGGGAACAAAAGCTGGAGCTCCACCG
C
GGTGGCGGCCGCTCTAGAACTAGTGGATCCCCCGGGCTGCAGGCTCCTCC
ATTGAAAAGGGAATCAAGTTTGCCAAAGAAAACTAAAAAAACAAAATTA
T

GGTCTAGTTTTCTATAGTGACAGTTTTGGATCTTTTTGGGTCAATTGTTT
TTGTATCCTTTGCAAGTTTCTTGCAGCCGGAGGCTTAGATTTAGCTCTTT
TGATATTATACCCAACATTTCTACAAAATAATGTATGGCAAACTGGGGGC
CTATCCCATTTGCCTTAGTGTGGAGGTGTTATTCTCACATGAATCGTTTT
CCAATTATGGTTAGTAGCAGACAATTGATGCAAAATGAAGAAATGTTCAT
GACCAAAAAAAAAAAAAAAAAA
(SEQ ID NO: 17)

Mapped locations

| Map | Chromosome | Offset | Confidence |
|---|---|---|---|
| Tomato-EXPEN 2000 (TM2A) | 9 | 50.5 | I |

TABLE 19

TG551 RFLP marker

RFLP Information
Name: TG551
Insert size: 950
Vector: pGEM4Z
Cutting Site: PST1
Drug Resistance: AMP Forward sequence AATGAAGTTCAGTTGATAAGCTAAATGGTGGAAATACTAATTTTAATTGA
CAGTAACTTTGCATTTCAAGGTCCATACCAAAACATTTGC
TAACACCAGTTGCTTTGTCAACGAAAACCTTGGCACTCAAAACCCTACCA
AAAGGCTGAAATGCATTTGCAAGCTCTTGATCACCAAATT
CTTGAGGAATATGGTAAATAAATAGATTAGCACCAGGTGGACCTGTAAAC
AGCAAAATCGTTTTTGATAAGTACAGGTTTATTTCTACAT
GTTCAACTACCACTGCCAAGTACACTAGTTCAAGTGACATCTCCACCACT
TAATTGCATAAAGCTTTACCAACGACAAATATAACAAACT
TGTGCAAGTAATTTGAGTTCCTGTCTATACAGTCCAGAATCTCCATATGC
TGCTCATCTCACAATGTTGGTTAAGGAAATTTGTCAAGTA
AAGTTCAA
(SEQ ID NO: 18)

Reverse sequence

CATCTTCAAGTGTCAGCTCAAGTACAGGGGGTCAGGTTGAAGGTTGTTGA
ACATTTATTTTGTGACCTTTTTAGCTCTAGAATTTCTGTA
GCTAATCAAGTACAGTCCCATAACCTAGGGGCTGTTAGGGTTTTCTGCTG
AATGAGGCTGCTTGTCTTTATTTTGGTTAATTATTTTCTG
GAAATTGTTCCTCGTCATAGAGAATAGAAGTAGAAGAAGAAGAAGATAG
TATAATCTATTATATTTGTTTTTTACTTAATTTATAAAGAT
TCCATAAATGCATGTGATCTTTGATCAATGATATCTTATACAAGTGTATC
ACTAGAATCTATTATATTTGGATTTACTTATTTTATATAG
GATTTCATAAACGCATGTGATC
(SEQ ID NO: 19)

TABLE 20

T1405 COS Marker

COS Information

Name: T1405
MIPS Category: 1.05.01
EST Information

T1405 was developed from the EST trace TPTAR86TH.
*Arabidopsis* orthology

At match: T1405 best matches against the *Arabidopsis* BAC AC009243.3.
At position: 1.1490000
At identities: 0.677

TABLE 20-continued

T1405 COS Marker

Genbank protein hits

Best GenBank protein hit: AAF17692.1
Evalue: 1.5e-67
Identities: 0.677
Description "similar to beta-1,4-xylosidase dbj|BAA24107[*Arabidopsis thaliana*]"

| Mapped locations | | |
|---|---|---|
| Map | Chromosome | Offset |
| Tomato-EXPEN 2000 | 4 | 77.00 |

TABLE 21

CT173 RFLP marker

RFLP Information
Name: CT173
Insert size: 400
Vector: pBLUESC
Cutting Site: EcoRI
Drug Resistance: AMP Forward sequence TTTTTTTTTTTAAAAATTCAAACTCCAATTATTTGCAGTATAAAACTACA
GATACAAATCCCAGTACATGGTTTGAGGCACGATAATAAG
GTGCTGATGAAATCCAAGACATGAGTTCACAATACATTACTGACCAATAT
ATTTACAAAGATTAGGGTAATGGCAGTAAAATCGCTGATT
ACAGACAACATTCTTGGGATATATTTCATCTTAAAGATTAGGATTAGTAG
TATGTGTGGCAGTCACAGTAGAGACCATGGCATCAACTCC
GCAGATATTGTGACCCCTGCAGATCTTGTAATATCCGTGTTCTCCCCAAG
TCTTTCCCCAA
(SEQ ID NO: 20)

Reverse sequence

TTGGGGAAAGACTTGGGGAGAACACGGATATTACAAGATCTGCAGGGGTC
ACAATATCTGCGGAGTTGATGCCATGGTCTCTACTGTGAC
TGCCACACATACTACTAATCCTAATCTTTAAGATGAAATATATCCCAAGA
ATGTTGTCTGTAATCAGCGATTTTACTGCCATTACCCTAA
TCTTTGTAAATATTGGTCAGTAATGTATTGTGAACTCATGTCTTGGAT
TTCATCAGCACCTTATTATCGTGCCTCAAACCATGTACTG
GGATTTGTATCTGTAGTTTTATACTGCAAATAATTGGAGTTTGAATTTTT
AAAAAAAAAA
(SEQ ID NO: 21)

Tomato-EXPEN 2000 (*S. lycopersicum* LA925 × *S. pennellii* LA716 type F2.2000)

TABLE 22

TG254 RFLP marker

RFLP Information
Name: TG254
Insert size: 2200
Vector: pGEM4Z
Cutting Site: PST1
Drug Resistance: AMP Forward sequence CTAGTTGGATTGAAACAATTGGGAATATAGTGTAGGAAGACTTCGGGCA
ATTATCTGCTTTCTTCTATATCAAACTGGGTCTATTGAAG
AATTACAAACTGGACCTTAAATCTTTTGCCAGTTTTTGTAAAATTGATAA
ACTTTTGATATTTATTATGGAAATTCAAATATATCTTA
ATAGTAGCTTGTTAATTTATTTCAAGAGACCCTTTTCATTGTTCATAGTT
CATTATCATCCCCTTATCAGTAGTGCACCAAGGGTGTGAC
CTAGTGGTCAATTAAGTATGAATCATGAGTCTTAGACAGAAACACTAGGT

TABLE 22-continued

GATTTTCTTCCATGTGTCCTAGCCTCTTAGGCTTGGTGGA
TAGAGGAGGTATCCTGTCTTTCCCCTTTCCAGAAATTCATAGCATTATTT
TCTGTTCTTTATTGATAAATTATTCATTAGAACAGTTATT
AGAAATGTGGAACTGGTTGAGGTAGGCG
(SEQ ID NO: 22)

Reverse sequence

CAGAACAGAGAACATGTAAAGTTGTTCAACTAATGAGCATATTTAGAAAA
ACTTAGTGGCTATCAATAGTTGGCAATATGAAAACTAAGA
TAGTGTGGTCACCTGTTGATCAATTTCTTCTTCAATAGGCATCTTGTCAG
CTTCCTCTTGTAACAAGGCTTTCATTTGTGACTTGAGAAT
ATATCCAGGAGGAAGTGCATGCCTGTAATGGCATTCTTTACCATTTGGAC
AGGCCCAGAACCAACCGTACTGCTTTTTCTCCACAGCATC
CAAAAAGAATTTACATACCTGCATATAAACCAAATCATAAGCTTGATTTA
TGAAACGAGCACTGCATTCATGTTTGGCAATATTTGACTG
GAGGAGGAGTTTTAAAGGGGGAAATTAAGACTATAGACACATACACTAA
ATATGCATAAAACGCCAAAAGTACCCTGGTTTCCTATCCAG
TTAAGGCAACAGTAGCAGAAAATGAGTGTTGTAATGAGTCAAT
(SEQ ID NO: 23)

Tomato-EXHIR 1997 (*S. lycopersicum* TA209 × *S. habrochaites* LA1777 type BC1, 1997)

TABLE 23

TG223 RFLP marker

RFLP Information
Name: TG223
Insert size: 790
Vector: pGEM4Z
Cutting Site: PST1
Drug Resistance: AMP Forward sequence TATTCAAGAAAATATTGTGTAGTGTTCTCCAATATTCAACTATTTAAGTT
CAATGGATCTAGACACACAATATTATTAATTCTCGTCGCC
GATGGGATGGTTGAGTGATTGAAGCATAGGAATAACATCCTGGAGATTCT
AGGTTTGGACTCCAGTTTGAACATAAGTGTGAGCCCATCT
GCTTTATCTTACAAGTTCAATTCAAACTTGTGTGAGTGGGCCATAGTAGA
TCCATGCAAAATAGTGGTTATGACGCTATGGTGAGTTCAT
GAGAAGAATTATTGTTCCTTAGGAACAGTGACAGGAAATTCAATGGTCAA
ATAACATCAAGAAGACTTTTTGATTAGTTACTGAGTGAT
GTTCAGAAGAGGGACTAAAATATCTAACATGCCCCCTCAAGCTCCAGATGG
TAAAGCAACTTGAGTTTGAGTTACTAGAATTTAGTAACAT
AAAAAGGTTTTCCAT
(SEQ ID NO: 24)

Reverse sequence

TTTCCACACACACAAAAAAAACATCTTGAACACACTGTAATCCCCCTCTT
CATCAAATTCTCCTGTGTCAACAACTTCCTTAGCCAGT
AACCACACAACTTCCCTCTTCTGAACATTACAAAGTCGCTGATCCAGAAA
GTCTTGTTCTTGATGCTATTTGACCATTGAATTTCCTGTC
ACTATCCAACATGAATAGTGTTTGTAGGGAATAAATTGAAATCAGATTAC
AAGGATCCAAATATCCATCCCCAACAATGTACTGTTTATG
CCCGAAGGTGAGGATAAAAAGATGGAAAACCTTTTTATGTTACTAAATTC
TAGTAACTCAAACTCAAGTTGCTTTACCATCTGGAGCTTG
AGGGGGCATGTTAGATATTTAGTCCCTCTTCTG
(SEQ ID NO: 25)

Tomato-EXHIR 1997 (*S. lycopersicum* TA209 × *S. habrochaites* LA1777 type BC1, 1997)

TABLE 24

TG47 RFLP marker

RFLP Information
Name: TG47
Insert size: 1900

TABLE 24-continued

Vector: pUC
Cutting Site: EcoR1/BamH1
Drug Resistance: AMP

Forward sequence

TGCAGTTGAATTCGTCTTCTTAACACTATTCTCTTATGCTGTGCATCAAG
ACAACCACCCTCATTGGGCGGTCATTGCTTCTTCAGGCAT
GACCCTACAGTTAGTACATTTGGTTTTACCAAATCTTCTTCTAAGGATAA
ATCTATTTGACTATGGTTCACTCTCTAAATCATAAGCTGA
AACAACATCAACATACCCCGTGTAAATCATAAGCTAAAACAAACTCTAGA
ATAGCCTTACCTCATCATTCCTAGGACCATAATTATATCT
ATACTTAGTCAAATCATCATAAAATTTACCTACAAGACCATTTAGATCT
CACCTGATTAAGATTTGTTGGTTACTCGTAATCCCTTGAA
CTAAGGTGTAACATCTTAACCCCTCCTTTTGAGTATTTATACCATCATAT
TTTGAAACTTCTCGTAGGTTCATATGTTTCTTTTGGTACT
TGTTAGTATAGCTTGGAGTGGGACCCAAGGGGCTCCAGTGAGTTCTAGAC
AAGAAAAACGAGATTTGAACATTGCAGATTTTATGTTTTC
TGGT
(SEQ ID NO: 26)

Reverse sequence

CTTTGTTTGCTTGCAAGACAGAGATTTATACACGCTAATGCTATCTTTTT
GTGTCATTAACAGCTAGTTTGATTTGCTTGGTTAATACAG
TTATGGTAGATAGAGAAGATAGTTTCAAAATAGAAAGAATGATGTAGACA
GCATTAATGAATCTTTCTCCTTACAATTGTACCTTTGACA
AGGAATCCACCTTTTATAGGTAGTTTGGTGAGTTTGATGGAAGATTGTGG
TTGAATCTGGTTGAGTCATAGACACTACTTGTACATTCTT
TTATGACACTGACTTGATGTTGTAAGAGTGAAATGTATAGACTTATCAAC
AAATAACAGAGTAGAAATAAAAGTAGGTTGAAGATAGCTT
CTTGTTTGGTTCTAACTTGCTCCTTTGTTGACTGATATGATAACATTGTG
TCAATATAAGATGATTCAAATGTTGCCTGAATTTTTATG
AAATTGATATTCATCGTCCAGTTTAGAGAGTTCT
(SEQ ID NO: 27)

Tomato-EXPEN 2000 (*S. lycopersicum* LA925 × *S. pennellii* LA716 type F2.2000)

TABLE 25

TG393 RFLP Marker

RFLP Information
Name: TG393
Insert size: 1200
Vector: pGEM4Z
Cutting Site: PST1
Drug Resistance: AMP Forward sequence ACTGACTAAGCTGCTGGATTTGATTAGCCGAAGGAATTTACTTTTGGTTA
CATCTTGCTCCATCACCTTTGTCTTTATCTAGGTCAATCT
TGTACCATAGATGCAAATAACACTATGAACAGATTAACAATGTCTTGAGG
AGGATTAGGCTGTCAACAGCCTGCATAATAACAGGAACAA
CATTGGCGTTTGTTTGCATCAGTTACTGTGACTCTGATTAAAGGAGAAAA
TGTGGCATCCTCTGCTTATACTGTCAGTGTGTATACTTGT
CAGGTTAAGTTGGTTGCTATAATCTTTAATAATTCTTGATTTTGTGGTTG
TTTCTGAAGTAAATTGATATGTGGGCCTTTGAGCTGGAGG
AGATGGTACTTTAGCTATTCACTAACAATCGTTTACCTTAAAAATGTTAT
TCTGTAAGTATCTAACCAAATTCTGATCAC
(SEQ ID NO: 28)

Reverse sequence

TGCAGACACCAAAGAAACAATTGGTTATATAAAAAACAATCCACAATCAT
TCTCTATAGAAGTCACGCAAAGACACTACATAACCTCCAA
GTGCAATGAAGAGGATGCAGAATAAGAAGCTCAGAACTTCCAAAAGAAA
AGGTGACTGAAAATAAGTTTGCTGAAAAGGTACAAGGCAAG
TTCTAATTCTCAACTAGCTTTAGGTATACACTAAAGAAAAGGAAAATAAA
TTCCAAACAGAAGTTTCCATCCTACCTAGTACATAAAGA
AAAAGGTAAAAAGGAACATATGGAAGTGTTCCCCTGTTACCTAAACTTTT
GGTGATAAACAGTAATCATGATTACCCCCACCTCACACAC
CACCACTACAGCACAAAATTAGAAATGTTGTATGGACCATGATCAACCA
GCCAAGAATCCCAGAAGGAGAATAAAGGAGTTCTCTTAAT
CACAAGAGGAGAATATCATCTACT
(SEQ ID NO: 29)

Tomato-EXPEN 2000 (*S. lycopersicum* LA925 × *S. pennellii* LA716 type F2.2000)

TABLE 26

CT19 RFLP marker

RFLP Information
Name: CT19
Insert size: 300
Vector: pCR1000
Cutting Site: HindIII/EcoRI
Drug Resistance: KN Forward sequence Reverse sequence GCCCCAAAACTCCTGCTGGATTTTACTGGATCTCCACTTGCTGCGACAT
TGCTTGCCTCCGACAATCATCTTCCCAACTTCTTCCTTTT
TGTCTTGAAATTAATCCCTTGTACCCATTGCTGCTTCTAAATGACCTCCT
GCATCCCGGCGGATCCACTAGGTCTAAAGCTGCCGCCCCC
GC
(SEQ ID NO: 30)

Tomato-EXPEN 2000 (*S. lycopersicum* LA925 × *S. pennellii* LA716 type F2.2000)

TABLE 27

TG68 RFLP marker

RFLP Information
Name: TG68
Insert size: 1900
Vector: pUC
Cutting Site: EcoR1
Drug Resistance: AMP Forward sequence GGATTTTGATGAACTTGTATCTGTGCTTCTAGCTCCACCTAGGATGAGTT
TGGATTTGTACGATTAACAAATGTTTGAGCTGAAAGAATT
AAATTTGATTACACCTGCCTTTACATATTTTTGTTGCGTAAGGATTTTCT
ATGAAGAATATATATGTATGTATGTGTAAAGGATGCACTA
AGCATCTCGCATTTTGATAAAGAAATGAACTTTGGGCTTAACTCAACTCC
AAAAGTTAGCTCATGAAGTGAGGATATCGCGTAAGACCGT
ATAAGGAGACCTAGAACCCATCCCACAACAATGTGTGACTCCAACACATT
CACGCAAGTTCTGGGGAAGGGTTGCACTCGTAAGGGTTGT
GATGTAGGCAGCCATAATTGTGTGTACCCATTCGTTAGAAAACTACACTG
TGCAAGTGGAGTTAAATTGTATCTTTTTTGGTTTTGTGTG
AGTTGTTCAATCCCCTTGACATGAAAAAAAGAAGCAAAATTCAAGTATAA
TGGTAAAAGGGGATTCAAAAT
(SEQ ID NO: 31)

Reverse sequence

TTGGGTCAGCCATAGTACTTCGTGATATATCTCTGACAGAAGATATCTGC
TCAAGACCATGAACAATACGGAGACATAAGAAGGAAAGAA
GTTCAGTGCAGCACAAAATTTTAATAAGTTAACTTAAAGGGGGATAAGAG
GCAAAACCAATATAAAAGTTTGGACAGACAAATTTTAATT
AGTATCAAAGAGTGAATGATGCTAAAAGAAGAGATGCTTAAATATCTGAT
ACTATAAAGTAAGCCATGACTAATTGGTAATTATGAATGG
CATATGATACGACTATCAGTTTTGACTGTTGTCTACAATAATGATTTCAG
AAACATATGATATATTTCAAATAGAATTGAATAACAACAC
TTGTTCAAATACCTAGCTCTCGGAGGCAGATCCAGAATTTTAGAAAGTGG
GTGCAGTAAATCACAAGAGTACACCTCTGCTAGAATGGGT
GTGTACTGTAACAAAACCTGTTTTGATATGCATAT
(SEQ ID NO: 32)

Tomato-EXPEN 2000 (*S. lycopersicum* LA925 × *S. pennellii* LA716 type F2.2000)

TABLE 28

TG565 RFLP marker

RFLP Information
Name: TG565
Insert size: 1700
Vector: pGEM4Z
Cutting Site: PST1
Drug Resistance: AMP Forward sequence ACTAGCATCTCTTGGAGGATGCTGAGGTGTCAAGTGGTGTTGACCACTCG
TTACCACTGATTCACAGCTGGTGTCTTTCGAAGCAAGCTT
CGTCTGCAAAACAAGAATCACACTTTAATCCTCTGTTACCTAAAAACAAT
AGTTGTTTGATGTAATGAAAGAAGAATTTTCACTTCAATG
ATGGAAAGAAATCTTACAGTTTGAGTTTGCTTGCGAAAGTAGCCATTTT
CATACACCAGTTGAGAACTTGCTTCTGCAATCTATCATT
CTCTTCCATTAATAGCTTGTTCATTGCTGACAGCTTCCTATTCACACCCT
GAAGCCTTGATGACTCTTTCCTCTGTTTTTCCCTACATCT
ATACAACTCAAAGAAACAATCAATTATACTTCAAATTAATTGGGGTCGCT
AAAAATGAATCCTTTAGACTAACAACATCCCACAAGTCCT
TACCCCTACCTCGCAGAGGTAGAGA
(SEQ ID NO: 33)

Reverse sequence

TCAGCAAAATGTCACACAGAGAGTACAGTAGTAGAGCACAGTAGAGTAG
GGAGAAGTTGCCTCAAAAGAGGAAAAGAAAAGGTAACGAAC
CACACATTTGACAGCTCAAAACCACTTTACCAATCCAAACAAAAAATCAT
CACATTATCCCTCCCTTCTCTCCTCTATTACTCTCA
TTTTCCCCAAGTTTCAGGTACCTTTTTCCTAACATAATCCGCCCATAGTG
TTCATCATTCAAGATCTGTCCTTTTGAGGAGACTTCATTC
CTTACTATGGTCTTCTTTTTTTGATGATTTCTTATGTGAGATGTTGAAAA
CTGGAAAGAAGTGATAAAGATAGGAGGTTTGGTTTCTGGG
GTTTGTTTATTTTGCTTTACAAGGGTTAAAGATTGGATCTTTTTTAGTTT
TGGTAGATACCCATGTCTAATCTTGTTTCAGAATTCAAAA
GGTTGGTACTTTACTGTTTTGCAAGTGGATGACAGAGGAG
(SEQ ID NO: 34)

Tomato-EXPEN 2000 (*S. lycopersicum* LA925 × *S. pennellii* LA716 type F2.2000)

TABLE 29

TG296 RFLP marker

RFLP Information
Name: TG296
Insert size: 1100
Vector: pGEM4Z
Cutting Site: PST1
Drug Resistance: AMP Forward sequence TTAGGTTTTTGTGTGGTTCAACGTTTTTGGTTTTGATTTTTATGTGTTTT
CTTAGTTCCTTGCTTCACCATTTTGATGGTATTTTGAGTT
TTTGATGTTCTGTCGGCATAAAGTAGTGATTTTTCAGACAGTTTGGTATT
ATGGAGTATGTTTCTTTGCTCTTCTCTAATTTGGATTGGT
TCTGATTTGTATATGCTTGTTTTAGTTTCGATGGTTTTTGAGTTTTTGAT
GATTCATTGGCACAAAGTAGTGATTTTTTCAGACTGTTGGG
TTTTGTGGGGTTCCCGTGCTTGCTCTTCACTAATTTGGATTGGTTCTGAT
TTGTATATGTTTTAGTTTTGATGGTTTTTGAGTTTTTGAT
GATTCATCGGCACAAAGTAGTGATCTTTCAGACAGTTGGGTTTTGTGGGG
TTCACGTGCTTATTCTTCACTATTCTCGGTTGGTTTGATT
TGTAGGTCCGTTTTAGCAT
(SEQ ID NO: 35)

Reverse sequence

AGAATATAACAAAAAAGCAGATAAATCAGTTAATTATGCCTCAATCTCAA
CAAGTGAATAACAAATCCTATCAGAAGATATAGTAGACGA
TAAACAGTGAAGGTAGAAGCCTAACTCTATGACATTATCTTGAGACCCAA
AACACTTCATCAAAGACTCAAAAGAAATAATTTGTTCACC
AAGTACTATTAACTAATTATCAAAACTAGAATTCTCAAAATAAAAAATAA
CAAATCTTATCAGTCACATGGACATTCATTAAACATCATG
AAGAAGACAACAAGGGAAGGTCAAAACTGGACTCCATGGCACATAAGAT
AATAACAAAAGGTAGTTTAAGGCCTAAAACACTTCAAAAAT
AAAATTTATTCACCAGATATCAATAATATTATCTGTTCTTCCTTCATTCA
TGAGGGGCATGCACAAGAGACAATATACATCATTTCTCCT
TTTACTTTTTCTTTCCTGAGGAAGTAAAAGGAGCAGAAAGCAGATAGAAA
GA
(SEQ ID NO: 36)

Tomato-EXPEN 2000 (*S. lycopersicum* LA925 × *S. pennellii* LA716 type F2.2000)

TABLE 30

Primer sequences, lengths of PCR products and enzymes revealing a polymorphism for CAPS/SCAR markers.

| Marker name | Chromosome | Primer sequence (5'-3') | Observed PRC product length (bp) | Annealing Tm (° C.) | Marker Type | Enzyme |
|---|---|---|---|---|---|---|
| CT229 | 4 | ATGGGCTGGGATC GTAGTAAA (SEQ ID NO: 37) AAGCTTGCGATTC CCATAACA (SEQ ID NO: 38) | 336 | 55 | CAPS | MwoI |
| T1068 | 4 | CAAAGCAATGGGC AATGGT (SEQ ID NO: 39) ACACAGCAGTTTC AGTAGGAC (SEQ ID NO: 40) | 304 | 55 | CAPS | HincII |
| TG272 | 4 | GATTTTGCCCCCT CTACCA (SEQ ID NO: 41) ACATCTTTTCCTTC CCTCTGC (SEQ ID NO: 42) | 352 | 55 | CAPS | MnlI |
| TG264 | 4 | GGAACAGGTCAG GACAGCAT (SEQ ID NO: 43) | 520 | 55 | CAPS | HaeII |

TABLE 30-continued

Primer sequences, lengths of PCR products and enzymes revealing a polymorphism for CAPS/SCAR markers.

| Marker name | Chromosome | Primer sequence (5'-3') | Observed PRC product length (bp) | Annealing Tm (° C.) | Marker Type | Enzyme |
|---|---|---|---|---|---|---|
| | | TGGCTAACTGACG AAGACGA (SEQ ID NO: 44) | | | | |
| TG62 | 4 | CATGCCTAGTTGC AGTGTCC (SEQ ID NO: 45) TTCAGCAGCAAGC AAAGATG (SEQ ID NO: 46) | 410 | 63 | CAPS | DdeI |
| T1405 | 4 | CACCAACAACTAG CCCTTGA (SEQ ID NO: 47) AAGCAATTCCTCC AGCTTCA (SEQ ID NO: 48) | 535 | 55 | CAPS | BsaJI |
| CT50 | 4 | GACGGCGTATTAC GTTCAGA (SEQ ID NO: 49) CTAGCACCCCAAA GGATGAG (SEQ ID NO: 50) | 390 | 55 | CAPS | DdeI |
| TG441 | 5 | TGTCAGCATAGGC TTTTCCA (SEQ ID NO: 51) CGGTCGGGAAAA ATGACA (SEQ ID NO: 52) | 550 | 55 | CAPS | RsaI |
| CD31 | 5 | ATCTCGGGATCAT GGTTGAC (SEQ ID NO: 53) ATGGCCAGAGAA ATTCCAAA (SEQ ID NO: 86) | 501 | 55 | CAPS | HinfI |
| TG318 | 5 | CAAGCCATAGAAA TTGCCGTA (SEQ ID NO: 54) TGCTCTCTCTGTG ATGGAAGC (SEQ ID NO: 55) | 450 | 55 | SCAR | |
| TG358 | 5 | CAACTTTTCCAGG TTCATTTTCTC (SEQ ID NO: 56) ACACCTACATGCT ACTAAGGGGTC (SEQ ID NO: 57) | 700 | 55 | CAPS | DdeI |
| TG60 | 5 | TTGGCTGAAGTGA AGAAAAGTA (SEQ ID NO: 58) AAGGGCATTGTAA TATCTGTCC (SEQ ID NO: 59) | 400 | 55 | CAPS | HpyCH 41V |
| CT138 | 5 | ACCAGCCCCGGAA GATTTTA (SEQ ID NO: 60) GCGGTCAACTTCA GCAACTAT (SEQ ID NO: 61) | 364 | 55 | CAPS | RsaI |

TABLE 30-continued

Primer sequences, lengths of PCR products and enzymes revealing a polymorphism for CAPS/SCAR markers.

| Marker name | Chromo-some | Primer sequence (5'-3') | Observed PRC product length (bp) | Annealing Tm (° C.) | Marker Type | Enzyme |
|---|---|---|---|---|---|---|
| TG296 | 12 | TGTTCTGTCGGCATAAAGT (SEQ ID NO: 62) TGCTAAAACGGACCTACAA (SEQ ID NO: 63) | 373 | 55 | CAPS | HpyCH41V |

TABLE 31

Size table of alleles found at polymorphisms of Table 30, when cut with the indicated enzyme(s).

| Marker name | Chrom. | Location Tomato EXPEN 2000 or 1992 | Observed PCR product length | Alleles with discriminating capacity (estimated size digested [bp]) homozygous SL* | homozygous SH* | Sequenced[a] |
|---|---|---|---|---|---|---|
| CD 59 | 4 | 0 cM (2000) | | | | |
| CT229 | 4 | 12 cM (2000) | 400 | 300 + 100 | 400 | Yes |
| T1068 | 4 | 33 cM (2000) | | 130 + 670 | 900 | |
| TG272 | 4 | (50 cM) (1992) | | 200 | 250 | Yes |
| TG264 | 4 | 75 cM (2000) | | 450 | 160 + 280 | |
| TG62 | 4 | 82 cM (2000) | | 90 + 350 | 90 + 130 + 210 | Yes |
| T1405 | 4 | 77 cM (2000) | | 180 + 370 | 100 + 180 + 310 | Yes |
| CT50 | 4 | 101 cM (2000) | | 190 + 210 | 400 + 410 | Yes |
| T1181 | 5 | 0 cM (2000) | | | | |
| TG441 | 5 | 19 cM (2000) | | 450 | 180 + 270 | Yes |
| CD31 | 5 | 39 cM (1992) | | 160 + 300 | 400 + 160 | Yes |
| TG318 | 5 | 72 cM (2000) | | 450 | 270 | Yes |
| TG538 | 5 | 43 cM (1992) | | 180 + 250 | 120 + 300 | |
| TG60 | 5 | 104 cM (2000) | | ? + 300 + 360 | ? + 300 + 550 | Yes |
| CT138 | 5 | 119 cM (2000) | | 900 | 600 | Yes |
| CT211 | 12 | 38 cM (2000) | | | | |
| Tg68 | | 21 cM (2000) | | | | |
| TG296 | 12 | 96 (2000) | | 340 | 290 | Yes |

*SL = *Solanum lycopersicum*. SH = *Solanum habrochaites*. In heterozygous plants digested products of both SL and SH are found.
Both in Table 30 and Table 31 the observed PCR product length is estimated from agarose gel bands.
[a]See Table 32

TABLE 32

Nucleic acid sequences of selected markers providing mutations characterizing the S. habrochaites Lyc 4/78 genome over S. lycopersicum cv. Moneymaker.

>CD31 [LYC4 (SEQ ID NO: 64)/MM (SEQ ID NO: 75)]

TTCATTTTGTTATTTCCTTT[C/T]GCCTTCCTCCACTCAGACTGGAGTT
CTTCGTTATCAGCAAACTGTTCGACAGTTAAATGCATGTATGTTCAGTAT
AAGTAAAAGGGCAACCCAAGCTTCC[G/A]CTATGCACGG[G/A]GTC
[T/C]GGAGTAGGGCCGGACTAT

>CT50 [LYC4 (SEQ ID NO: 65)/MM (SEQ ID NO: 76)]

TGGAAGAGATTTACTGGATCTATCATCTTCAAGTAGTCCTTCTTCCTCAA
TAACATCACATTCCTTCCAGGGCTTCTGCCCTTTGCGGTGGTGACGGCCG
CC[T/GACGCCTCCG]GCGGCGTCGGGTAAAATCTTC[C/T]GAGATCCA
GGCTTGAGGGAGCCGGAGAATCTGGAGGAAGAGGAATCACG[C/G]GAGT
GACGGCCGAC[C/G]G

>CT138 [LYC4 (SEQ ID NO: 66)/MM (SEQ ID NO: 77)]

CAGAAGTTTAAC[A/T]TCACAAGCCACTGAA[G/C]ACG[A/G]TGAAA
GATGCTATAGAAATAGTCACAACTGATGAAATCATTACTGAGATAGCACC
AACCAGGTAGAATATTTTAACCAATGTGCAGAGCGTTCCAACTAA[T/C]
ACAGCATTAAAGATGATAATATCTCATGACTATTGCTGCTTTTGCAATGA
AAACGGGGTTTGTTTCAAAAAATATGGTGTTTGATTTTTTTT[T/C]AAA
AAAAGTTCAACACTTGATGA

>CT229 [LYC4 (SEQ ID NO: 67)/MM (SEQ ID NO: 78)]

GGCTGTGATATCGGAGTCAGAGCTCTGGCTTCACATCCAATGAAAGCAAA
TAAGAAAGGTATTGGGGAGAAGCACGTTCCCATAACCATTGCCGGGACTA
GAATCTGCGATGGTGAGTGGCTTTATGCAGATAC[T/C]GATGGCATTCT
GATTTCTAAAATGGAGCTATGTGTTTGAG

>T1405 [LYC4 (SEQ ID NO: 68)/MM (SEQ ID NO: 79)]

TTTCCAA[G/A]GCGAAAACCAACTCCCTTGCTGTCAT[T/C]GGTCATA
ATGCCAACAATGCTTATATTCTTCGTGGGAACTATGACGGTCCTCC[T/
C]TGCAAATACATCGAAAT[A/T]CTCAAGGC[G/A]TTGGTTGGTTATG
CAAAGTCAGTTCAGTACCAACAGGGTTGCAATGCGGCTAACTGCACGTCT
GCTAACATTGATCAAGCTGTCAACATTGCAAGAAATGCAGATTATGTTGT
TTTA[G/A]TCATGGGGTTGGATCAAACTCAAGAGAGGGAACAATTTGAT
CGCGATGACTTAGTGCTCCCGGGGCAGCAAGAAAATCTTATCAATAGTGT
TGCTAAAGCTGCA

>TG60 [LYC4 (SEQ ID NO: 69)/MM (SEQ ID NO: 80)]

TATAATGGAACAGTATCAAGGTAAAATATTGTATAACaacTACAAGA[C/
T]TCACTAGGAATGGTATACAAGTGAAACGTAAA[T/A]TAACAACTACA
AGACTC[A/G]CTACA[T/C]AGCTGATGCGATAATTGGTAATTATGAAG
GGCGAAATA[G/C]T[A/C]AAATTTCTTTCCAAGAAATCATGTCTTTTG
TCCTCATGGCTGAAGCTCAATTGTGT[A/C]CAAGAAACAAATGTAC

>TG62 [LYC4 (SEQ ID NO: 70)/MM (SEQ ID NO: 81)]

TTGGTTATAATAGAATTTGTAGAACTAAAAGTATCCGTAGTAAAAACCTT
TTCTCT[C/G]TCAGCTTCCAACTG[T/C]TTCTCCTTGTCCTGAAGTTC
CTGAACAAGCTGATCTTTCTCCTCCAATTTATTGTT[T/A]ATCTCTGTA
ACATGCTTCTCCAGTGAATCCACTGTTTCCGTGTAATTGTCAATTTCCTT
GCGTAAAACATGAATCTCATCTTCCTTTTTCTGCATGTCTGATTGAAGCT
TTCCAATATGGTCTTTGTTCTCT[A/G]TTTCCATCTCAGAGAGTTTCAA
TGATA

>TG272 [LYC4 (SEQ ID NO: 71)/MM (SEQ ID NO: 82)]

GGCTATTCTTGGATGGCTTCTCAAGGAAAAAGAATGTCT[T/A]TGTCAA
TGT[TG/CT]CAATTCTCGTATTCTTTATAAATCAAAGT[T/G]TCAA
[G/T]TCGGTGGCTGGGTCACGAATAAATAGAGTAGAAGTATGCT[C/A]
AACATCCCTGTGTTACAGTAGTCCCACTCT

>TG296 [LYC4 (SEQ ID NO: 72)/MM (SEQ ID NO: 83)]

TAATTTGGATTGGTTCTGATTTGTATATGCTTGTTTTAGTTTCGATGGTT
TTTGAGTTTTTGATGATTCATTGGCACAAAGTAGTGATTTTTCAGAC[A/
T]GTTGGGTTTT[A/G]TGGGGTTCCCGTGCTTGCTCTTCACTAATTTGG
ATTGGTTCTGATTTGTATATGTTT[GTTT/----]TAGTTTTGATGGTTT
TGAGTTTT

>TG318 [LYC4 (SEQ ID NO: 73)/MM (SEQ ID NO: 84)]

GATACTCAAAA[G/A]GAAGCTTGGTCCAGATGACCTTCGCACACAGGTA
CCTTCTGTCTCATGCACATGTATACAG[-/G]CACGAACAAATGC[G/A]
CTCTCTTCCCAGA[C/G]TGGTGCTG[C/T]ATAAA[A/G]AATTAC

>TG441 [LYC4 (SEQ ID NO: 74)/MM (SEQ ID NO: 85)]

AGCTGAGGTT TGGATTACTG GGCTGAAAGC AATAATTACG
AGGGGACGCT CTCGCAGAGG AAAATATGAT GCAAGAAGTG AAAC[T/
C]ATGTT TTCGGATAGT CCACTTGGTC [T/A]ACGAGTCAC
CACATCAACT TC[TA/AT]CTATTG TATGTTGGCA TTTTGTTGT[A/
G] CCTTCAGTTG TGTGTGTTCA TTCTTCCTCT CCT[A/C]TGACCT
CTTCCCCCTC CAACTGAT[C/A]C AAAATGTTG

REFERENCES

Ausubel F M, Brent R, Kingston R E, Moore D D, Seidman J G, Smith J A, Struhl K. (1995). "Current Protocols in Molecular Biology", 4th edition, John Wiley and Sons Inc., New York, N.Y.

Bai Y L, Huang C C, van der Hulst R, Meijer Dekens F, Bonnema G, Lindhout P (2003) QTLs for tomato powdery mildew resistance (*Oidium lycopersici*) in *Lycopersicon parviflorum* G1.1601 co-localize with two qualitative powdery mildew resistance genes. *Mol. plant microbe interactions* 16:169-176.

Benito E P, ten Have A, van't Klooster J W, van Kan J A L (1998) Fungal and plant gene expression during synchronized infection of tomato leaves by *Botrytis cinerea*. *Eur. J. Plant Pathol.* 104:207-220.

Bernacchi D, Tanksley S D (1997) An interspecific backcross of *Lycopersicon lycopersicum* x *L. hirsutum*: Linkage analysis and a QTL study of sexual compatibility factors and floral traits. *Genetics* 147:861-877.

Brugmans B, van der Hulst R G M, Visser R G F, Lindhout P, van Eck H J (2003) A new and versatile method for the successful conversion of AFLP (TM) markers into simple single locus markers. *Nucleic acids research* 31: Nil_9-Nil_17

Canady M A, Meglic V, Chetelat R T (2005) A library of *Solanum lycopersicoides* introgression lines in cultivated tomato. *Genome* 48: 685-697

Christou P, Murphy J E, and Swain W F (1987) Stable transformation of soybean by electroporation and root formation from transformed callus. *Proc. Natl. Acad. Sci. USA* 84:3962-3966.

Churchill G A, Doerge R W (1994) Empirical threshold values for Quantitative trait mapping. *Genetics* 138: 963-971.

Deshayes A, Herrera-Estrella L, Caboche M (1985) Liposome-mediated transformation of tobacco mesophyll protoplasts by an *Escherichia coli* plasmid. EMBO J. 4:2731-2737.

D'Halluin K, Bonne E, Bossut M, De Beuckeleer M, Leemans J (1992) *Plant. Cell* 4:1495-1505.

Dik A J, Koning G, Kohl J (1999) Evaluation of microbial antagonists for biological control of *Botrytis cinerea* stem infection in cucumber and tomato. *Eur. J. Plant Pathol.* 105:115-122.

Doganlar S, Frary A, Ku H M and Tanksley S D (2002) Mapping Quantitative Trait Loci in Inbred Backcross Lines of *Lycopersicon pimpinellifolium* (LA1589). *Genome* 45:1189-1202.

Draper J, Davey M R, Freeman J P, Cocking E C and Cox B J (1982) Ti plasmid homologous sequences present in tissues from *Agrobacterium* plasmid-transformed *Petunia* protoplasts. *Plant and Cell Physiol.* 23:451-458.

Dunnett C W (1955) A multiple comparison procedure for comparing several treatments with a control. *Journal of the American Statistical Association* 50: 1096-1121.

Eckstein F (ed) (1991) *Oligonucleotides and Analogues, A Practical Approach*. Oxford Univ. Press, NY 1991.

Eduardo I, Arus P, Monforte A J (2005) Development of a genomic library of near isogenic lines (NILs) in melon (*Cucumis melo* L.) from the exotic accession PI161375. *Theor Appl Genet* 112: 139-148

Egashira H, Kuwashima A, Ishiguro H, Fukushima K, Kaya T, Imanishi S (2000) Screening of wild accessions resistant to gray mold (*Botrytis cinerea* Pers.) in *Lycopersicon*. *Acta physiologiae plantarum* 22:324-326.

Eshed Y, Zamir D (1994) A genomic library of *Lycopersicon pennellii* in *S. lycopersicum*: a tool for fine mapping of genes. Euphytica. Dordrecht: Kluwer Academic Publishers. 1994 79: 175-179

Eshed Y, Zamir D (1995) An introgression line population of *Lycopersicon pennellii* in the cultivated tomato enables the identification and fine mapping of yield-associated QTL. Genetics. Bethesda, Md.: Genetics Society of America. November 1995 141: 1147-1162

Foolad M R, Zhang L P, Khan A A, Nino Liu D, Liln G Y (2002) Identification of QTLs for early blight (*Alternaria solani*) resistance in tomato using backcross populations of a *Lycopersicon lycopersicum* x *L. hirsutum* cross. *Theor. Appl. Genetics* 104:945-958.

Frary A, Doganlar S, Frampton A, Fulton T, Uhlig J, Yates H, Tanksley S (2003) Fine mapping of quantitative trait loci for improved fruit characteristics from *Lycopersicon chmielewskii* chromosome 1. *Genome* 46: 235-243

Frary A, Nesbitt T C, Grandillo S, Knaap Evd, Cong B, Liu J, Meller J, Elber R, Alpert K B, Tanksley S D (2000) fw2.2: a quantitative trait locus key to the evolution of tomato fruit size. *Science Washington*. 2000; 289: 85-88.

Fridman E, Carrari F, Liu Y S, Fernie A R, Zamir D (2004) Zooming in on a quantitative trait for tomato yield using interspecific introgressions. *Science* 305: 1786-1789.

Fridman E, Pleban T, Zamir D (2000) A recombination hotspot delimits a wild-species quantitative trait locus for tomato sugar content to 484 by within an invertase gene. *Proc Natl Acad Sci USA*. Washington, D.C.: National Academy of Sciences. Apr. 25, 2000 97: 4718-4723.

Fulton T, van der Hoeven R, Eannetta N, Tanksley S (2002). Identification, Analysis and Utilization of a Conserved Ortholog Set (COS) Markers for Comparative Genomics in Higher Plants. *The Plant Cell* 14(7): 1457-1467.

Godoy G, Steadman J R, Dickman M B, Dam R (1990) Use of mutants to demonstrate the role of oxalic acid in pathogenicity of *Sclerotinia sclerotiorum* on *Phaseolus vulgaris*. *Physiological Molecular Plant Pathology* 37, 179-191.

Grandillo S, Tanksley S D (1996) QTL analysis of horticultural traits differentiating the cultivated tomato from the closely related species *Lycopersicon pimpinellifolium*. *Theor Appl Genet* 92: 935-951.

Gruber M Y, Crosby W L (1993) Vectors for Plant Transformation. In: Glick BR and Thompson J E (Eds.) *Methods in Plant Molecular Biology & Biotechnology*, CRC Press, pp. 89-119.

Haanstra J P W, Wye C, Verbakel H, Meijer Dekens F, van den Berg P, Odinot P, van Heusden A W, Tanksley S, Lindhout P, Peleman J (1999) An integrated high density RFLP-AFLP map of tomato based on two *Lycopersicon lycopersicum* x *L. pennellii* F$_2$ populations. *Theor. Appl. Genetics* 99: 254-271.

Hain R, Stabel P, Czernilofsky A P, Steinbliss H H, Herrera-Estrella L, Schell J (1985) Uptake, integration, expression and genetic transmission of a selectable chimaeric gene to plant protoplasts. *Mol. Gen. Genet*. 199:161-168.

Horsch R B, Fry J E, Hoffman N L, Eichholts D, Rogers S G, Fraley R T (1985) A simple method for transferring genes into plants. *Science* 227:1229-1231.

Jansen R C (1993) Interval Mapping of Multiple Quantitative Trait Loci. *Genetics* 135:205-211

Jansen R C (1994) Controlling the Type I and Type II Errors in Mapping Quantitative Trait Loci. *Genetics* 138:871-881.

Jeuken M J W, Lindhout P (2004) The development of lettuce backcross inbred lines (BILs) for exploitation of the *Lactuca saligna* (wild lettuce) germplasm. *Theor Appl Genet* 109: 394-401

Kado C I (1991) Molecular mechanisms of crown gall tumorigenesis. *Crit. Rev. Plant Sci.* 10:1-32.

Klein T M, Gradziel T, Fromm M E, Sanford J C (1988). Factors influencing gene delivery into *zea mays* cells by high velocity microprojectiles. *Biotechnology* 6:559-563.

Klein T M, Arentzen R, Lewis P A, and Fitzpatrick-McElligott S (1992) Transformation of microbes, plants and animals by particle bombardment. *Bio/Technology* 10:286-291.

Kosambi D D (1944) The estimation of map distances from recombination values. *Ann. Eugen.* 12:172-175.

Ku H M, Liu J, Doganlar S, Tanksley S D (2001) Exploitation of Arabidopsis-tomato synteny to construct a high-resolution map of the ovate-containing region in tomato chromosome 2. Genome. Ottawa, Ontario, Canada: National Research Council of Canada. June 2001 44: 470-475

Laursen C M, Krzyzek R A, Flick C E, Anderson P C, Spencer T M (1994) Production of fertile transgenic maize by electroporation of suspension culture cells. *Plant Mol Biol*. 24(1):51-61.

Lin S Y, Sasaki T, Yano M (1998) Mapping quantitative trait loci controlling seed dormancy and heading date in rice, *Oryza sativa* L., using backcross inbred lines. *Theor Appl Genet* 96: 997-1003.

Miki B L, Fobert P F, Charest P J, Iyer V N (1993) Procedures for Introducing Foreign DNA into Plants. In: Glick B R and Thompson J E (Eds.) *Methods in Plant Molecular Biology & Biotechnology*, CRC Press, pp. 67-88.

Moloney M M, Walker J M, Sharma K K (1989) High efficiency transformation of *Brassica napus* using *Agrobacterium* vectors. *Plant Cell Reports* 8:238-242.

Monforte A J, Friedman E, Zamir D, Tanksley S D (2001) Comparison of a set of allelic QTL-NILS for chromosome 4 of tomato: deductions about natural variation and implications for germplasm utilization. *Theor appl genet*. Berlin; Springer Verlag. March 2001 102: 572-590

Monforte A J, Tanksley S D (2000a) Development of a set of near isogenic and backcross recombinant inbred lines containing most of the *Lycopersicon hirsutum* genome in a *L. esculentum* genetic background: A tool for gene mapping and gene discovery. *Genome* 43: 803-813

Monforte A J, Tanksley S D (2000b) Fine mapping of a quantitative trait locus (QTL) from *Lycopersicon hirsutum* chromosome 1 affecting fruit characteristics and agronomic traits: breaking linkage among QTLs affecting different traits and dissection of heterosis for yield. *Theor appl genet*. Berlin; Springer Verlag. February 2000 100: 471-479

Myburg A A, Remington D L, O' Malley D M, Sederoff R R, Whetten R W (2001) High-throughput AFLP analysis using infrared dye-labeled primers and an automated DNA sequencer. *Biotechniques* 30: 348-357.

Nesbitt T C, Tanksley S D (2001) fw2.2 directly affects the size of developing tomato fruit, with secondary effects on fruit number and photosynthate distribution. *Plant Physiol.* 127: 575-583.

Nicot P C, Moretti A, Romiti C, Bardin M, Caranta C, Ferrière H (2002) Differences in susceptibility of pruning wounds and leaves to infection by *Botrytis cinerea* among wild tomato accessions. *TGC Report* 52: 24-26.

Paterson A H (ed.) (1996) Genome Mapping in Plants, Academic Press Inc San Diego, Calif., USA.

Pestsova E G, Borner A, Roder M S (2001) Development of a set of *Triticum aestivum-Aegilops tauschii* introgression lines. *Hereditas* 135: 139-143.

Phillips R L, Somers D A, Hibberd K A. 1988. Cell/tissue culture and in vitro manipulation. In: G. F. Sprague & J. W. Dudley, eds. *Corn and corn improvement,* 3rd ed., p. 345-387. Madison, Wis., USA, American Society of Agronomy.

Pierik R L M (1999) In vitro Culture of Higher Plants, 4th edition, 360 pages, ISBN: 0-7923-5267-X.

Prins T W, Tudzynski P, von Tiedemann A, Tudzynski B, ten Have A, Hansen M E, Tenberge K, van Kan J A L (2000) Infection strategies of *Botrytis cinerea* and related necrotrophic pathogens. In "Fungal Pathology" (J. Kronstad, editor). Kluwer Academic Publishers, pp. 33-64.

Ramsay L D, Jennings D E, Bohuon E J R, Arthur A E, Lydiate D J, Kearsey M J, Marshall D F (1996) The construction of a substitution library of recombinant backcross lines in *Brassica oleracea* for the precision mapping of quantitative trait loci. *Genome* 39: 558-567

Roupe van der Voort J N A M, van Zandvoort P, van Eck H J, Folkertsma R T, Hutten R C B, Draaistra J, Gommers F J, Jacobsen E, Helder J, Bakker J (1997) Use of allele specificity of comigrating AFLP markers to align genetic maps from different potato genotypes. *Mol. Gen Genetics* 255: 438-447.

Rousseaux M C, Jones C M, Adams D, Chetelat R, Bennett A, Powell A (2005) QTL analysis of fruit antioxidants in tomato using *Lycopersicon pennellii* introgression lines. *Theor Appl Genet* 111: 1396-1408

Sambrook J, and Russell D W (2001). Molecular Cloning: A Laboratory Manual. New York, N.Y., USA., Cold Spring Harbor Laboratory Press.

Sanford J C, Klein T M, Wolf E D, Allen N (1987). Delivery of substances into cells and tissues using a particle bombardment process. *J. Particulate Sci. Technol.* 5:27-37.

Sanford J C (1988) The biolistic process. *Trends in Biotechnology* 6:299-302.

Sanford J C (1990) Biolistic plant transformation. *Physiologica Plantarum* 79: 206-209.

Sanford J C, Smith F D, and Russell J A (1993) Optimizing the biolistic process for different biological applications. *Methods in Enzymology* 217:483-509.

Sobir O T, Murata M, and Motoyoshi F (2000) Molecular characterization of the SCAR markers tightly linked to the TM-2 locus of the genus *Lycopersicon. Theor. Appl. Genet.* 101: 64-69.

Steward C N, Via LE (1993) A rapid CTAB DNA isolation technique useful for RAPD fingerprinting and other PCR applications. *Biotechniques* 14: 748-750.

Tanksley S D (1993) Mapping polygenes. *Annu Rev Genet* 27: 205-233

Tanksley S D, Ganal M W, Prince J P, de Vicente M C, Bonierbale M W, Broun P, Fulton T M, Giovannoni J J, Grandillo S, Martin G B (1992) High density molecular linkage maps of the tomato and potato genomes. *Genetics* 132: 1141-1160.

Tanksley S D, Grandillo S, Fulton T M, Zamir D, Eshed Y, Petiard V, Lopez J and Beck-Bunn T (1996) Advanced backcross QTL analysis in a cross between an elite processing line of tomato and its wild relative *L. pimpinellifolium. Theor Appl Genet* 92: 213-224.

Tanksley S D, Young N D, Paterson A H, Bonierbale M W (1998) RFLP mapping in plant breeding: New tools for an old science. *Bio/technology* 7: 257-263.

Tijssen P (1993) Hybridization With Nucleic Acid Probes. Part I. Theory and Nucleic Acid Preparation. In: Laboratory Techniques in Biochemistry and Molecular Biology. Elsevier.

Urbasch I (1986) Resistenz verschiedener Kultur- and Wildtomatenpflanzen (*Lycopersicon* spp.) gegenüber *Botrytis cinerea* Pers. *J Phytopathol* 116: 344-351

Utkhede R, Bogdanoff C, McNevin J (2001) Effects of biological and chemical treatments on *Botrytis* stem canker and fruit yield of tomato under greenhouse conditions. *Can. J. Plant Pathol* 23: 253-259

Utkhede R S, Mathur S (2002) Biological control of stem canker of greenhouse tomatoes caused by *Botrytis cinerea. Can. J. Microbiol.* 48: 550-554

Van Berloo R (1999) GGT: Software for the display of graphical genotypes. *J. Heredity* 90: 328-329

Van Berloo R, Aalbers H, Werkman A, Niks R E (2001) Resistance QTL confirmed through development of QTL-NILS for barley leaf rust resistance. *Mol. Breeding* 8: 187-195

Van Heusden A W, Koornneef M, Voorrips R E, Bruggemann W, Pet G, Vrielink van Ginkel R, Chen X, Lindhout P (1999) Three QTLs from *Lycopersicon peruvianum* confer a high level of resistance to *Clavibacter michiganensis* ssp *michiganensis. Theor. Appl. Genetics* 99: 1068-1074.

von Korff M, Wang H, Leon J, Pillen K (2004) Development of candidate introgression lines using an exotic barley accession (*Hordeum vulgare* ssp *spontaneum*) as donor. *Theor Appl Genet* 109: 1736-1745

Voorrips R E (2002) MapChart: software for the graphical presentation of linkage maps and QTLs. *J. Heredity* 93: 77-78.

Vos P, Hogers R, Bleeker M, Reijans M, van de Lee T, Hornes M, Frijters A, Pot J, Peleman J, Kuiper M (1995) AFLP: a new technique for DNA fingerprinting. *Nucl. Acids Res.* 23: 4407-4414.

Wehrhahn C, Allard R W (1965) The detection and measurement of the effects of individual genes involved in inheritance of a quantitative character in wheat. *Genetics* 51: 109-119.

Zamir D (2001) Improving plant breeding with exotic genetic libraries. Nature reviews genetics 2: 983-989.

Zhang L, Cheng L, Xu N, Zhao M, Li C, Yuan J, and Jia S (1991) Efficient transformation of tobacco by ultrasonication. *Biotechnology* 9:996-997.

What is claimed:

1. A parthenocarpic and optionally male sterile *Solanum lycopersicum* tomato plant having fruits that are entirely seedless, or part thereof, obtained by a method comprising introgressing into a *S. lycopersicum* tomato plant a genetic region only from Chromosome 4 and/or 5 of *Solanum habrochaites* LYC4/78, of which a representative sample of seed of said *S. habrochaites* LYC4/78 was deposited Nov. 13, 2007, with the NCIMB under Accession Number 41517, wherein the genetic region from Chromosome 4 is between Markers CD59 and TG272 and includes marker CD59, wherein the genetic region from Chromosome 5 is between COS Marker T1181 and RFLP Marker CD31(A) and includes at least one marker selected from the group consisting of COS Marker T1181, RFLP Marker TG441 and RFLP Marker CD31(A), and wherein said parthenocarpic tomato plant is not *S. lycopersicum* cv. Moneymaker.

2. A parthenocarpic and optionally male sterile inbred *Solanum lycopersicum* tomato plant having fruits that are entirely seedless, or part thereof, obtained by a method comprising:
   a) producing a parthenocarpic tomato plant according to claim 1;
   b) crossing said parthenocarpic tomato plant with itself or another tomato plant to yield progeny tomato seed;
   c) growing said progeny tomato seed to yield additional parthenocarpic tomato plants; and
   d) repeating steps b) and c) from 0 to about 7 times to generate a parthenocarpic inbred *Solanum lycopersicum* tomato plant comprising a genetic region from Chromosome 4 of *S. habrochaites* LYC4/78 between markers CD59 and TG272 and/or a genetic region from Chromosome 5 of *S. habrochaites* LYC4/78 between COS marker T1181 and RFLP marker CD31(A);
   wherein said inbred tomato plant is not *S. lycopersicum* cv. Moneymaker.

3. A hybrid *Solanum lycopersicum* tomato plant, or parts thereof, that exhibits a parthenocarpic and optionally male sterile phenotype, wherein said hybrid tomato plant is obtained by crossing a parthenocarpic inbred tomato plant of claim 2 with an inbred tomato plant that exhibits commercially desirable characteristics.

4. A parthenocarpic and optionally male sterile *Solanum lycopersicum* tomato plant according to claim 1,
   wherein the genetic region from Chromosome 4 of *S. habrochaites* LYC4/78 further includes at least one marker selected from the group consisting of RFLP Marker CT229 and COS Marker T1068.

5. A tissue culture of regenerable cells of a tomato plant of claim 1.

6. A tissue culture of regenerable cells of a tomato plant of claim 1 wherein said regenerable cells comprise cells or protoplasts isolated from a tissue selected from the group consisting of leaves, pollen, embryos, roots, root tips, anthers, flowers, fruits, stems and seeds.

7. The tomato plant or part thereof according to claim 1, wherein the genetic region from Chromosome 4 of *S. habrochaites* LYC4/78 does not include markers TG272, TG264, TG62, T1405, and/or CT50.

8. The tomato plant or part thereof according to claim 1, wherein the genetic region from Chromosome 5 of *S. habrochaites* LYC4/78 does not include RFLP Marker TG318 or markers downstream therefrom.

9. The tomato plant or part thereof according to claim 1, wherein said parthenocarpic and optionally male sterile tomato plant is a cultivated *S. lycopersicum* plant.

* * * * *

UNITED STATES PATENT AND TRADEMARK OFFICE
CERTIFICATE OF CORRECTION

PATENT NO. : 9,125,353 B2
APPLICATION NO. : 12/619051
DATED : September 8, 2015
INVENTOR(S) : Anita Afke De Haan et al.

It is certified that error appears in the above-identified patent and that said Letters Patent is hereby corrected as shown below:

Title Page, Item (63), please delete "May 18, 2008" and please insert --May 19, 2008--

Signed and Sealed this
Fifth Day of July, 2016

Michelle K. Lee
*Director of the United States Patent and Trademark Office*